(12) United States Patent
Brinson, Jr. et al.

(10) Patent No.: US 7,844,088 B2
(45) Date of Patent: Nov. 30, 2010

(54) METHODS AND SYSTEMS FOR DATA ANALYSIS AND FEATURE RECOGNITION INCLUDING DETECTION OF AVIAN INFLUENZA VIRUS

(75) Inventors: Robert M. Brinson, Jr., Rome, GA (US); Nicholas Levi Middleton, Cartersville, GA (US); Bryan Glenn Donaldson, Cumming, GA (US)

(73) Assignee: Intelliscience Corporation, Atlanta, GA (US)

( * ) Notice: Subject to any disclaimer, the term of this patent is extended or adjusted under 35 U.S.C. 154(b) by 960 days.

(21) Appl. No.: 11/674,997

(22) Filed: Feb. 14, 2007

(65) Prior Publication Data

US 2007/0282937 A1    Dec. 6, 2007

Related U.S. Application Data

(60) Provisional application No. 60/773,377, filed on Feb. 14, 2006, provisional application No. 60/743,711, filed on Mar. 23, 2006.

(51) Int. Cl.
*G06K 9/00* (2006.01)

(52) U.S. Cl. .................... 382/128; 382/155; 382/159

(58) Field of Classification Search ................ 382/128, 382/133, 134, 155, 159
See application file for complete search history.

(56) References Cited

U.S. PATENT DOCUMENTS 6,122,396 A * 9/2000 King et al. ................. 382/133
7,751,602 B2 * 7/2010 Collins et al. .............. 382/128
2002/0168657 A1 11/2002 Chen et al.
2004/0219517 A1 11/2004 Ecker et al.
2005/0049498 A1 3/2005 Roche et al.
2006/0024669 A1 2/2006 Bogoch et al.
2007/0140540 A1 * 6/2007 McLaren et al. ............ 382/128

OTHER PUBLICATIONS

Rowe et al., "Detection of Antibody to Avian Influenza A (H5N1) Virus in Human Serum by Using a Combination of Serologic Assays," Journal of Clinical Microbiology, vol. 37, No. 4, pp. 937-943. Apr. 1999.

* cited by examiner

*Primary Examiner*—Vu Le
*Assistant Examiner*—Claire Wang
(74) *Attorney, Agent, or Firm*—Black Lowe & Graham, PLLC

(57) ABSTRACT

Systems and methods for automated pattern recognition and detection of avian influenza virus in a data set corresponding to an aspect of a biological sample. The method includes receiving a first data set corresponding to a first aspect of a first biological sample, analyzing the first data set using results of a first series of algorithms processed on a second data set corresponding to an aspect of a second biological sample known to contain avian influenza virus, generating an algorithm value cache for the first data set by running a second series of algorithms on the first data set, generating a match result by comparing the algorithm value cache with the results of the first series of algorithms, and performing a processing action based on the generated match result.

18 Claims, 63 Drawing Sheets

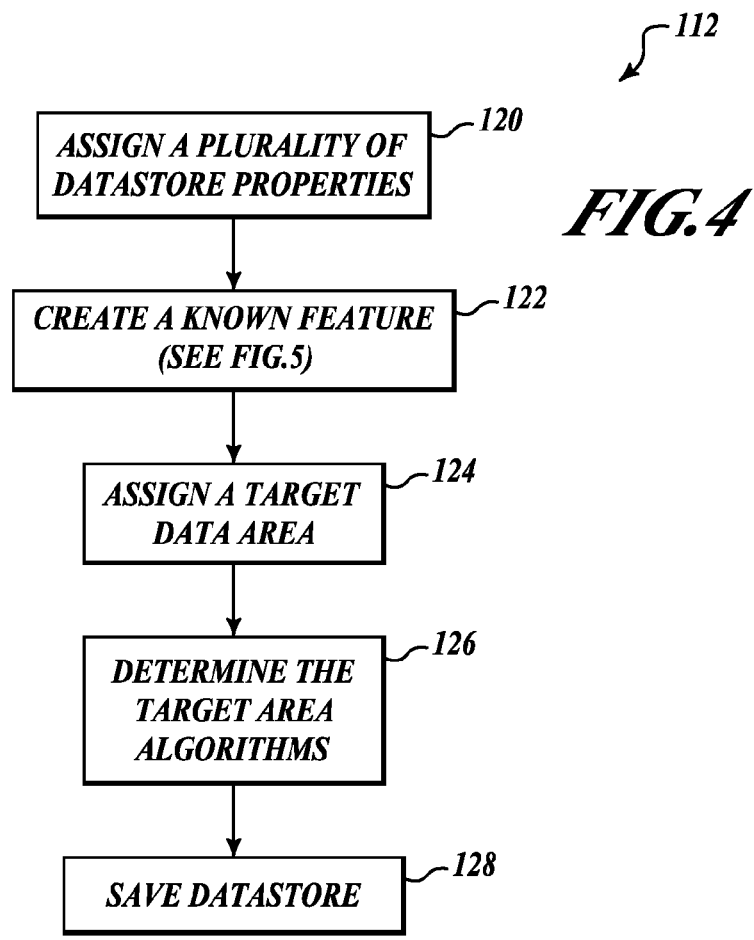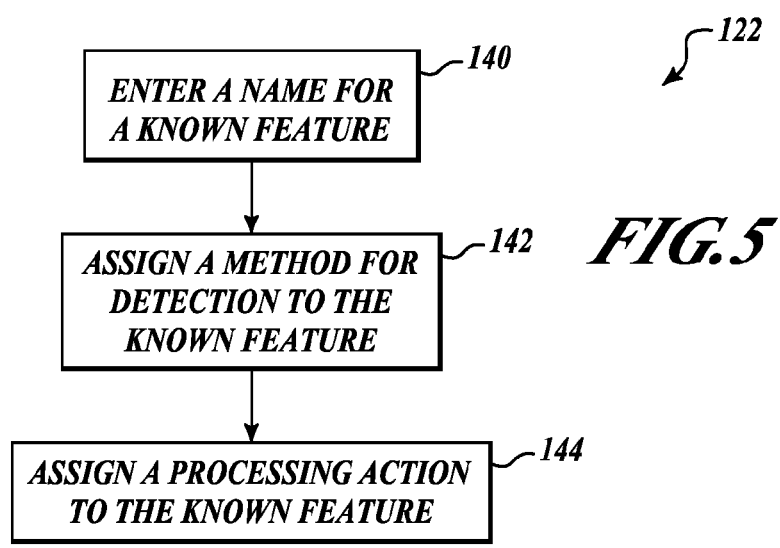

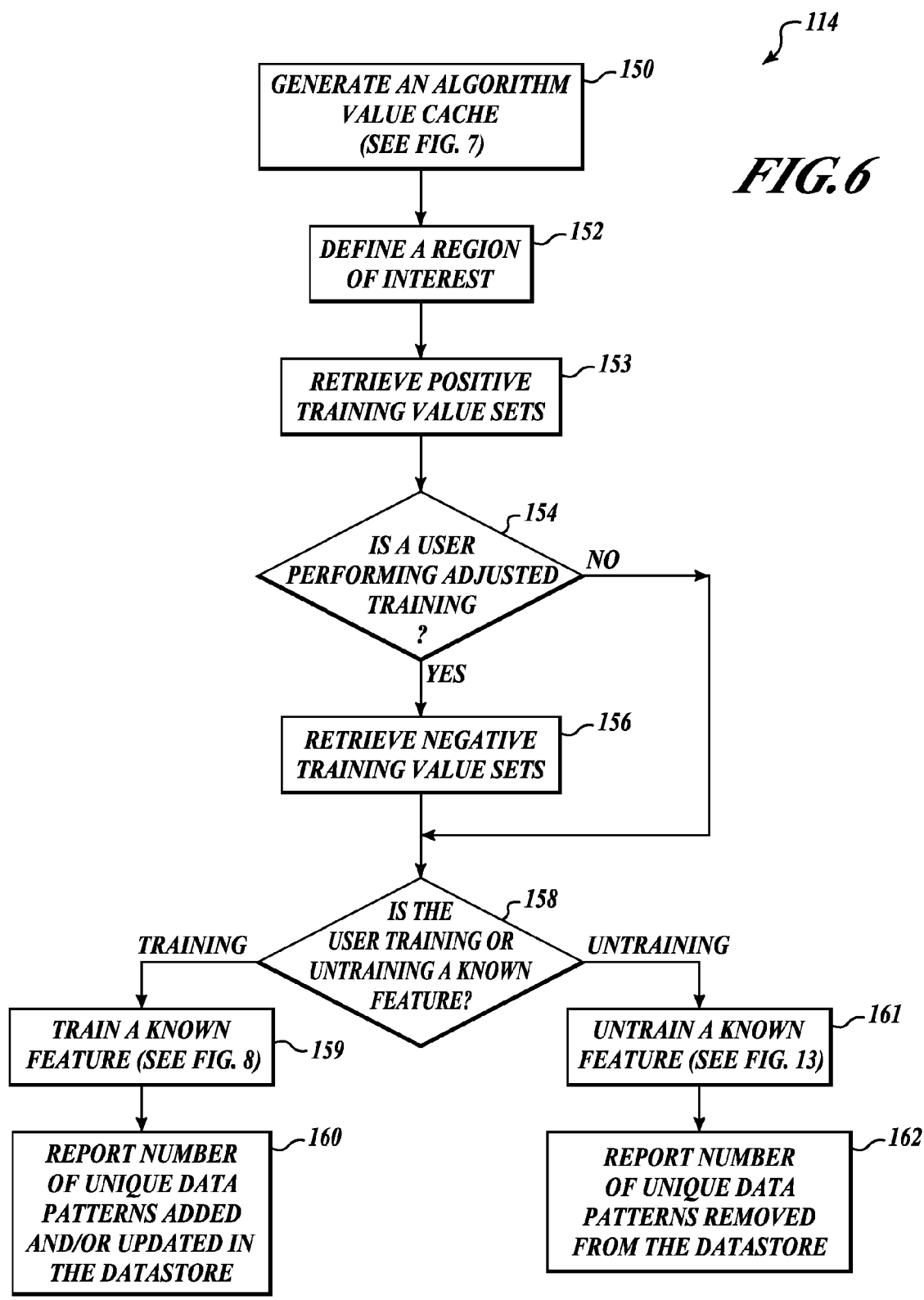

COLUMNS

| | 1 | 2 | 3 | 4 | 5 | 6 | 7 | 8 | 9 | 10 |
|---|---|---|---|---|---|---|---|---|---|---|
| 1 | 5 | 159 | 189 | 59 | 112 | 59 | 5 | 209 | 126 | 131 |
| 2 | 200 | 188 | 120 | 72 | 195 | 134 | 194 | 196 | 254 | 47 |
| 3 | 147 | 222 | 145 | 194 | 216 | 181 | 216 | 97 | 60 | 81 |
| 4 | 103 | 123 | 251 | 152 | 129 | 86 | 161 | 14 | 136 | 175 |
| 5 | 180 | 161 | 39 | 207 | 243 | 134 | 108 | 213 | 147 | 194 |
| 6 | 196 | 14 | 71 | 129 | 103 | 170 | 156 | 145 | 1 | 247 |
| 7 | 141 | 71 | 83 | 203 | 75 | 195 | 237 | 240 | 220 | 67 |
| 8 | 123 | 231 | 252 | 229 | 190 | 22 | 246 | 107 | 169 | 126 |
| 9 | 224 | 72 | 11 | 231 | 96 | 62 | 185 | 249 | 84 | 195 |
| 10 | 248 | 190 | 31 | 13 | 15 | 77 | 131 | 52 | 87 | 127 |

ROWS

*FIG.23*

605 607 COLUMNS

| | | 1 | 2 | 3 | 4 | 5 | 6 | 7 | 8 | 9 | 10 |
|---|---|---|---|---|---|---|---|---|---|---|---|
| ROWS | 1 | | | | | | | | | | |
| | 2 | | 153 | 150 | 145 | 136 | 146 | 143 | 151 | 133 | |
| | 3 | | 167 | 163 | 164 | 151 | 168 | 142 | 148 | 107 | |
| | 4 | | 152 | 166 | 175 | 172 | 164 | 134 | 128 | 113 | |
| | 5 | | 126 | 127 | 147 | 150 | 143 | 132 | 120 | 130 | |
| | 6 | | 106 | 109 | 128 | 162 | 158 | 178 | 163 | 164 | |
| | 7 | | 131 | 143 | 148 | 146 | 155 | 169 | 169 | 147 | |
| | 8 | | 134 | 154 | 152 | 145 | 145 | 171 | 193 | 162 | |
| | 9 | | 154 | 140 | 119 | 104 | 114 | 126 | 146 | 133 | |
| | 10 | | | | | | | | | | |

610 612 COLUMNS

| | | 1 | 2 | 3 | 4 | 5 | 6 | 7 | 8 | 9 | 10 |
|---|---|---|---|---|---|---|---|---|---|---|---|
| ROWS | 1 | | | | | | | | | | |
| | 2 | | 159 | 159 | 145 | 134 | 181 | 181 | 194 | 126 | |
| | 3 | | 147 | 152 | 152 | 152 | 181 | 161 | 161 | 81 | |
| | 4 | | 147 | 161 | 194 | 181 | 161 | 134 | 136 | 97 | |
| | 5 | | 123 | 129 | 129 | 134 | 134 | 145 | 145 | 147 | |
| | 6 | | 83 | 83 | 103 | 170 | 156 | 170 | 156 | 194 | |
| | 7 | | 123 | 129 | 129 | 170 | 170 | 170 | 169 | 145 | |
| | 8 | | 123 | 203 | 190 | 190 | 185 | 195 | 220 | 169 | |
| | 9 | | 190 | 190 | 96 | 77 | 96 | 107 | 131 | 126 | |
| | 10 | | | | | | | | | | |

┌─620
                    622┐
                       └COLUMNS

| ROWS | 1 | 2 | 3 | 4 | 5 | 6 | 7 | 8 | 9 | 10 |
|---|---|---|---|---|---|---|---|---|---|---|
| 1 | | | | | | | | | | |
| 2 | | 217 | 163 | 160 | 160 | 214 | 211 | 249 | 207 | |
| 3 | | 148 | 179 | 179 | 147 | 133 | 202 | 240 | 240 | |
| 4 | | 212 | 212 | 212 | 157 | 157 | 202 | 202 | 199 | |
| 5 | | 237 | 237 | 212 | 157 | 157 | 199 | 212 | 246 | |
| 6 | | 182 | 193 | 204 | 168 | 168 | 132 | 239 | 246 | |
| 7 | | 238 | 238 | 181 | 207 | 224 | 224 | 245 | 246 | |
| 8 | | 241 | 241 | 241 | 209 | 224 | 227 | 165 | 182 | |
| 9 | | 241 | 241 | 241 | 218 | 231 | 227 | 197 | 197 | |
| 10 | | | | | | | | | | |

┌─630
                    632┐
                       └COLUMNS

| ROWS | 1 | 2 | 3 | 4 | 5 | 6 | 7 | 8 | 9 | 10 |
|---|---|---|---|---|---|---|---|---|---|---|
| 1 | | | | | | | | | | |
| 2 | | 64 | 56 | 58 | 64 | 75 | 75 | 83 | 72 | |
| 3 | | 51 | 56 | 55 | 51 | 45 | 66 | 78 | 76 | |
| 4 | | 63 | 63 | 67 | 50 | 54 | 66 | 67 | 65 | |
| 5 | | 78 | 77 | 74 | 50 | 47 | 57 | 70 | 85 | |
| 6 | | 65 | 70 | 72 | 55 | 59 | 47 | 77 | 83 | |
| 7 | | 81 | 88 | 71 | 69 | 75 | 73 | 80 | 82 | |
| 8 | | 85 | 93 | 87 | 80 | 82 | 86 | 62 | 69 | |
| 9 | | 96 | 105 | 106 | 90 | 80 | 84 | 71 | 62 | |
| 10 | | | | | | | | | | |

COLUMNS

| ROWS | 1 | 2 | 3 | 4 | 5 | 6 |
|---|---|---|---|---|---|---|
| 1 | 120 | 72 | 195 | 134 | 194 | 196 |
| 2 | 145 | 194 | 219 | 181 | 216 | 97 |
| 3 | 251 | 152 | 129 | 86 | 161 | 14 |
| 4 | 39 | 207 | 243 | 134 | 108 | 213 |
| 5 | 71 | 129 | 103 | 170 | 156 | 145 |
| 6 | 83 | 203 | 75 | 195 | 237 | 240 |

| ROWS | 1 | 2 | 3 | 4 | 5 | 6 |
|---|---|---|---|---|---|---|
| 1 | | | | | | |
| 2 | | 164 | 151 | 177 | 145 | |
| 3 | | 175 | 172 | 174 | 157 | |
| 4 | | 147 | 152 | 155 | 163 | |
| 5 | | 128 | 164 | 152 | 177 | |
| 6 | | | | | | |

↙ 680

| ROWS | 1 | 2 | 3 | 4 | 5 | 6 |
|---|---|---|---|---|---|---|
| 1 | | | | | | |
| 2 | | 152 | 152 | 194 | 145 | |
| 3 | | 194 | 181 | 181 | 161 | |
| 4 | | 129 | 140 | 156 | 161 | |
| 5 | | 103 | 180 | 156 | 180 | |
| 6 | | | | | | |

↙ 690

| ROWS | 1 | 2 | 3 | 4 | 5 | 6 |
|---|---|---|---|---|---|---|
| 1 | | | | | | |
| 2 | | 179 | 147 | 151 | 223 | |
| 3 | | 212 | 157 | 157 | 130 | |
| 4 | | 212 | 157 | 157 | 127 | |
| 5 | | 204 | 168 | 168 | 132 | |
| 6 | | | | | | |

↙ 700

| ROWS | 1 | 2 | 3 | 4 | 5 | 6 |
|---|---|---|---|---|---|---|
| 1 | | | | | | |
| 2 | | 55 | 51 | 50 | 71 | |
| 3 | | 67 | 50 | 50 | 45 | |
| 4 | | 74 | 50 | 48 | 38 | |
| 5 | | 72 | 55 | 52 | 40 | |
| 6 | | | | | | |

952 — Start | Identification | Training Counts | Cluster Range | Actions | Summary Choose the cluster range values for this known feature. How far in each dimension from where a known feature was identified do you look to find other locations of the same known feature? Press Next to continue.

980 — Dimension: X
982 — Dimension Value: 0
Cluster Count: 1 — 984

Cancel | << Back | Next >> | Finish

FIG.49

952 — Start | Identification | Training Counts | Cluster Range | Actions | Summary Choose the action values for this known feature. The action you select will occur when a known feature is identified within a medium. Press Next to continue.

Action: No Action
990 — No Action
System Sounds
Paint

Cancel | << Back | Next >> | Finish

METHODS AND SYSTEMS FOR DATA ANALYSIS AND FEATURE RECOGNITION INCLUDING DETECTION OF AVIAN INFLUENZA VIRUS

PRIORITY CLAIM

This application claims the benefit of Provisional Patent Application Ser. Nos. 60/743,711 filed on Mar. 23, 2006 and 60/773,377 filed on Feb. 14, 2006 all of which are incorporated herein by reference in their entirety.

FIELD OF THE INVENTION

The present invention, in various embodiments, relates generally to the field of data analysis, and more particularly to pattern and object recognition in digital data.

BACKGROUND OF THE INVENTION

With the increasing use of computers and computerized technology, the amount of information represented digitally has become enormous. Analysis of these vast quantities of digital data generally involves the recognition of known patterns.

In many cases, information that originates in a digital form is ultimately analyzed through manual review by a person, often requiring substantial training. For example, medical image analysis typically requires a high level of expertise. In order for people to interact with the volumes of digital data, the information is typically converted into a visual, audible, or other human-perceivable representation. However, during the process of translating digital data from its raw form into a convenient output form, some information can be lost. Data is often processed and filtered for presentation before analysis, losing significant information from the original data. For example, the data of ultrasound, seismic, and sonar signals are all initially based on sound. The data of each of these is typically processed into a graphical form for display, but the processing often sacrifices substantial meaning and detail for the sake of human readability.

While humans can be trained to analyze many different types of data, manual human analysis is generally more expensive than automated systems. Additionally, errors are often introduced due to the limits of human perception and attention span. The data often contains more detail than human senses can discern, and it is well-known that repetition causes errors.

To address these shortcomings of human analysis, many automated pattern recognition systems have been developed. However, most of these solutions are highly data-specific. The inputs that a pattern recognition system can handle are often fixed and limited by design. Many systems are inherently limited by design on the basis that many systems are designed by use on a specific modality. For example, medical image analysis systems perform well on X-ray or MR imagery but perform poorly on seismic data. The reverse is also true. The system by which the data is evaluated is tightly coupled with the specific data source it was designed to evaluate. Therefore, improvements across a broad range of systems are very difficult.

Within each system, pattern and feature recognition is processing-intensive. For example, image analysis commonly uses complex algorithms to find shapes, requiring thousands of algorithms to be processed. The time to discover, develop, and implement each algorithm causes an incremental delay in deploying or improving the system.

Thus, there still remains substantial room for improvement in the field of automated pattern recognition systems.

Additionally, most experts predict that under conventional practices, avian influenza will not be able to be detected rapidly enough to prevent a flu pandemic that could hit the world within the next few years. Currently, there is not a rapid screening method for birds, other animals, or humans. In the event of a pandemic, current methods would require vast amounts of pathology skilled manpower to examine blood or other fluid samples in order to detect and track the Avian Flu. The amount of pathology skilled manpower could not be attained.

Therefore there is a need for an automatic avian influenza virus detection system and method.

SUMMARY OF THE INVENTION

This system is designed not to be limited by any specific modality or by the limited knowledge of those developing the system. The present invention provides an automated pattern recognition and object detection system that can be rapidly developed and improved using a minimal number of algorithms for the data content to fully discriminate details in the data, while reducing the need for human analysis. The present invention includes a data analysis system that recognizes patterns and detects objects in data without requiring adaptation of the system to a particular application, environment, or data content. The system evaluates the data in its native form independent of the form of presentation or the form of the post-processed data.

In one aspect of the present invention, the system analyzes data from any and all modalities within all data types. Example data modalities include imagery, acoustic, scent, tactile, and as yet undiscovered modalities. Within imagery, there exists still and moving images with applications in the fields of medicine, homeland security, natural resources, agriculture, food sciences, meteorology, space, military, digital rights management, and others. Within acoustic, there exists single and multi-channel audio sound, ultrasound-continuous stream, seismic, and SONAR with applications in the fields of medicine, homeland security, military, natural resources, geology, space, digital rights management, and others. Examples of other digital data streams include radar, scent, tactile, financial market and statistical data, mechanical pressure, environmental data, taste, harmonics, chemical analysis, electrical impulses, text, and others. Some data modalities may be combinations of other modalities, such as video with sound or multiple forms of a single modality such as where multiple images of different types are taken of the same sample, for example correlated MRI and CT imaging; combined SAR, photograph and IR imagery. Improvements made in the common system benefit all modalities.

In other aspects of the present invention, the system uses a relatively small number of simple algorithms that capture more fundamental relationships between data elements to identify features and objects within the data. This limited set of algorithms can be implemented quickly in each modality and in multiple modalities.

In still other aspects of the present invention, the system provides an automated system that operates on the full resolution of the native data. The results are produced in a timely manner, alleviating the tedium of preliminary human analysis and alerting the operator to examine a data set that requires attention.

In additional aspects of the present invention, a method includes receiving a first data set corresponding to a first aspect of a first biological sample, analyzing the first data set using results of a first series of algorithms processed on a second data set corresponding to an aspect of a second biological sample known to contain avian influenza virus, generating an algorithm value cache for the first data set by running a second series of algorithms on the first data set, generating a match result by comparing the algorithm value cache with the results of the first series of algorithms, and performing a processing action based on the generated match result.

In yet other aspects of the present invention, the system includes a system for data analysis and detection of avian influenza virus in a biological sample.

DESCRIPTION OF THE DRAWINGS

The preferred and alternative embodiments of the present invention are described in detail below with reference to the following drawings.

FIG. 4 shows an example method for creating a datastore;

FIG. 5 shows an example method for creating a known feature;

FIG. 6 shows an example method for modifying a synaptic web by training or untraining;

FIG. 23 shows an example 10×10 pixel array of grey scale image data;

FIG. 24 shows an example 10×10 array containing the outputs of the mean algorithm;

FIG. 25 shows an example 10×10 array containing the outputs of the median algorithm;

FIG. 26 shows an example 10×10 array containing the outputs of the spread of values algorithm;

FIG. 27 shows an example 10×10 array containing the outputs of the standard deviation algorithm;

FIG. 34 shows a series of arrays for a 6×6 grey scale image;

FIG. 48 shows a screenshot of the cluster range values for a known feature;

FIG. 49 shows a screenshot of the action value of a known feature;

Figure 1:
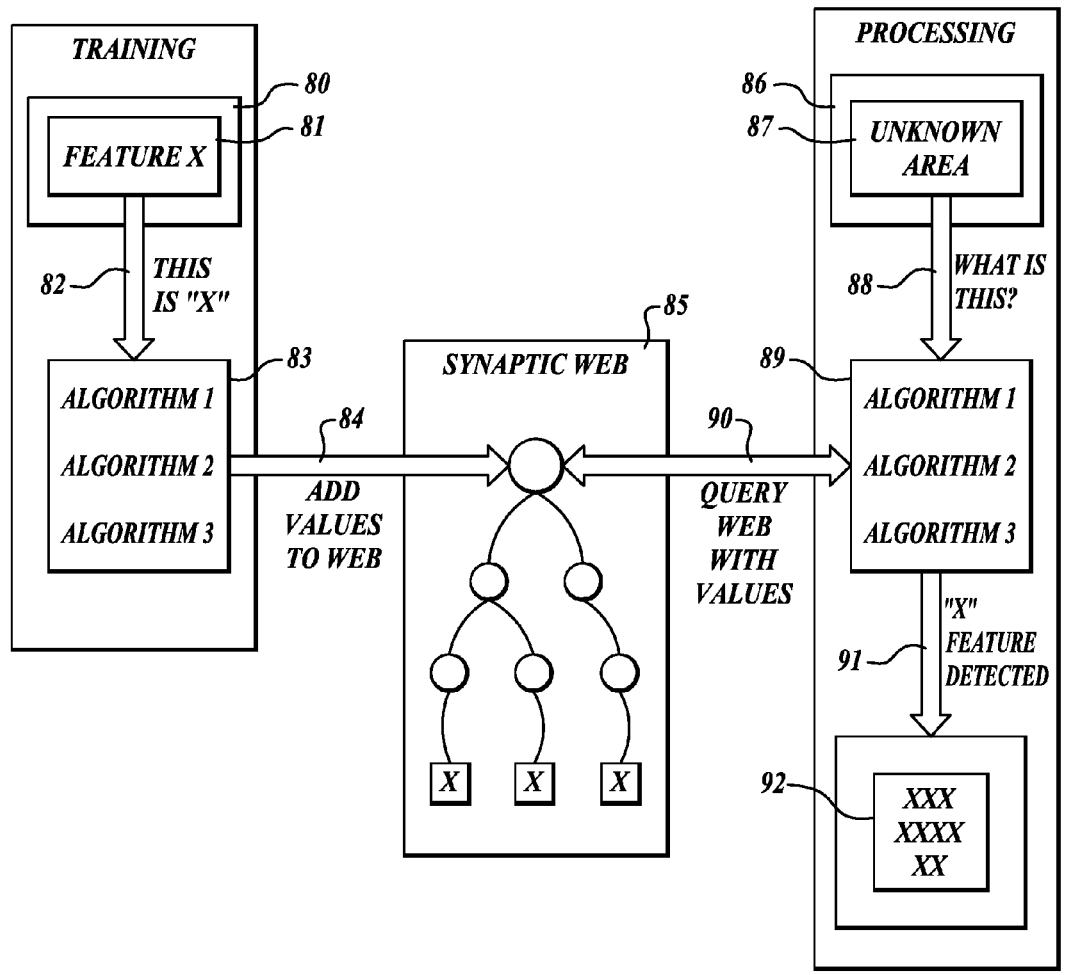
FIG. 1 shows an overview of one embodiment of the invention.

As used herein, a "training event" is the process of associating a plurality of algorithm values to a known feature by creating or updating synaptic paths and synaptic leaves.

As used herein, the term "algorithm" carries its normal meaning, and refers without limitation to any series of repeatable steps resulting in a discrete "value." For example, an algorithm includes any mathematical calculation. In several embodiments, various algorithms are performed on target data elements in relation to a previously defined target data area to produce a single, meaningful value.

As used herein, the term "hit detection" refers to a method for determining whether a known feature is present in a test data set based on matching a synaptic path encountered during processing with any path trained for the known feature.

As used herein, the term "cluster detection" refers to a method of determining whether a known feature is present in a test data set based on both hit detection and the detection of a specified number of additional hits within a pre-defined "cluster distance" of a target data element.

As used herein, the term "cluster distance" refers to one or more user-defined distance specifications for evaluation of a target data element. A cluster distance may refer to an actual physical distance, or may represent a mathematical relationship between discrete data elements.

As used herein, the term "threshold detection" refers to a method for determining whether a known feature is present in a test data set based on both hit detection and the number of times the synaptic path used in hit detection has been trained as the known feature.

As used herein, the term "positive training value sets" refers to the sets of algorithm values that were in the area of data trained as the user defined known feature.

As used herein, the term "negative training value sets" refers to the sets of algorithm values that were outside the area of data trained as the user defined known feature.

As used herein, the term "area training" refers to a process used in a training event where each set of algorithm values found in a positive training value set is used to generate synaptic paths for the known feature.

As used herein, the term "relative adjusted training" refers to a process used in a training event where each set of algorithm values found in a negative training value set nullifies one matching set of algorithm values found inside the positive training value set. The remaining positive training value sets can then be used to generate synaptic paths for the known feature.

As used herein, the term "absolute adjusted training" refers to a process used in a training event where each set of algorithm values found in a negative training value set nullifies all matching sets of algorithm values found inside the positive training value set. The remaining positive training value sets can then be used to generate synaptic paths for the known feature.

As used herein, the term "modality" is used in its normal sense and generally refers to one of the various different forms or formats of digital data that can be processed. For example, image data represents one modality, while audio data represents another modality. In addition to describing data types that conform to one or more human sensory modalities, the term is also intended to encompass data types and formats that might have little or no relation to the human senses. For example, financial data, demographic data and literary data also represent modalities within the meaning of the term as used herein.

As used herein, the term "submodality" refers to a sub-classification of a modality. In some embodiments, a submodality refers to one of the applications or sources for the data that can affect how the data is processed. For example, X-Ray and Satellite Photography are submodalities of imaging. Systems for producing X-Ray images from different vendors (such as GENERAL ELECTRIC or SIEMENS) can differ enough in their data formats to be described as different submodalities.

Figure 2:
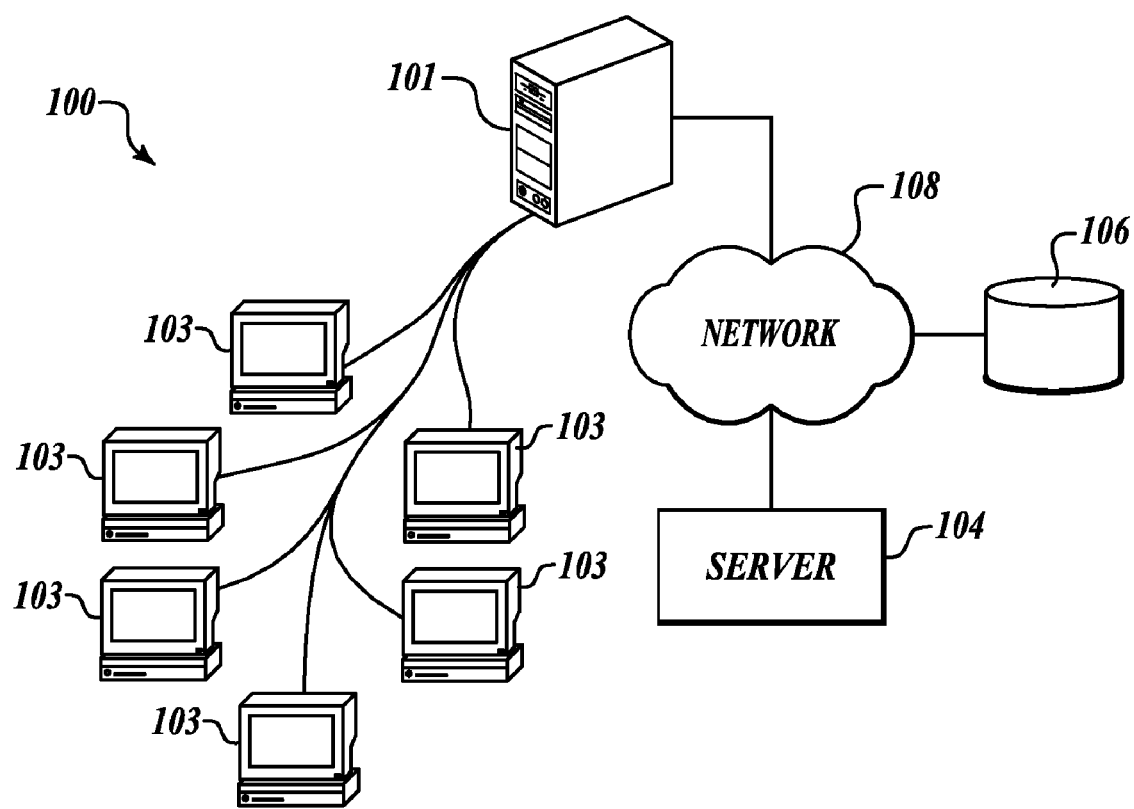
FIG. 2 shows an example system for executing a data analysis and feature recognition system.

FIG. 2 shows an example system 100 for executing a Data Analysis and Feature Recognition System. In one embodiment the system 100 includes a single computer 101. In an alternate embodiment the system 100 includes a computer 101 in communication with a plurality of other computers 103. In an alternate embodiment the computer 101 is connected with a plurality of computers 103, a server 104, a datastore 106, and/or a network 108, such as an intranet or the Internet. In yet another alternate embodiment a bank of servers, a wireless device, a cellular phone and/or another data entry device can be used in place of the computer 101. In one embodiment, a datastore 106 stores a data analysis and feature recognition datastore. The datastore can be stored locally at the computer 101 or at any remote locations while being retrievable by the computer 101. In one embodiment, an application program is run by the server 104 or by the computer 101, which then creates the datastore. The computer 101 or server 104 can include an application program that trains a known feature. For example, the computer 101 or the server 104 can include an application program that identifies a previously defined known feature in a digital media. In one embodiment, the media is one or more pixels in image data or one or more samples in a sound recording.

Figure 3:
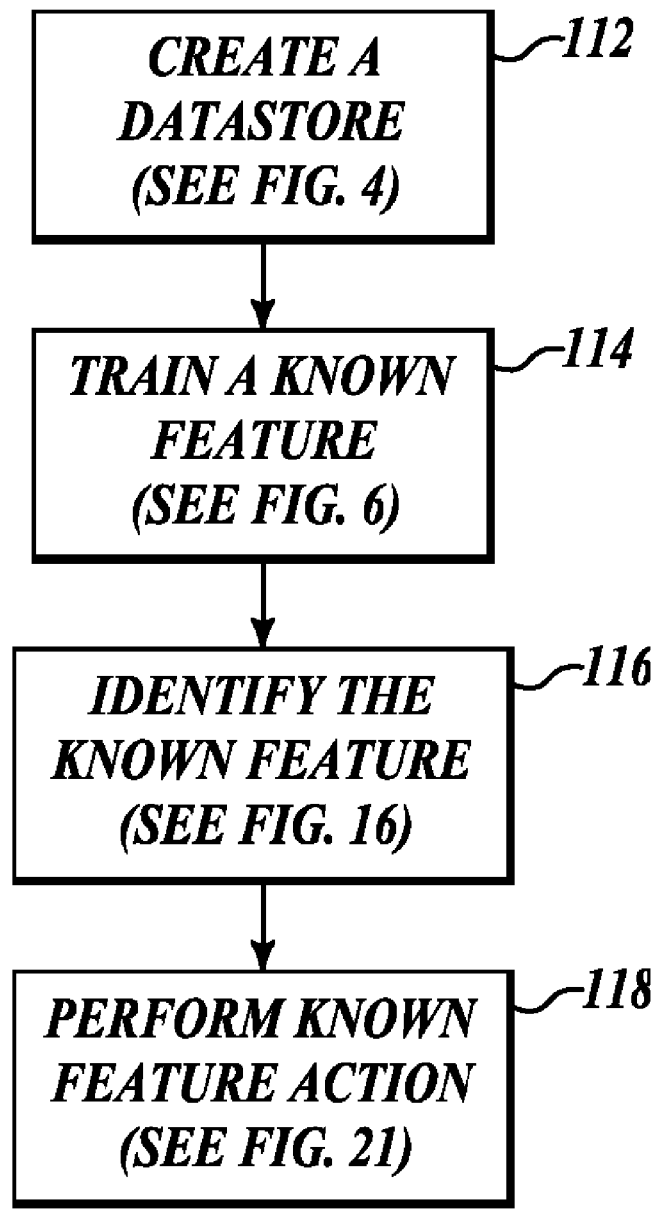
FIG. 3 shows an example method for using a data analysis and feature recognition system.

FIG. 3 shows a method formed in accordance with an embodiment of the present invention. At block 112 a datastore is created, which will be described in more detail below in FIGS. 4 and 5. In block 114 a known feature is trained. Training is described in more detail below with respect to FIGS. 6-15. At block 116 a known feature is identified, which will be described in more detail in FIG. 16-20. At block 118, a known feature action is performed, which is further illustrated in FIG. 20.

FIG. 4 shows an example method (block 112) for creating the datastore. The method (block 112) begins at block 120 by assigning a plurality of datastore properties. In one embodiment, the datastore properties include modality and submodality. Within each modality, there is a plurality of submodalities. In one embodiment, at block 122 a known feature is created, which is further illustrated in FIG. 5. In one embodiment, at block 124 a target data area is assigned. In one embodiment, a target data area is selected. One example target data area for an imaging modality is a pattern of near and far neighboring pixels surrounding a target pixel. In one embodiment, at block 126 target data area algorithms are selected. At block 128 the datastore 106 is saved to the computer 101 or the network 108. Blocks 120, 122, and the combination of 124 and 126 can be executed in any order.

FIG. 5 shows an example method (block 122) for creating a known feature. At block 140 the user enters a name for a known feature. In one embodiment, at block 142 the user assigns a method for detection to the known feature. In one embodiment, the method of detection can be selected as hit detection. In one embodiment, cluster detection can be used. In one embodiment, threshold detection can be used. In one embodiment, cluster and threshold detection can be used. In one embodiment, at block 144, a processing action can be chosen for the method of notification that the known feature was found. In one embodiment, the user may select no action, playing a system sound, or painting a plurality of pixels. Blocks 140, 142 and 144 can be executed in any order.

FIG. 6 shows an example method (block 114) for modifying a synaptic web by training or untraining. In one embodiment, the method begins at block 150 with generating an algorithm value cache, which is further described in FIG. 7. In one embodiment, the method begins at block 152 when an area of data is selected by the user that is known to contain the feature to be trained. At block 153, the positive training value sets are retrieved. In one embodiment, at block 154 a decision is made as to whether a user is performing adjusted training. If YES, at block 156 the negative training value sets are retrieved. In one embodiment, a decision is made at block 158 whether the user is training or untraining a known feature. If TRAINING, then at block 159, the known feature is trained, which is further illustrated in FIG. 8. In one embodiment, at block 160 a report is given to the user showing the number of unique synaptic paths added and updated. If UNTRAINING, then a known feature is untrained, which is further explained in FIG. 13. In one embodiment, at block 162 the number of unique synaptic paths removed is reported to the user. Blocks 150 and 152 can be executed in any order. Blocks 153 and the combination of 154 and 156 can be executed in any order.

In some circumstances, limitations in the ability of the user to finely tune a region of interest may cause some of the positive training value sets to actually contain parts of the data that the user knows to not be what he/she wishes to train. These cases are handled by adjusted training, which can be selected by the user. This area outside the region of interest, in a still image, is usually the background or normal area that the user does not want to train as the known feature. By identifying the negative training value sets, those sets of algorithm values from within the region of interest (the positive training value sets) that actually are not the feature the user wishes to train as the known feature can be removed.

Figure 7:
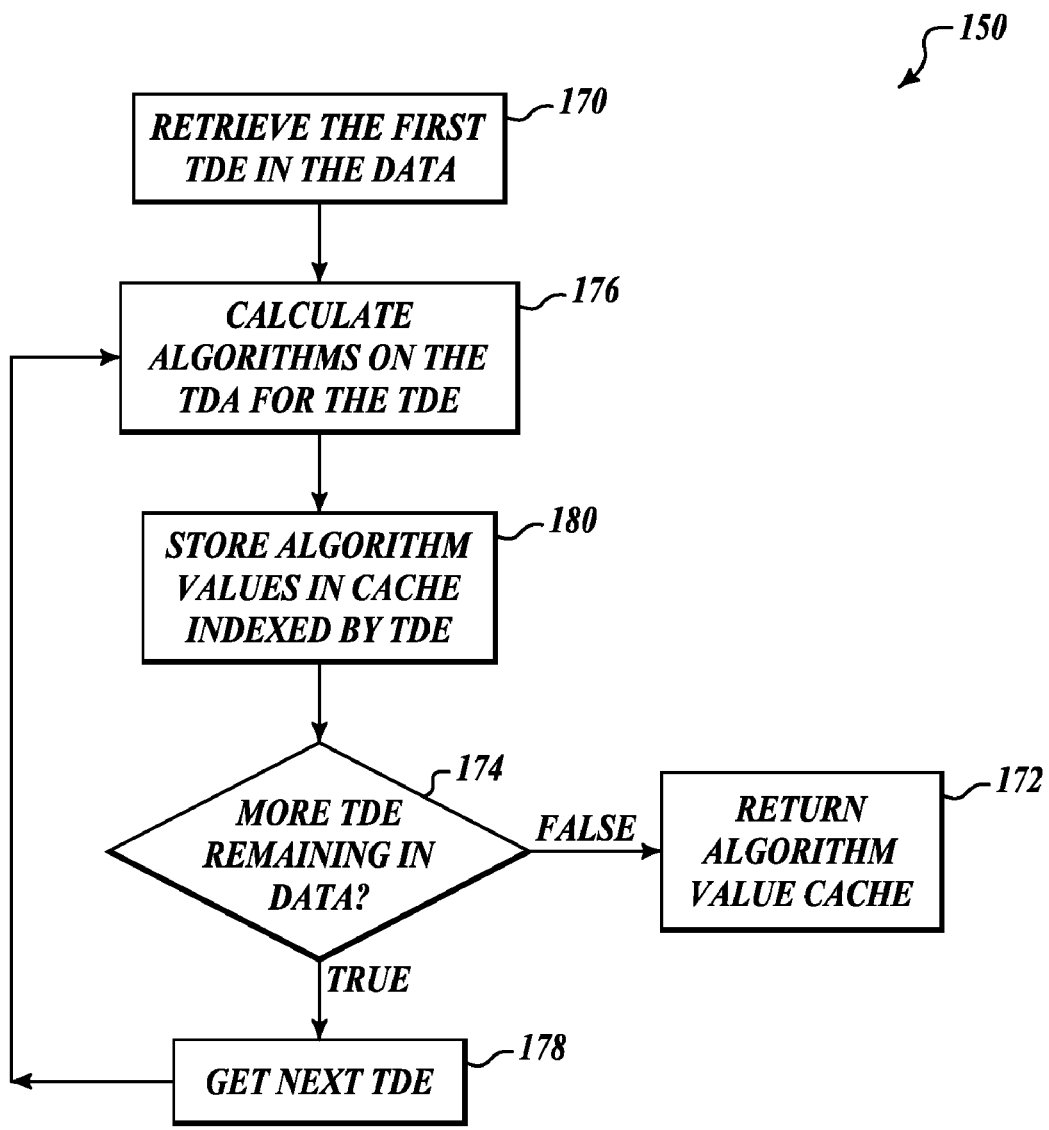
FIG. 7 shows an example method for generating an algorithm value cache.

FIG. 7 shows an example method (block 150) for generating an algorithm value cache. In one embodiment, an algorithm value cache consists of an array storing the numerical results of the previously selected algorithms. The method (block 150) begins at block 170 with the method retrieving the first TDE in the data. At block 176, algorithm values are calculated on the TDA for the TDE. At block 180 the algorithm values are stored in an algorithm value cache for the TDE. At block 174 a decision is made whether more TDEs are available in the data. If FALSE, at block 172, the algorithm cache is completed. If TRUE, at block 178 the next TDE is retrieved and processing returns to block 176.

Figure 8:
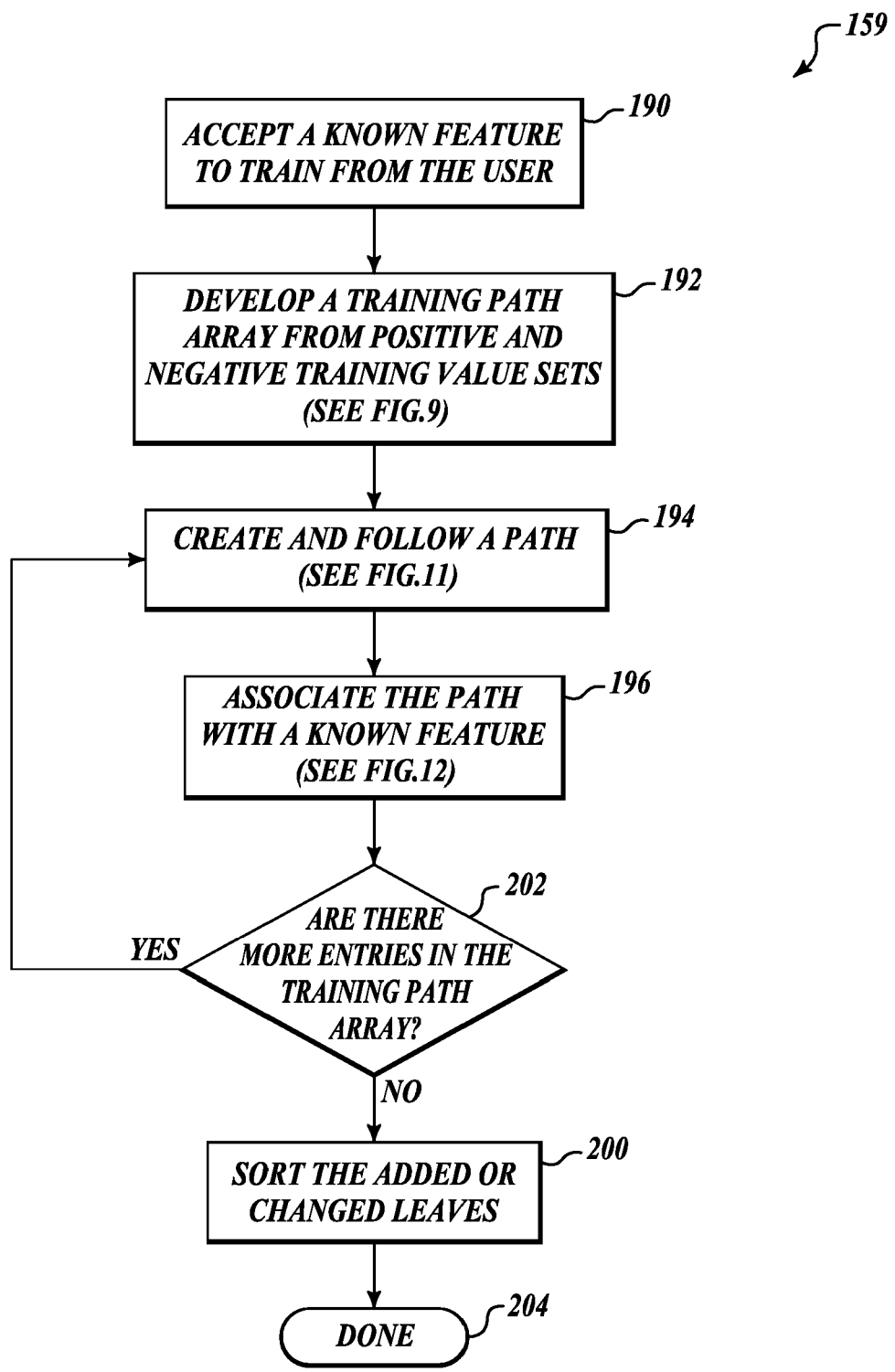
FIG. 8 shows an example method for training a known feature.

FIG. 8 shows an example method 159 for training a known feature. The method 159 begins at block 190 where a known feature is retrieved for training and a training synaptic path array is established. At block 192 the training synaptic path array is developed from positive and negative training value sets. At block 194 a new synaptic path is created and followed. At block 196 the synaptic path is associated with a known feature which is further explained in FIG. 12. At block 202, a decision is made as to whether there are more entries in the training path array. If YES, then return to block 194. If NO, then in one embodiment the training counts are updated. In one embodiment, at block 200 the synaptic leaves are sorted. At block 204 the method (block 159) is completed. Blocks 190 and 192 can be executed in any order.

Figure 9:
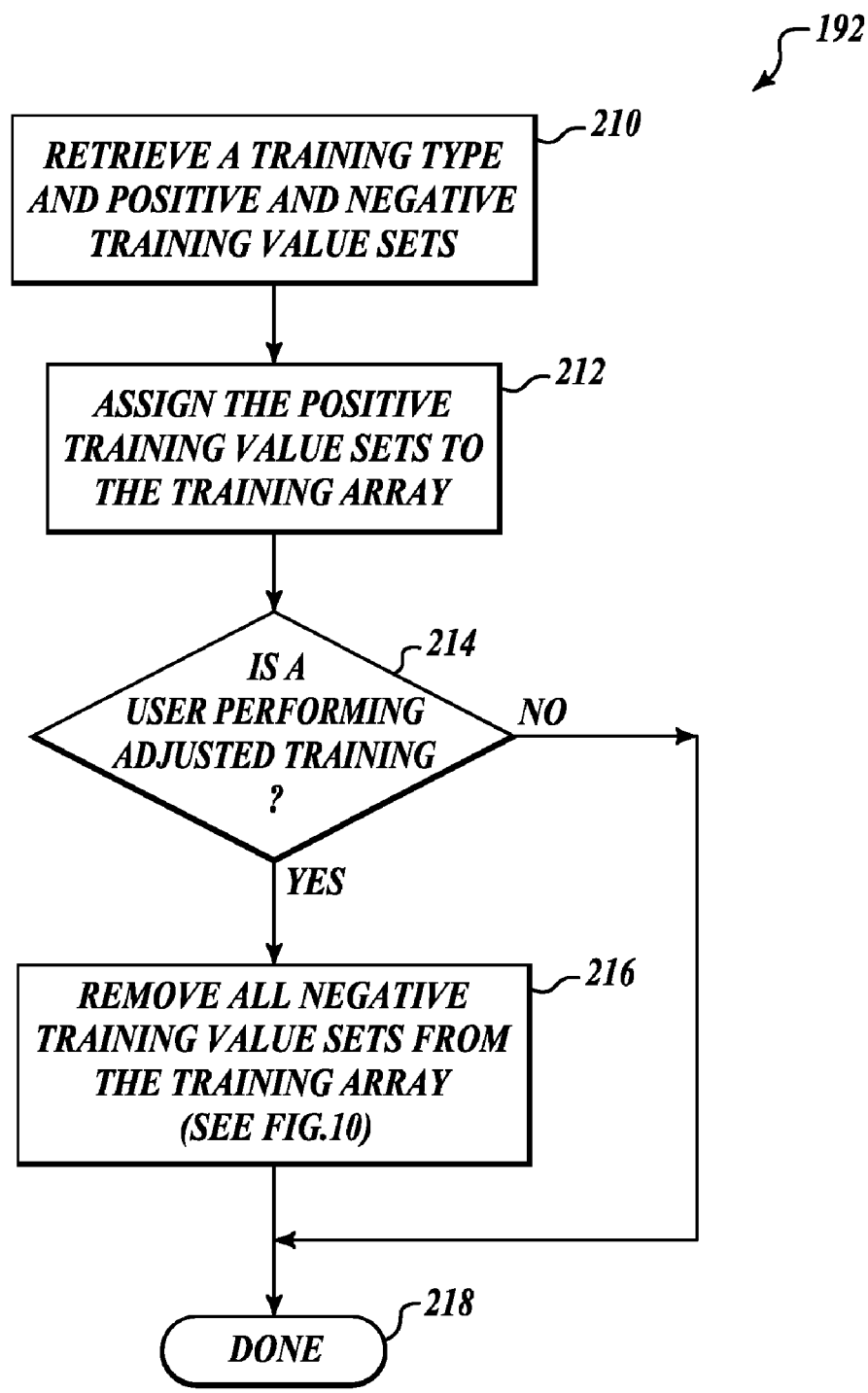
FIG. 9 shows an example method for creating a collection of training paths from positive and negative training value sets.

FIG. 9 shows an example method (block 192) for developing a training synaptic path array from positive and negative training value sets. At block 210, a training type and positive and negative training value sets are retrieved. At block 212, the positive value sets are assigned to the training array. At block 214, a decision is made as to whether the user is performing adjusted training. If YES, then at block 216, the negative training value sets are removed from the training array which is further explained in FIG. 10. At block 218, developing the training synaptic path is complete.

Figure 10:
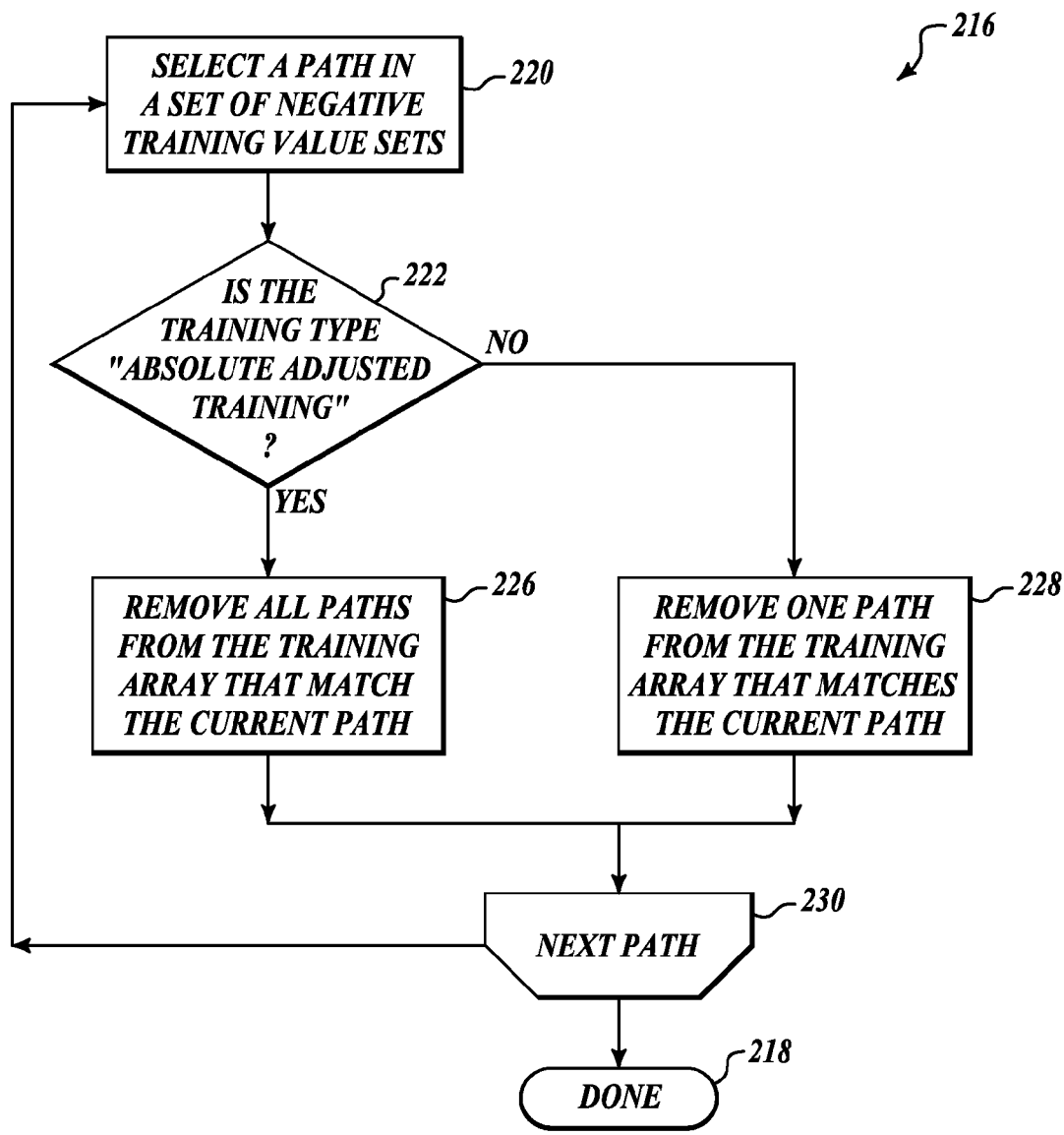
FIG. 10 shows an example method for removing negative training values sets from the collection of training paths.

FIG. 10 shows an example method (block 216) for performing adjusted training. In one embodiment, relative and/or absolute adjusted training are available. At block 220, a synaptic path is selected in a set of negative training value sets. At block 222, a decision is made whether the training type is absolute adjusted training. If YES, then at block 226 all synaptic paths from the training array that match the current synaptic path are removed. If NO, then at block 228, remove one synaptic path from the training array that matches the current synaptic path. At block 230, a next synaptic path is selected, and if there are no further synaptic paths, then at block 218, the method returns to FIG. 9, block 216.

Figure 11:
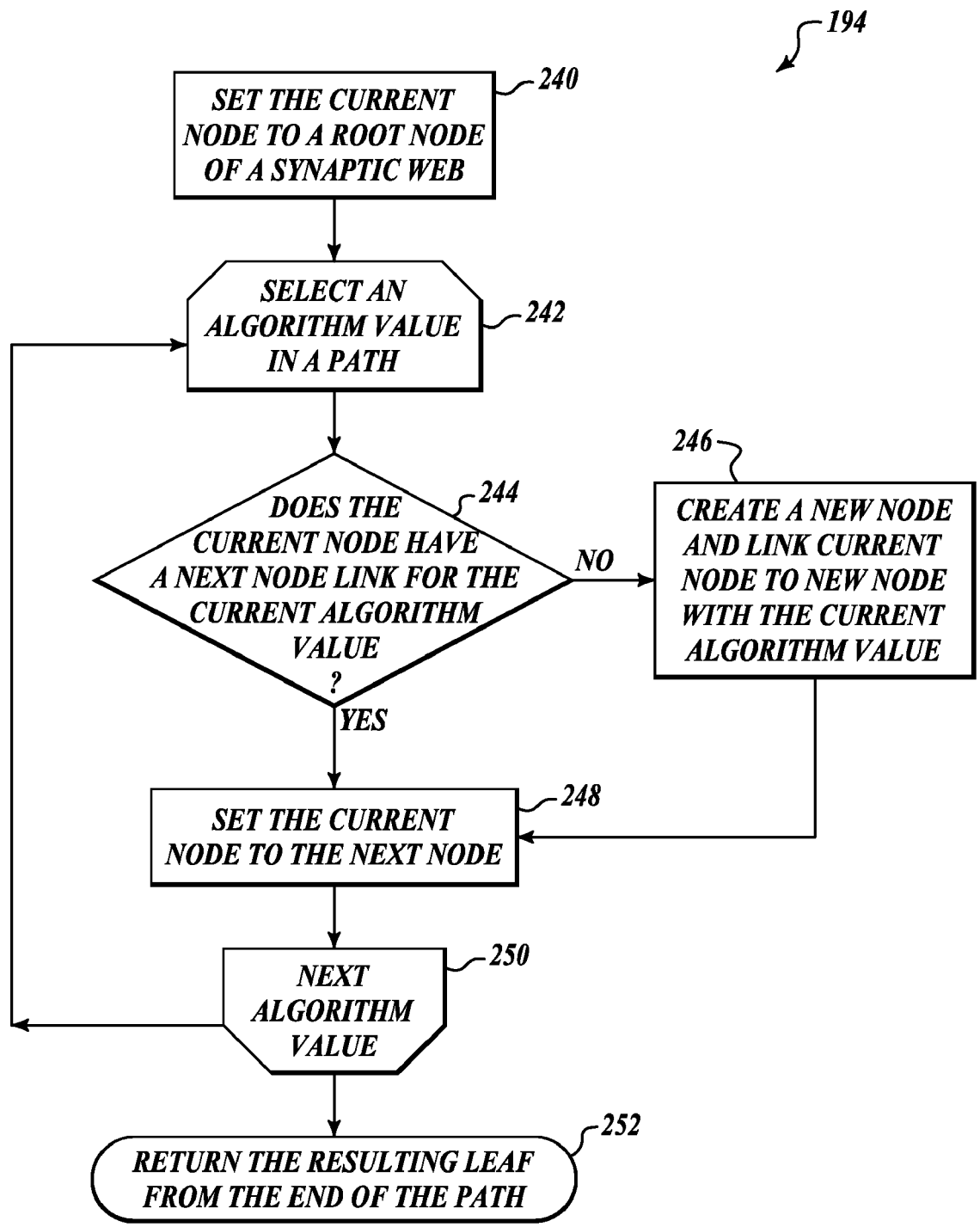
FIG. 11 shows an example method for creating a synaptic path from a training path.

FIG. 11 shows an example method (block 194) for creating and following a synaptic path. At block 240, the process sets the current node to a root node of a synaptic web. At block 242, an algorithm value in a synaptic path is selected. At block 244, a decision is made as to whether the current node has a next node link for the current algorithm value. If YES, then the current node is set to the next node at block 248. If NO, then at block 246 a new node is created; the current node is linked to the new node with the current algorithm value. At block 248 the current node is set to the next node. At block 250 the next algorithm value is selected. At block 252 a resulting synaptic leaf is returned to block 194 in FIG. 8.

Figure 12:
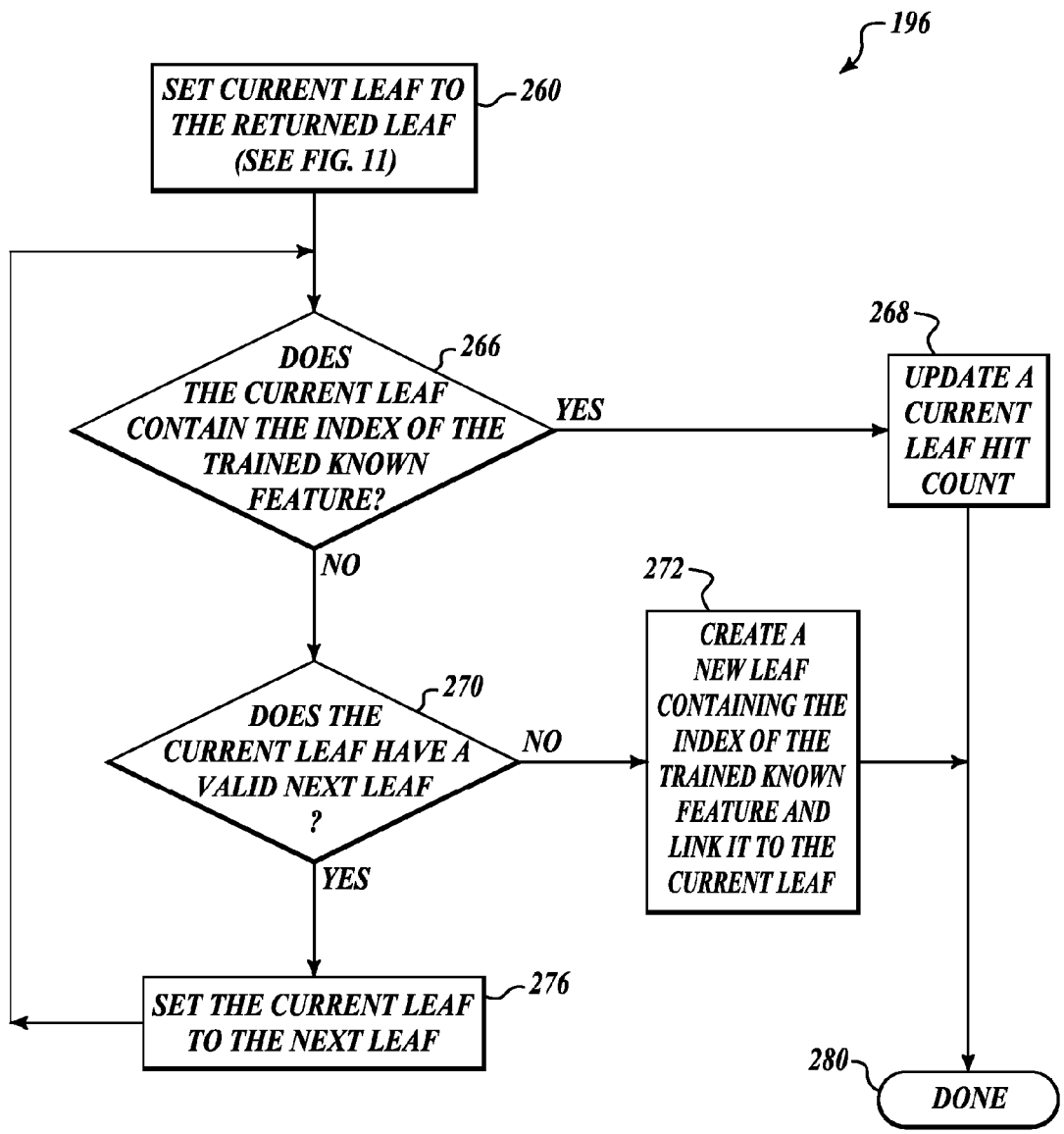
FIG. 12 shows an example method for associating a synaptic leaf with a known feature.

FIG. 12 shows an example method (block 196) for associating the synaptic path with a known feature. At block 260, a current synaptic leaf is set to the synaptic leaf returned from FIG. 11 to block 194 in FIG. 7. At block 266 a decision is made as to whether the current synaptic leaf contains the index value of the trained known feature. If YES, then at block 268 the current synaptic leaf hit count is updated. If NO, then at block 270 the decision is made as to whether the current synaptic leaf has a next synaptic leaf. If YES, then the current synaptic leaf is set to the next synaptic leaf at block 276. If NO, then at block 272 a new synaptic leaf is created containing the index of the trained known feature, and it is linked to the current synaptic leaf. At block 280 the process returns to block 196 in FIG. 7.

Figure 13:
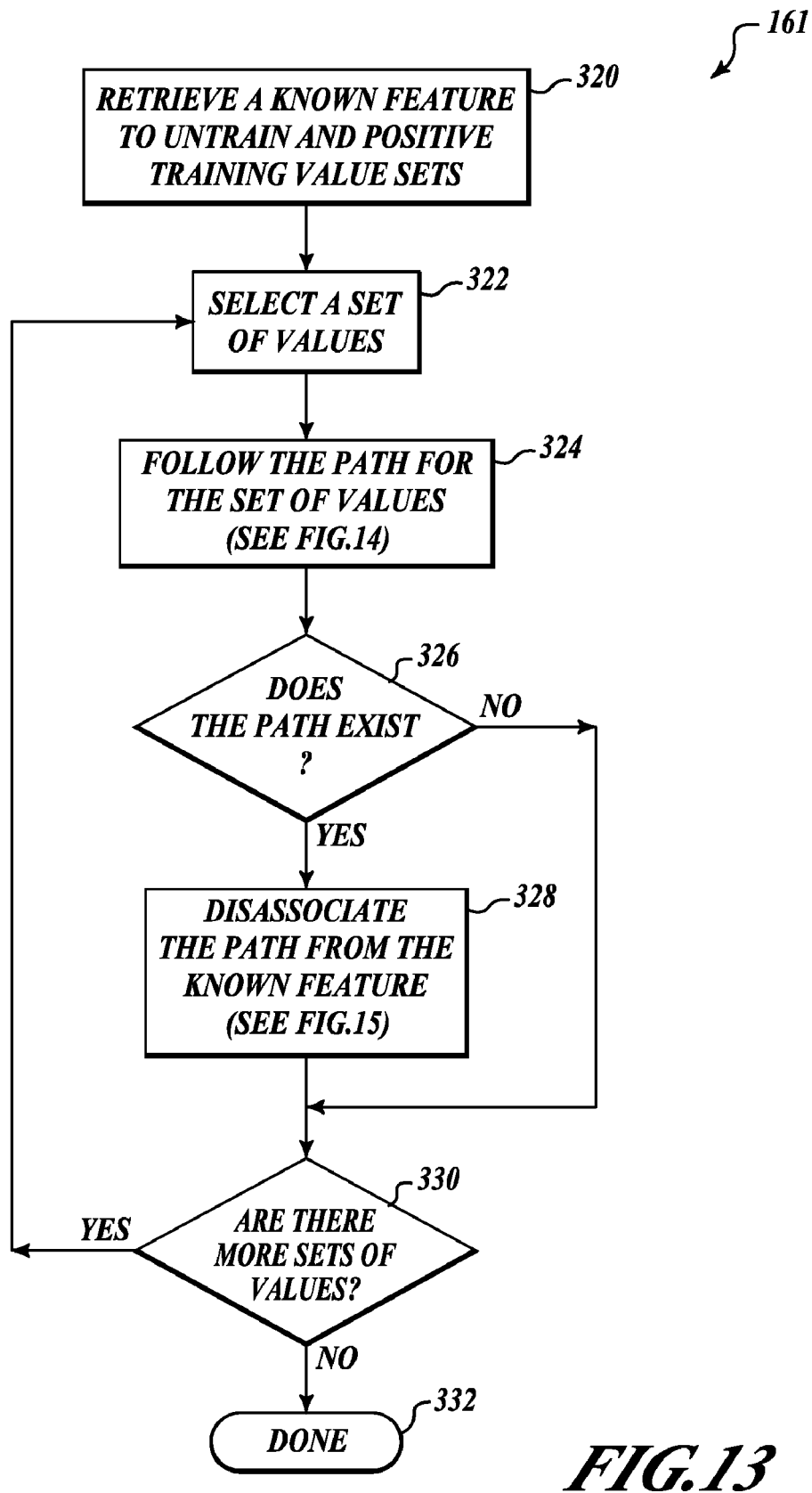
FIG. 13 shows an example method for untraining a known feature.

FIG. 13 shows an example method (block 161) for untraining a known feature. At block 320 a known feature to untrain and a plurality of positive training value sets are retrieved. At block 322 the current set of values is selected. At block 324 the synaptic path is followed for the current positive training value set. At block 326 the synaptic path is tested see whether it exists. If YES, then the synaptic path is disassociated from a known feature at block 328. If NO, then at block 330 go to the next set of positive training values. Once all positive training value sets have been evaluated, then at block 332 return to block 161 in FIG. 6.

Figure 14:
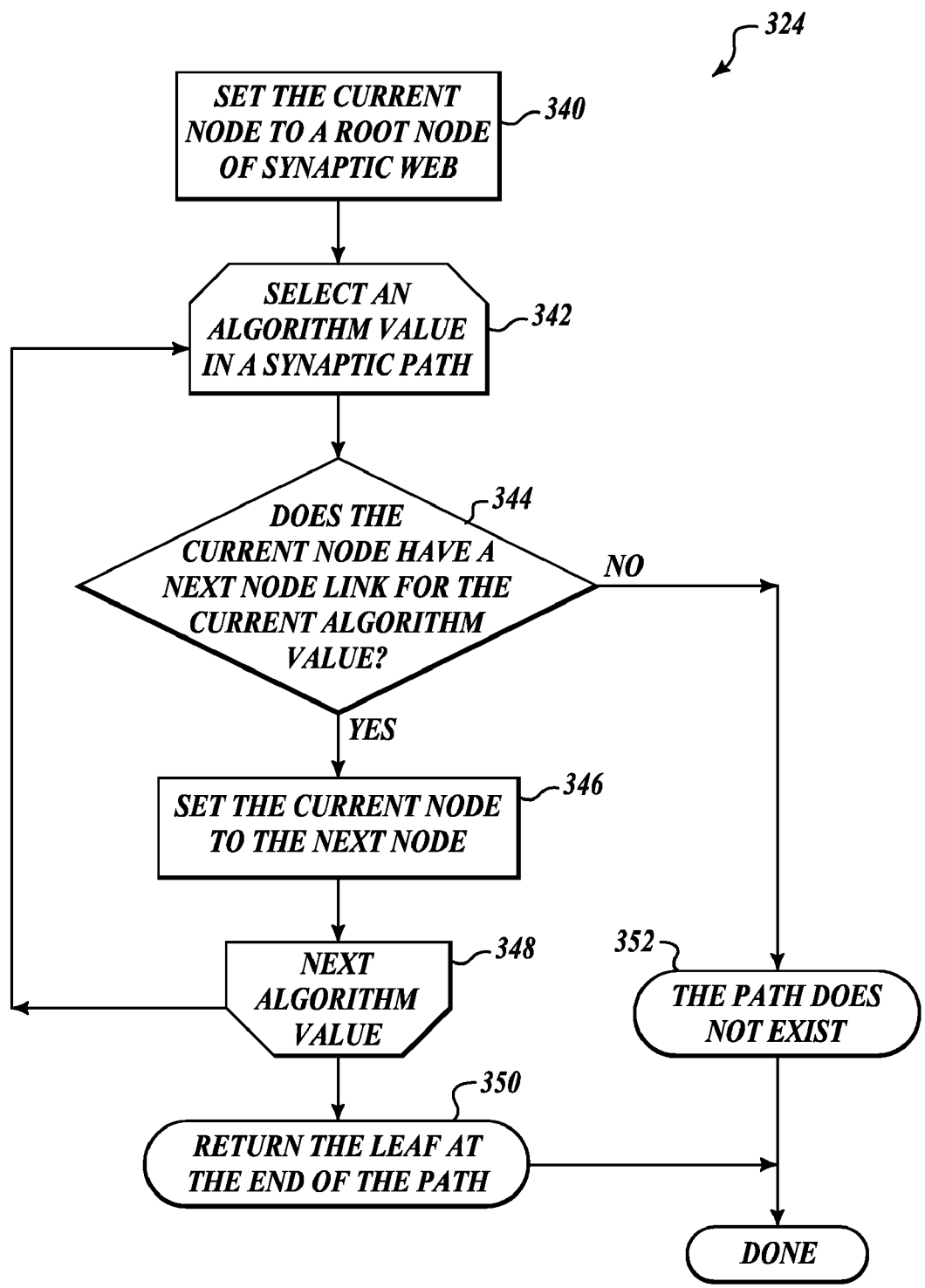
FIG. 14 shows an example method for using a set of algorithm values to retrieve a synaptic leaf in the synaptic web.

FIG. 14 shows an example method (block 324) for following a synaptic path to identify a leaf based on a set of algorithm values. At block 340 a current node is set to a root node of a synaptic web. At block 342 an algorithm value is selected from the synaptic path for the algorithm for the current node. At block 344 a decision is made as to whether the current node has a next node link for the current algorithm value. If YES, then at block 346 the current node is set to the next node. At block 348 a next algorithm value is selected. If there are no further algorithm values, then at block 350 the synaptic leaf is returned at the end of the synaptic path. If NO, then at block 352 the synaptic path does not exist. The process returns to block 324 in FIG. 13.

Figure 15:
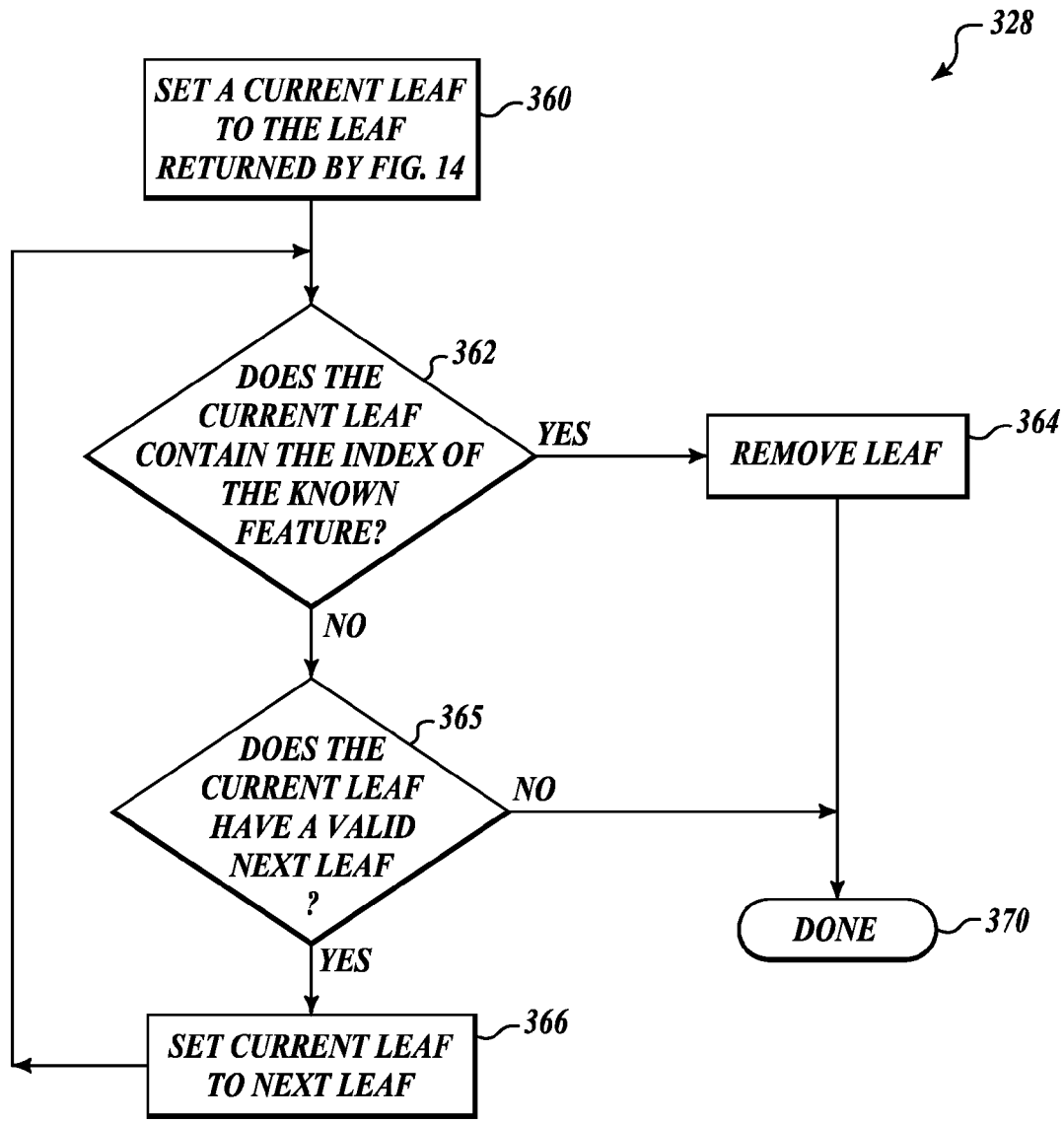
FIG. 15 shows an example method for disassociating a synaptic leaf from a known feature.

FIG. 15 shows an example method (block 328) for dissociating a synaptic path from a known feature. At block 360 a current synaptic leaf is set to the leaf returned by FIG. 14 to block 324. A decision is made at block 362 as to whether the current leaf contains the index of the known feature. If YES, then the leaf is removed at block 364. If NO, then at block 365 a decision is made as to whether the current leaf has a next leaf. If YES, then the current leaf is set to the next leaf and the process is repeated. If NO, then the process at block 370 returns to block 328 in FIG. 13.

Figure 16:
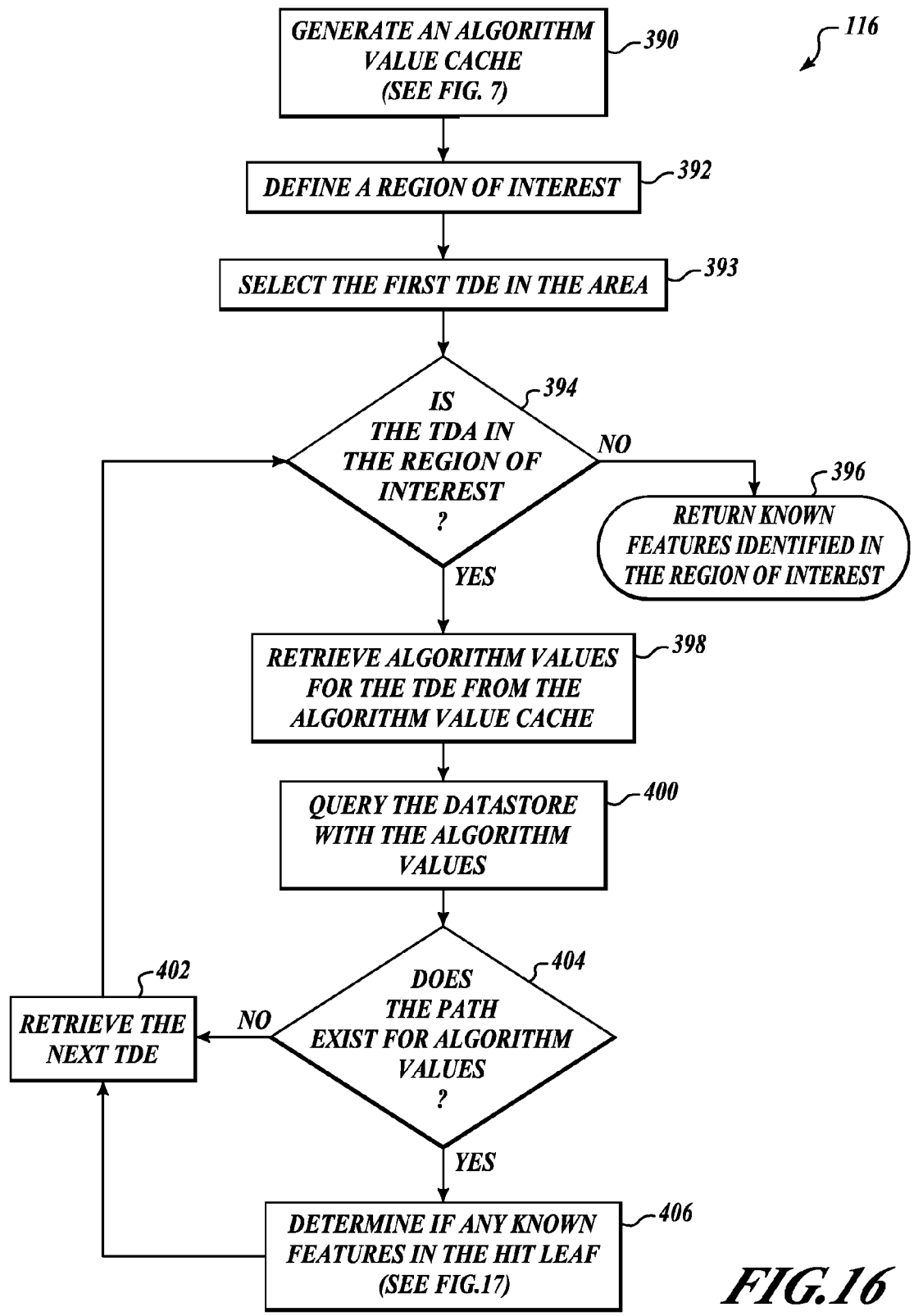
FIG. 16 shows an example method for identifying known features.

FIG. 16 shows an example method (block 116) for identifying known features. In one embodiment, at block 390 an algorithm value cache is generated. (See FIG. 7) At block 392 an area is selected in the current data. At block 393, the first TDE is selected. At block 394, a decision is made whether the TDE is in the selected area. If YES, then at block 398 algorithm values for the TDE are retrieved from the algorithm value cache if available; if not, the algorithm values are calculated for the TDE. At block 400 the datastore is queried with the algorithm values. (See FIG. 14) At block 404 a decision is made whether a path exists for the algorithm values. If YES, then at block 406 it is determined whether the match is a hit of a known feature, which is further explained in FIG. 17. If NO, then at block 402 the next TDE is retrieved. If NO from block 394, then at block 396 the identified known features are returned. Blocks 390 and 392 can be executed in any order.

Figure 17:
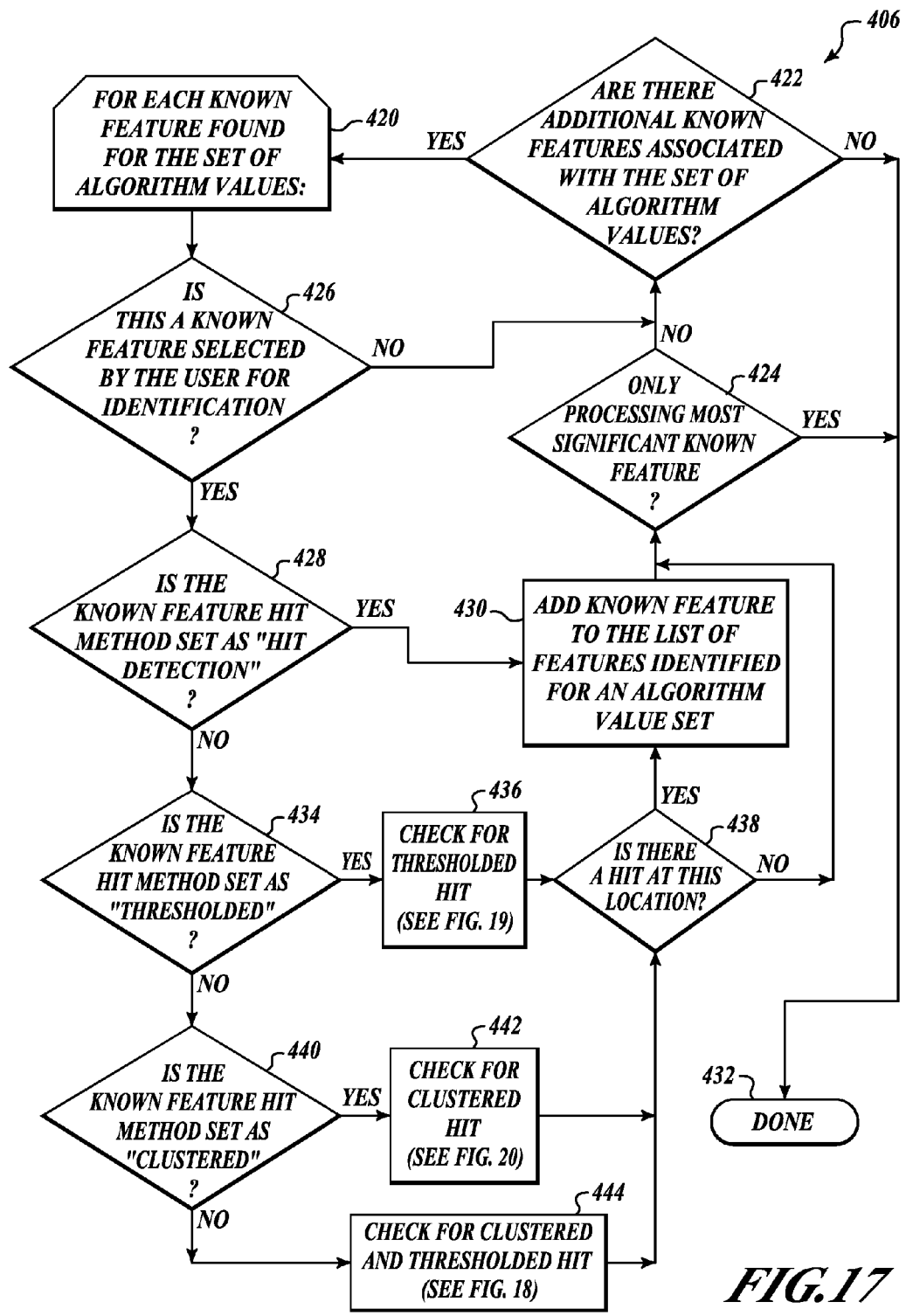
FIG. 17 shows an example method for determining if a known feature has been found.

FIG. 17 shows an example method (block 406) for determining if a known feature in a leaf hits. At block 420 for each of the known features found for the leaf, the following process is executed. At block 426, the feature is checked to see if a user selected it for identification. If YES, at block 428, then the known feature is checked to see if the hit method is set as hit detection. If NO, at block 428, then at block 434 the known feature is checked to see if the hit detection method is set as thresholded. If NO, at block 434, then at block 440, the known feature is checked to see if the known feature hit method is set as clustered. If YES from block 428, then at block 430 the known feature is added to the list of identified features for the current set of algorithm values. If YES from block 434, then at block 436 the known feature is checked for a thresholded hit which is further explained in FIG. 19. If YES from block 400, then at block 442 a check for a clustered hit is performed, which is further explained in FIG. 20. If NO from block 440, then at block 444 the system checks for a clustered and thresholded hit, which is further explained by FIG. 18. At blocks 436, 442, and 444 the data returned is either TRUE or FALSE for a hit. At block 438 the returned value is analyzed to determine if there is a hit at this location. If YES, then at block 430, the known feature is added to the list of identified features for the current set of algorithm values. If NO, in one embodiment at block 424 it is determined whether the method is processing only the most significant known feature. If YES, the method is complete; if NO, at block 422 or block 426, there is a check to see if there are additional known features associated with the current leaf. If YES, go to block 420; if NO, the method is now complete and returns through block 432 to block 406 in FIG. 16.

Figure 18:
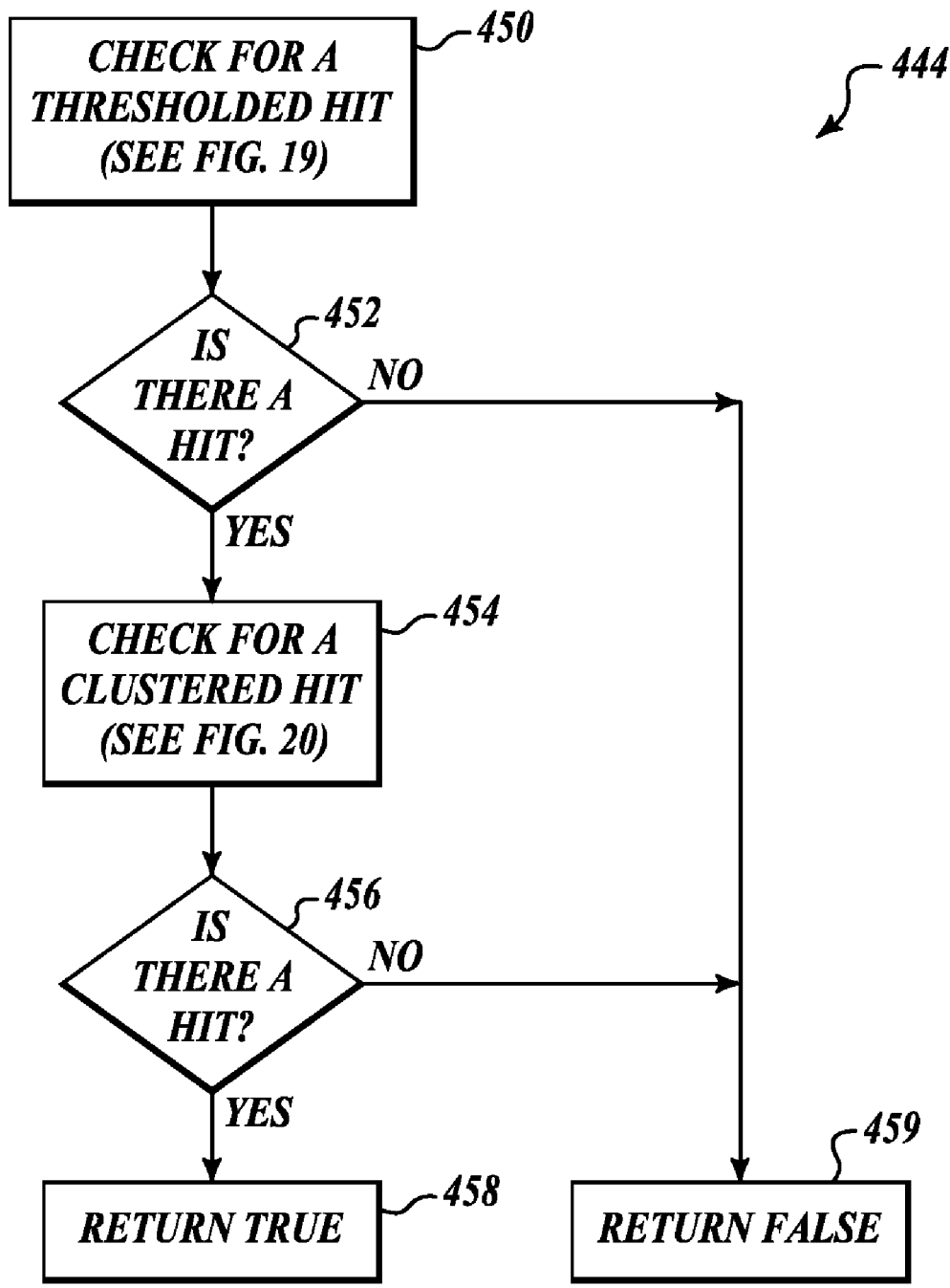
FIG. 18 shows an example method for evaluating cluster and threshold detection.

FIG. 18 shows an example method (block 444) for checking for a clustered and thresholded hit. At block 450 the method performs the check for a thresholded hit. At block 452, whether the thresholded hit was found is checked. If NO, the method proceeds to block 459. If YES, the method proceeds to block 454. In block 454, the method performs the check for a clustered hit. At block 456, whether the clustered hit was found is checked. If NO, the method proceeds to block 459. If YES, the method proceeds to block 458. At block 458, a hit was detected in thresholded and clustered processing, and so TRUE is returned to block 444 in FIG. 17. At block 459, a hit was not detected in one of thresholded or clustered processing, and so FALSE is returned to block 444 in FIG. 17. The combination of blocks 450 and 452 and the combination of blocks 454 and 456 can be executed in any order.

Figure 19:
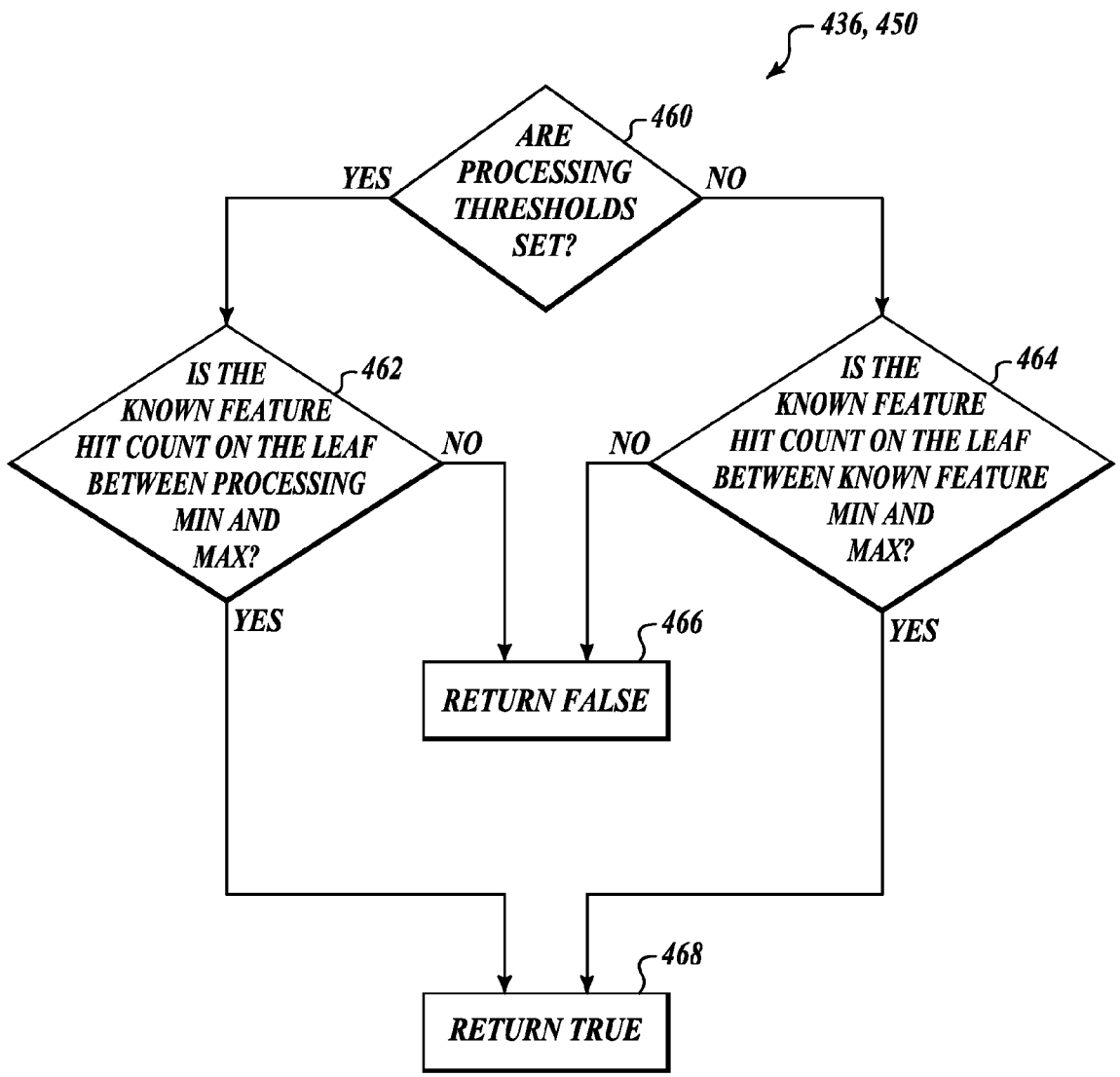
FIG. 19 shows an example method for evaluating threshold detection.

FIG. 19 shows an example method (block 436) for checking for a thresholded hit. At block 460 the system checks to see if processing thresholds are set. If YES, at block 462 a decision is made whether the known features hit count on the synaptic leaf is between the processing minimum and maximum. If YES, then TRUE is returned at block 468; if NO, then FALSE is returned at block 466. If NO from block 460, then at block 464 the known feature is checked to determine whether the hit count on the synaptic leaf is between the known feature minimum and maximum. If YES, then TRUE is returned at block 468; if NO, then FALSE is returned at block 466.

Figure 20:
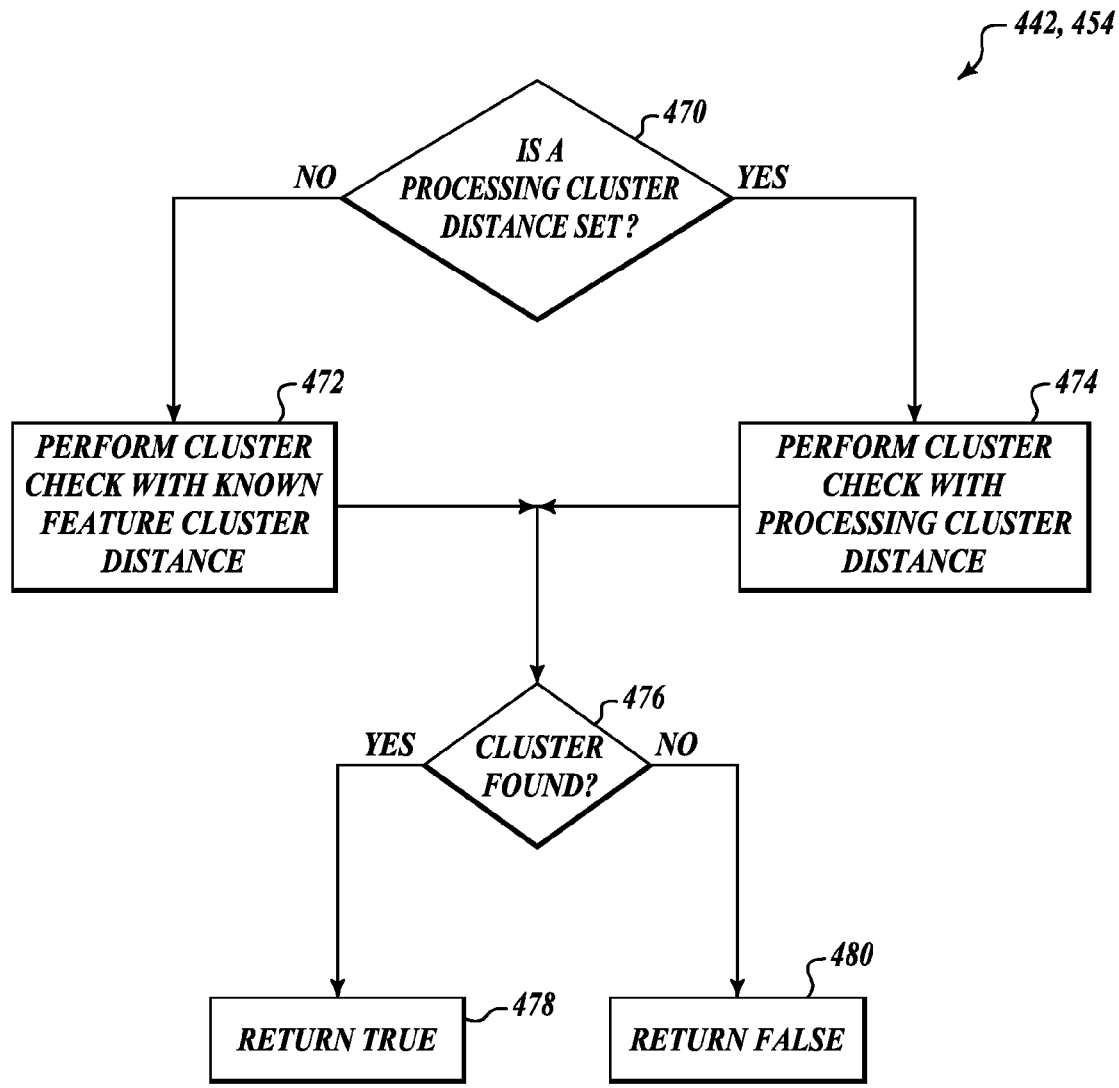
FIG. 20 shows an example method for evaluating cluster detection.

FIG. 20 shows an example method (block 442) for checking for a clustered hit. At block 470 the system checks to see if a processing cluster distance is set. If NO, then at block 472 the method performs a clustered check with known feature cluster distance. If YES, then at block 474 a clustered check is performed with processing clustered distance. Then at block 476 a check is made to see whether a cluster is found. If YES, then at block 478 TRUE is returned. If NO, then at block 480 FALSE is returned.

Figure 21:
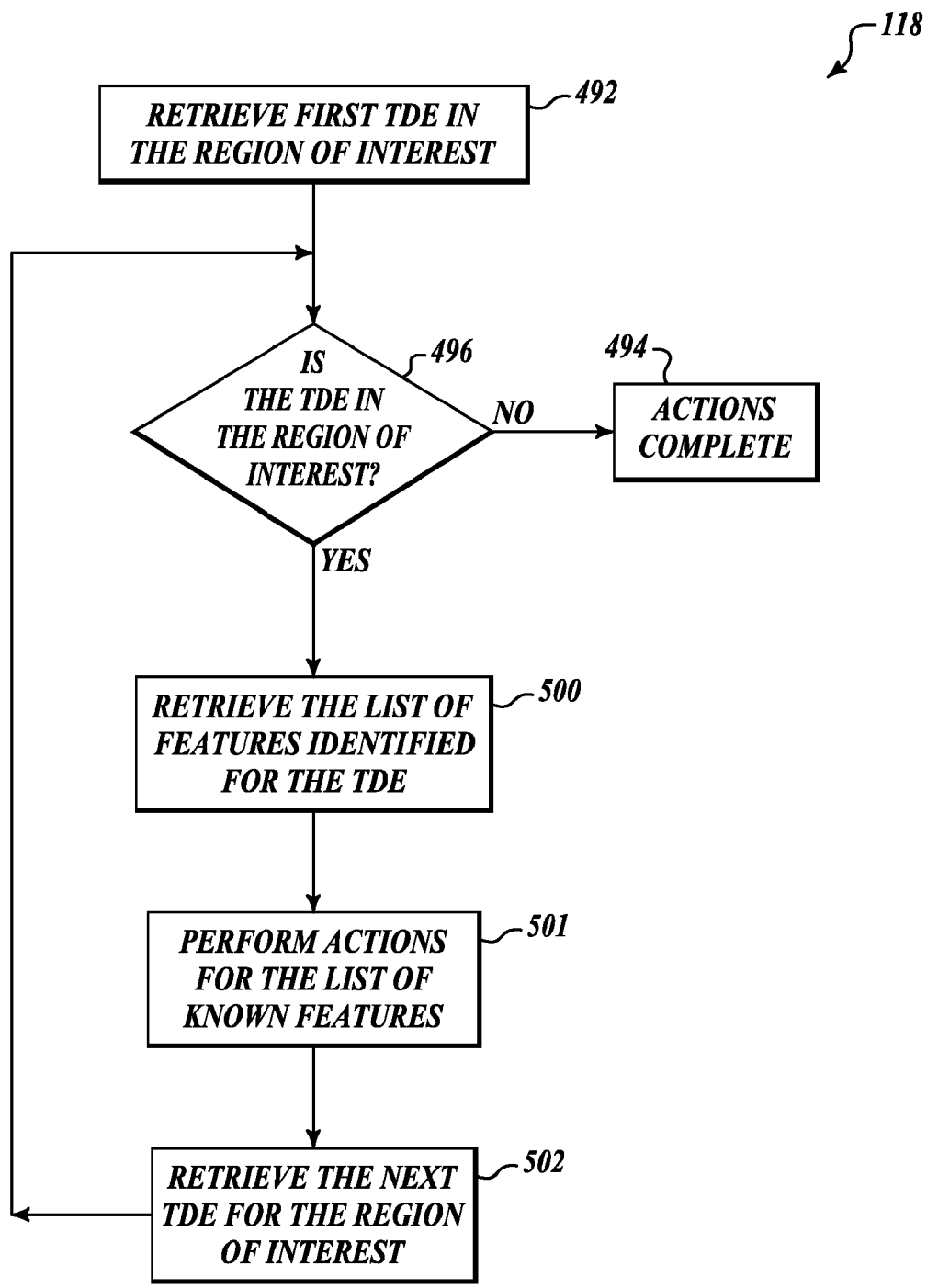
FIG. 21 shows an example method for processing the known features identified for an area.

FIG. 21 shows an example method (block 118) for processing the known features identified for an area. At block 492 the first TDE in a selected area is retrieved. At block 496 the TDE is checked to determine whether it is within the selected area. If NO, then the processing actions are complete. If YES, then at block 500 the list of features identified for the TDE is retrieved. At block 501, the actions for the list of features are performed. Once this is complete, then at block 502 the next TDE is retrieved.

Figure 22:
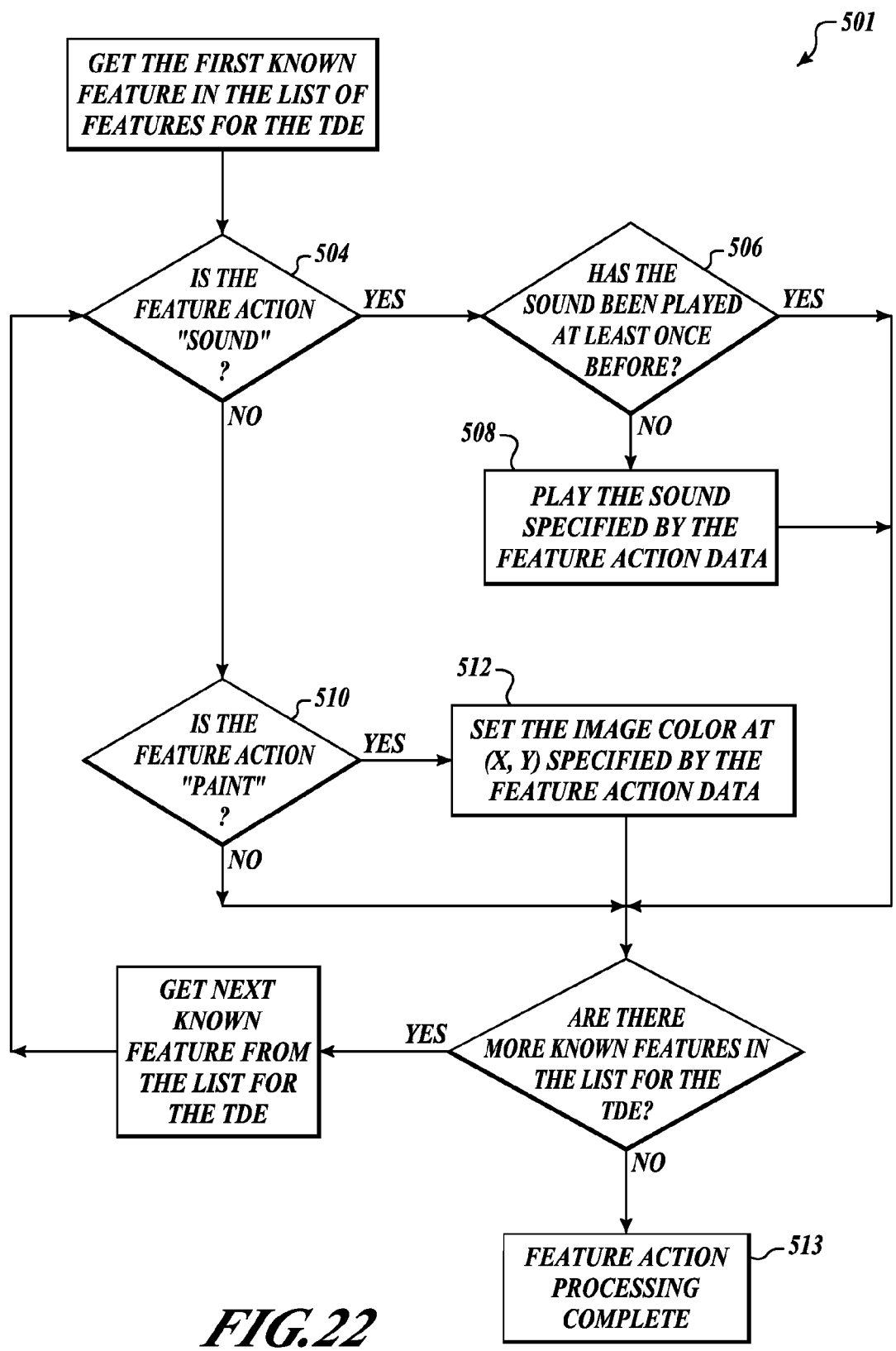
FIG. 22 shows an example method for performing a known feature action.

FIG. 22 shows an example method (block 501) in one embodiment for performing actions for a list of known features. The method (block 501) begins at block 503. At block 503, the current known feature is set to the first known feature in the list for the TDE. At block 504 the known feature action is checked to determine whether the action is a sound. Setting up a known feature action was illustrated in FIG. 5. If YES, then at block 506 the system determines whether the sound has been played at least once before. If NO from block 506, then the sound is played which is specified by the known feature action data at block 508. If NO from block 504, then at block 510 the known feature action is checked to determine if it is paint. If YES, then the image color for the TDE is set by the known feature action data. At block 511, a check is made to see if more known features are present in the list for the TDE. If YES, the current known feature is set to the next known feature, block 515, and the method continues at block 504. If NO, the method returns at block 513. Additional actions or combinations of actions are possible as needed by other embodiments. The actions may be checked and executed in any order.

FIG. 23 is an example array 600 for a 10×10 pixel image. The X coordinate for the pixel is represented by the number in the rows 604. The Y coordinate for the pixel is represented by the number in the columns 602. In one embodiment, the numbers shown within the array 600 are the original grey scale values of the 10×10 pixel image. The numbers shown are the numbers that will be manipulated using the pre-selected algorithms using the adjacent pixels TDA that includes the eight pixels surrounding the target pixel. In this example, the algorithms chosen are mean, median, spread of values, and standard deviation. Further, FIGS. 24-34 show an example of training a known feature described in FIG. 3.

FIG. 24 shows an example array 605 for the 10×10 pixel image using the mean algorithm for the adjacent pixels TDA. As shown in the array 605, the first and last rows 609 are shaded and the first and last columns 607 are shaded. These areas are shaded because they do not contain the requisite bordering pixels. The first valid pixel, which is the first pixel that is bordered on all sides by another pixel, is (2, 2), and the algorithm result is 153. The result 153 will be used further starting at FIG. 28.

FIG. 25 shows an example array 610 for the 10×10 pixel image using the median algorithm for the adjacent pixels TDA. The algorithm result for the first valid pixel is 159. The result 159 will be used further starting at FIG. 28.

FIG. 26 shows an example array 620 for the 10×10 pixel image using the spread of values algorithm for the adjacent pixels TDA. The algorithm result for the first valid pixel is 217. The result 217 will be used further starting at FIG. 28.

FIG. 27 shows an example array 630 for the 10×10 pixel image using the standard deviation algorithm. The algorithm result for the first valid pixel is 64. The result 64 will be used further starting at FIG. 28.

Figure 28:
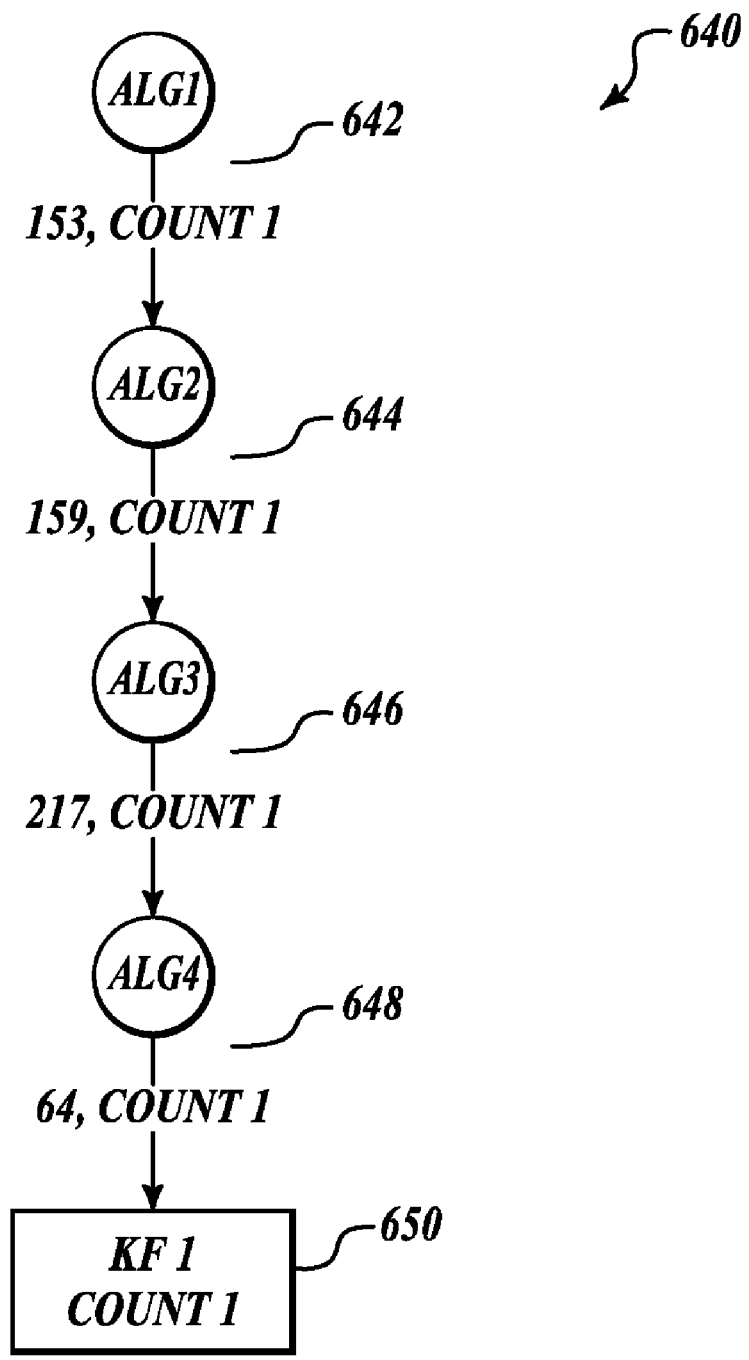
FIG. 28 shows an example synaptic web containing a single synaptic path using the values calculated in FIGS. 24-27.

FIG. 28 shows a synaptic web 640, in one embodiment, containing a single synaptic path formed from the first valid pixel values calculated in FIGS. 24-27. The first value (642) comes from the first algorithm (abbreviated ALG) (FIG. 24 at pixel 2, 2) which is 153. Therefore, 642 shows 153, count 1. Count 1 signifies the number of times during training the first algorithm had a result of 153. A second node 644 shows the result of the second algorithm (FIG. 25 at 2, 2) which is 159. Therefore, 644 shows 159, count 1. A third node 646 shows the result of the third algorithm (FIG. 26 at 2, 2) which is 217. Therefore, 646 shows 217, count 1. A fourth node 648 shows the result of the fourth algorithm (FIG. 27 at 2, 2) which is 64. Therefore, 648 shows 64, count 1. Following this synaptic path leads to a synaptic leaf containing a known feature (abbreviated KF) 1. This is the first time this synaptic path has been created, and therefore, the count is also 1, see block 650. In this example, the synaptic leaf 640 is a first synaptic leaf in the synaptic web.

Figure 29:
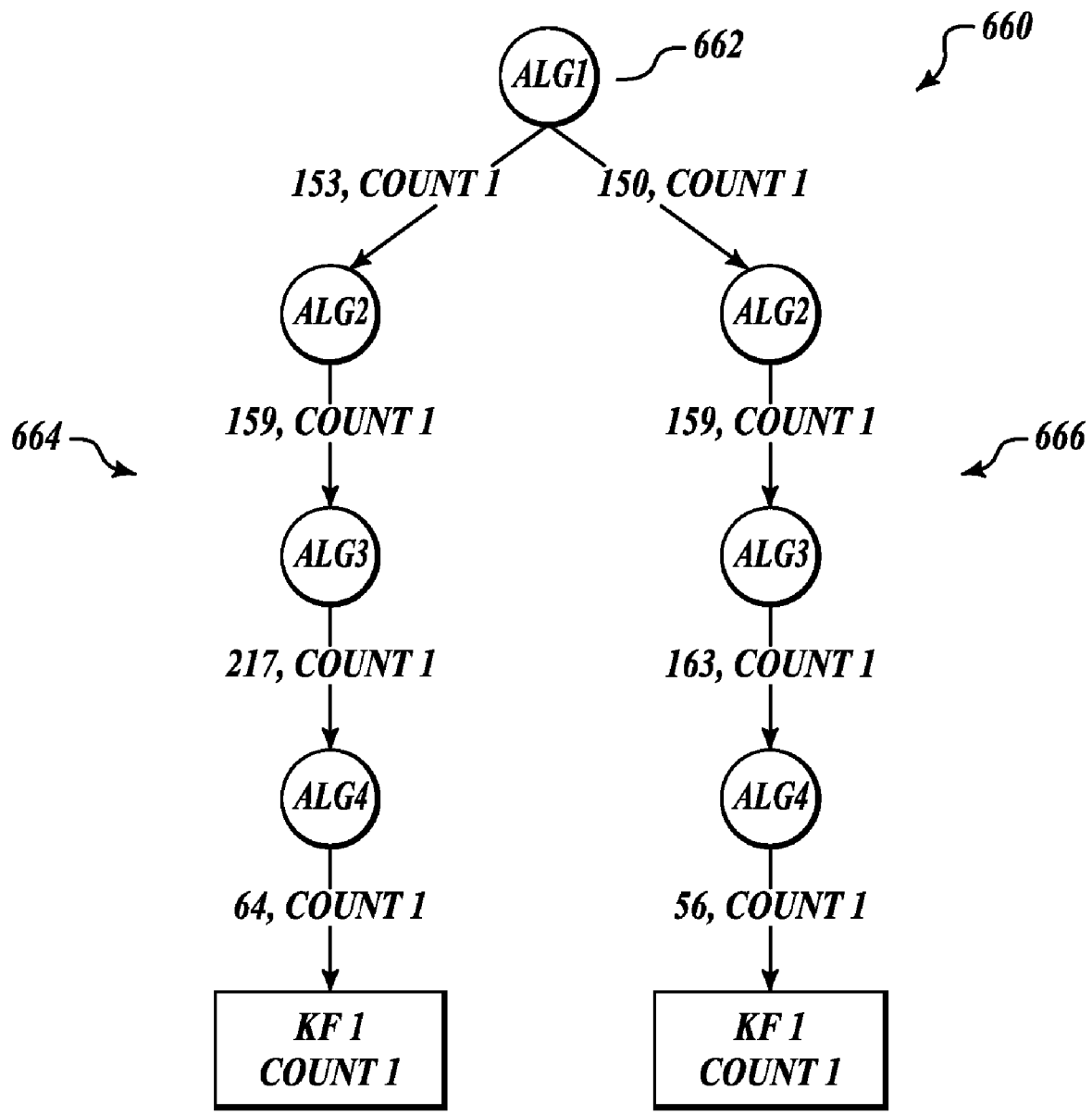
FIG. 29 shows an example synaptic web containing two synaptic paths using the values calculated in FIGS. 24-27.

FIG. 29 shows an example synaptic web 660, in one embodiment, containing two synaptic paths using values calculated in FIGS. 24-27. A synaptic leaf 664 was shown and described in FIG. 28. A synaptic leaf 666 represents the algorithm values for the pixel (2, 3) from each table shown in FIGS. 24-27. Therefore, after analyzing two pixels, there are two different synaptic paths that identify the same known feature.

Figure 30:
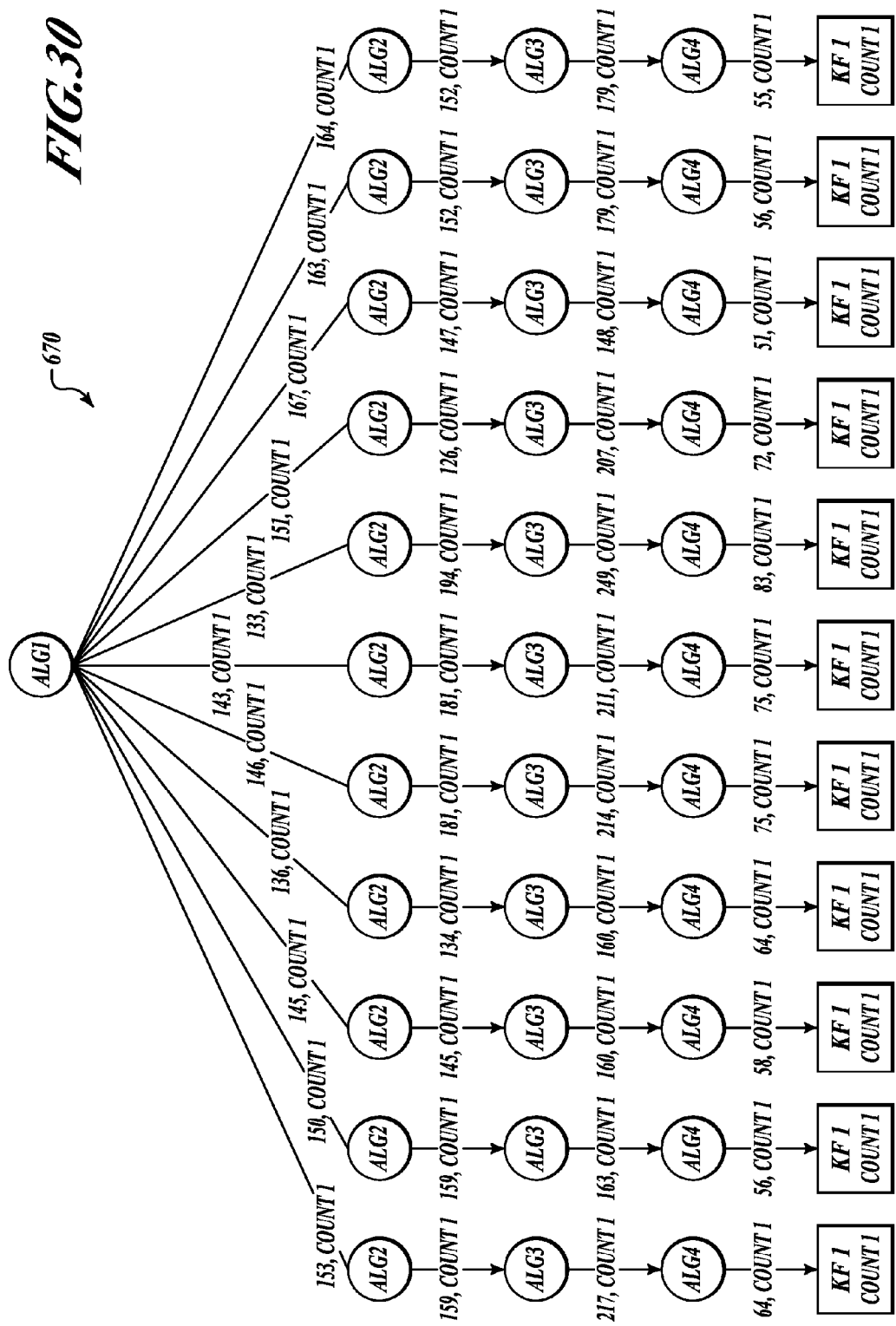
FIG. 30 shows an example synaptic web containing many synaptic paths using the values calculated in FIGS. 24-27.

FIG. 30 shows an example synaptic web 670, in one embodiment, using values calculated in FIGS. 24-27. The values calculated from the tables shown in FIGS. 24-27 represent pixels (2, 2) through (3, 4). The values were taken from left to right within the rows. At this time in the calculation, there has not been a repeat in the values from the first algorithm; therefore, for every pixel evaluated, a completely new synaptic path and a new synaptic leaf were added to the synaptic web.

Figure 31:
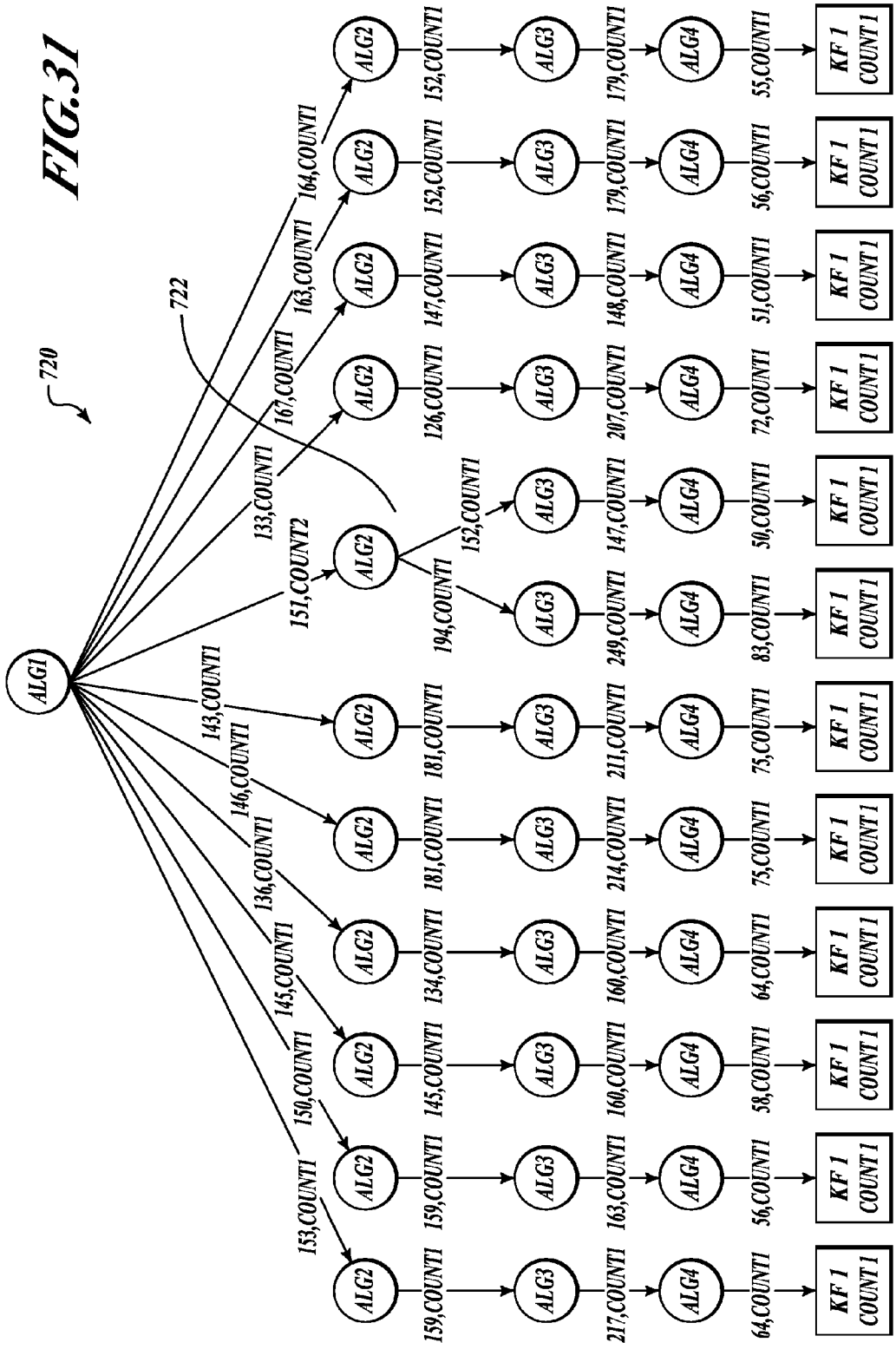
FIG. 31 shows the example synaptic web from FIG. 30 with the next synaptic path added, showing how the synaptic web can branch.

FIG. 31 shows an example synaptic web 720, in one embodiment, using values calculated in FIGS. 24-27. In the synaptic web 720, there is a repeat value shown at 722. The first algorithm value 151 was found both at (2, 8) and (3, 5) therefore increasing the count at that position to equal 2. At 722, the synaptic path splits because of different values retrieved from the second algorithm. A portion of a new synaptic path and a new synaptic leaf are generated for the set of values.

Figure 32:
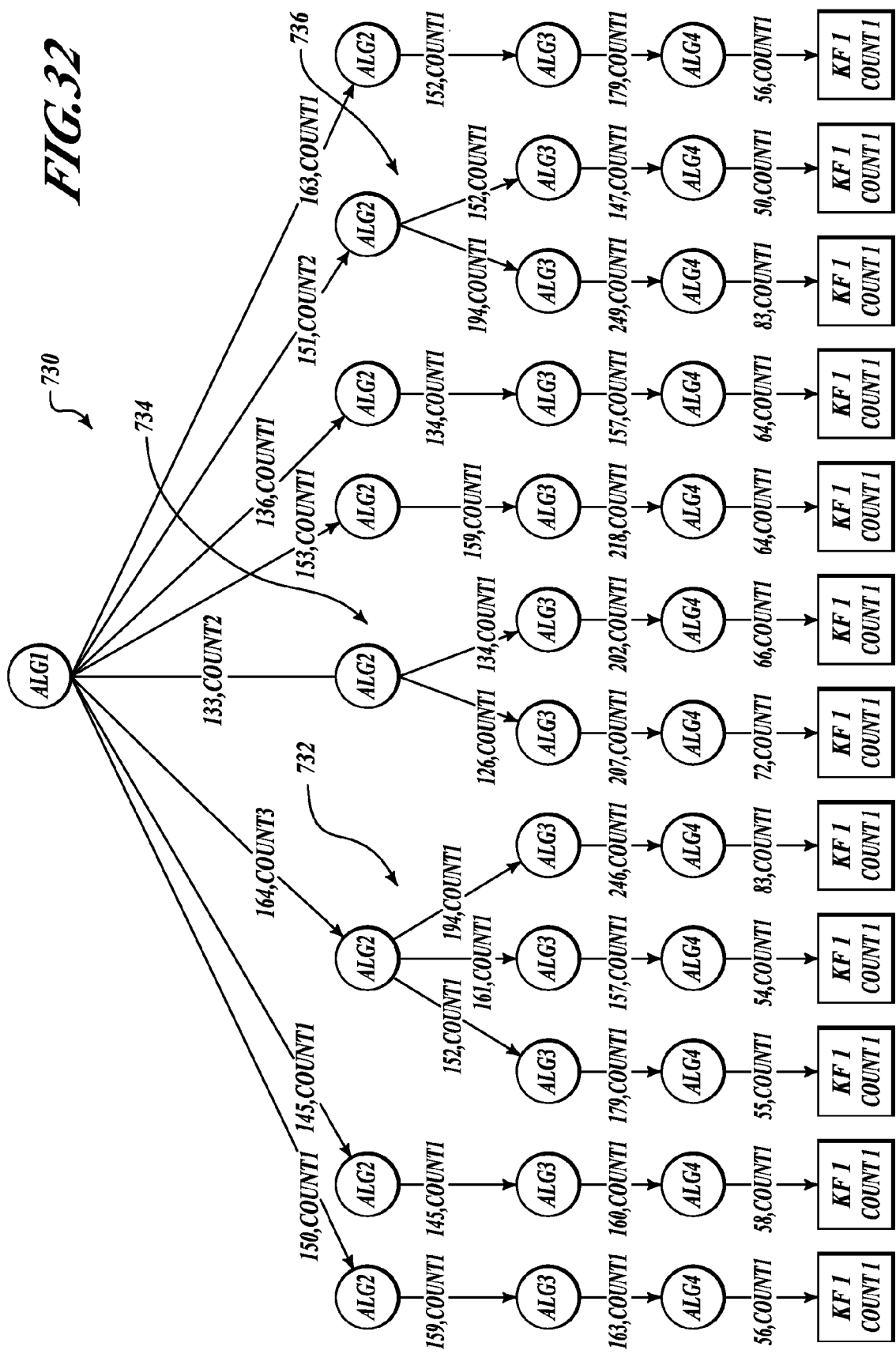
FIG. 32 shows an example synaptic web containing all the synaptic paths using the values calculated in FIGS. 24-27.

FIG. 32 shows an example synaptic web 730, in one embodiment, using values calculated in FIGS. 24-27. This example shows a more populated synaptic web 730 with repeats in the first algorithm value at 732, 734, and 736. The repeats show that at any node in the synaptic web a new branch can be formed and a new synaptic path will be formed. As shown in node 732, there are three diverging results that still result in the same known feature. FIG. 32 further demonstrates a graphical representation of what fully populated synaptic web may look like after training a known feature.

Figure 33:
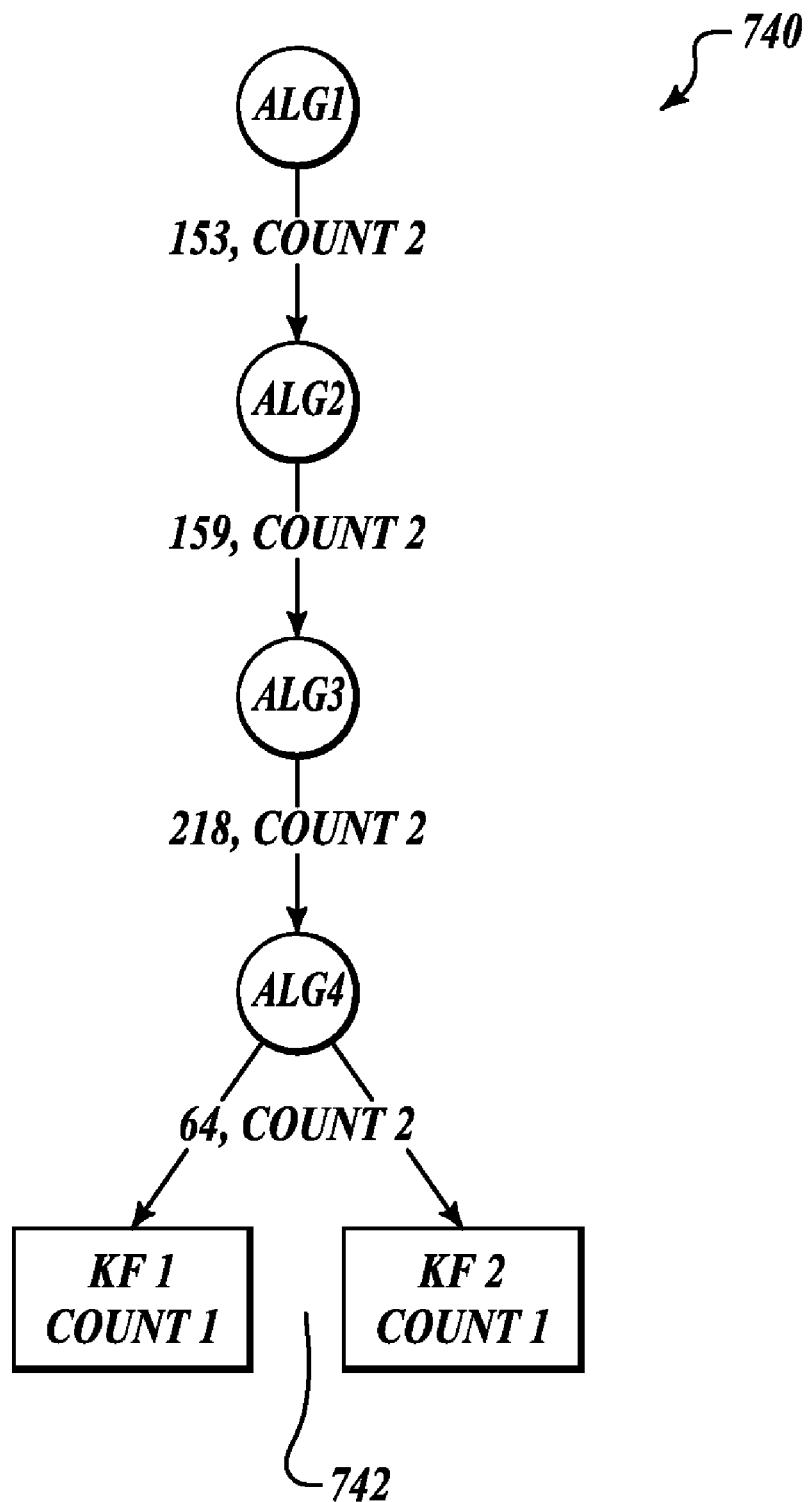
FIG. 33 shows a synaptic path which results in a synaptic leaf having multiple known features.

FIG. 33 shows a synaptic path 740 that results in a synaptic leaf having multiple known features 742. When multiple known features are associated with a synaptic path, the features are stored in a sorted list ordered by the feature's hit count. The known feature that has most often been associated with the synaptic pattern appears first in the list, followed by other known features, in decreasing hit count order. In case of a tie, the first known feature associated with the synaptic path will appear first.

FIG. 34 shows a series of arrays for a 6×6 black and white image. The array at the top of the page shows the brightness value for all the pixels in the image. The next array 680 shows the results of the mean algorithm applying the adjacent pixels TDA to top array. Array 690 shows the results of the median algorithm after applying the adjacent pixels TDA to top array. Array 700 shows the results of the spread of values algorithm after applying the adjacent pixels TDA to top array. Array 710 shows the results of the standard deviation algorithm after applying the adjacent pixels TDA to top array. As an example, the results of arrays 680-710 are applied to the synaptic web in FIG. 32. The resultant value shown in (2, 2) from array 680 is 164. Now referring to FIG. 32, the value 164 is found in the first node of the synaptic web at 732 in FIG. 32. Next, using the value 152, which is the value found at (2, 2), it is shown in FIG. 32 that the next node following 164 is 152. Therefore, these first two values follow a known synaptic path. Following this synaptic path and the values in (2, 2) in arrays 700 and 710 show that at pixel (2, 2); there is a match of the known feature trained in the synaptic web.

In FIGS. 35-77, the screenshots represent one example of an interface; infinite alternatives exist.

Figure 35:
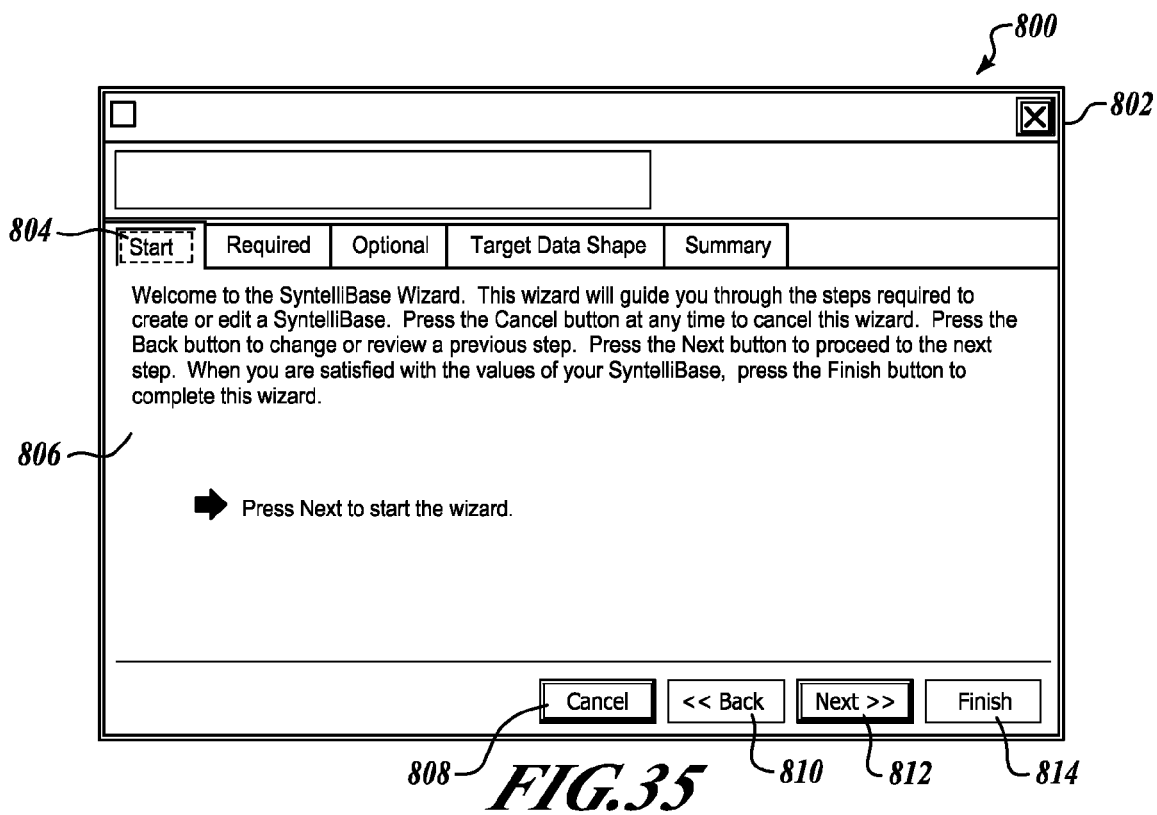
FIG. 35 shows a screenshot of an introduction screen when setting up a datastore.

FIG. 35 is a screenshot 800 of an introduction screen when setting up a datastore. This shows the introduction for a wizard 802 that will guide the user through the steps in this application to create and/or edit a datastore. Also shown in this FIGURE is a series of tabs 804. These tabs show the user's position within the wizard. In the top right corner is a button providing the ability to close and exit the wizard 802. At the bottom of the screenshot is an option button 808 to cancel, the option button 810 to go back, the option button 812 go to the next step, and the option button 814 to finish. The general layout described above is prevalent throughout most screenshots.

Figure 36:
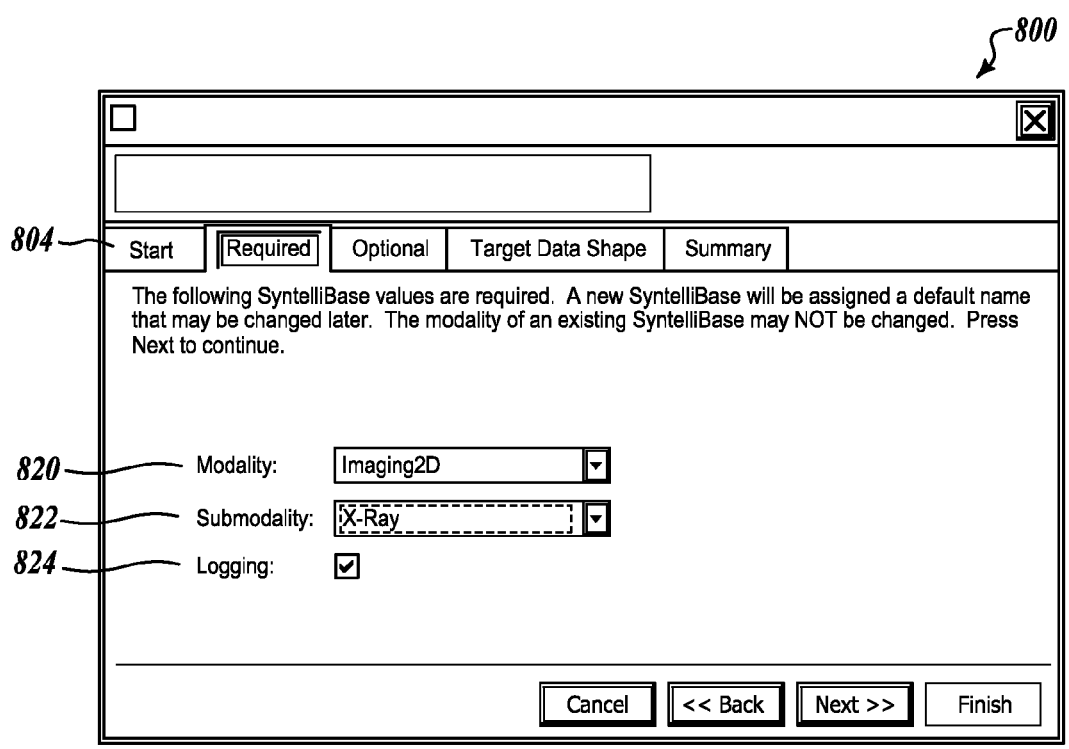
FIG. 36 shows a screenshot of entering a set of initial values.

FIG. 36 is a screenshot showing the entering of the initial values defining the datastore. The tab "Required" 804 is selected showing a set of values necessary in this application. At this stage a user is identifying the type of digital data to be processed. A modality combo box 820 contains a series of modalities which specifies the format of the digital data stream. A submodality combo box 822 contains a series of submodalities which specifies the use of the information or specific application of the modality. Logging is represented by a checkbox 824.

Figure 37:
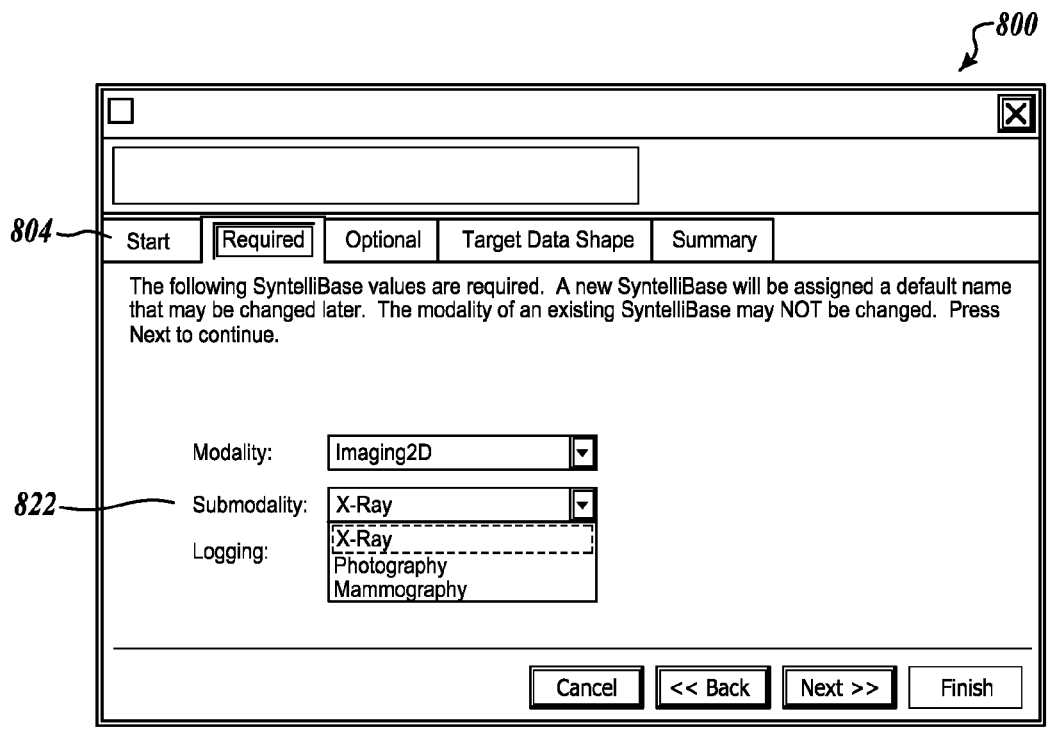
FIG. 37 shows a screenshot of the expanded submodality combo box.

FIG. 37 shows a screenshot showing the submodality combo box 822 expanded. The submodality combo box 822 has been expanded to show, in one embodiment, a configurable list of submodalities that have currently been set up for a two-dimensional image modality. This combo box 822 shows a user the number of sub classifications within the previously selected form of digital data to enable a user to address differences in digital data within a modality.

Figure 38:
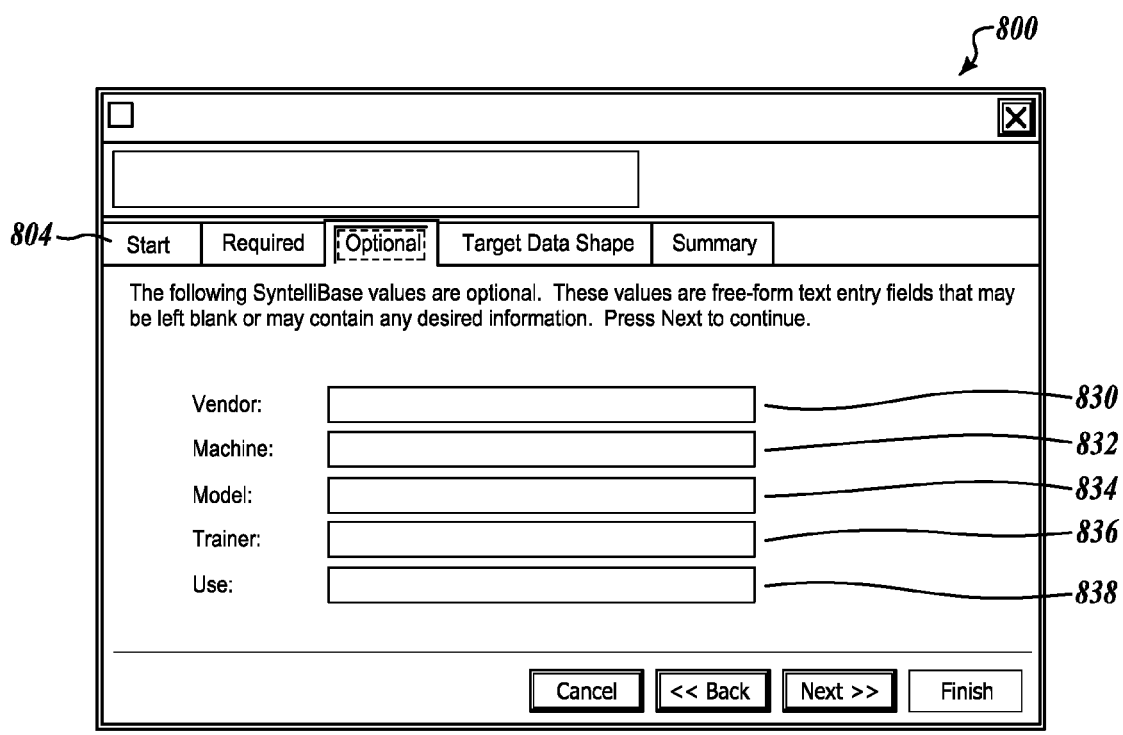
FIG. 38 shows a screenshot of a series of textboxes used to add optional descriptive parameters.

FIG. 38 is a screenshot showing a series of textboxes to add optional descriptive parameters in this application. The "Optional" tab has been selected. The information from this screenshot can be used to categorize datastores received and stored by a network. At textbox 830, a vendor's name is entered. At textbox 832, a machine type is entered. At textbox 834, a model for the machine type is entered. At textbox 836, the name of the trainer is entered. At textbox 838, the use of the datastore is described.

Figure 39:
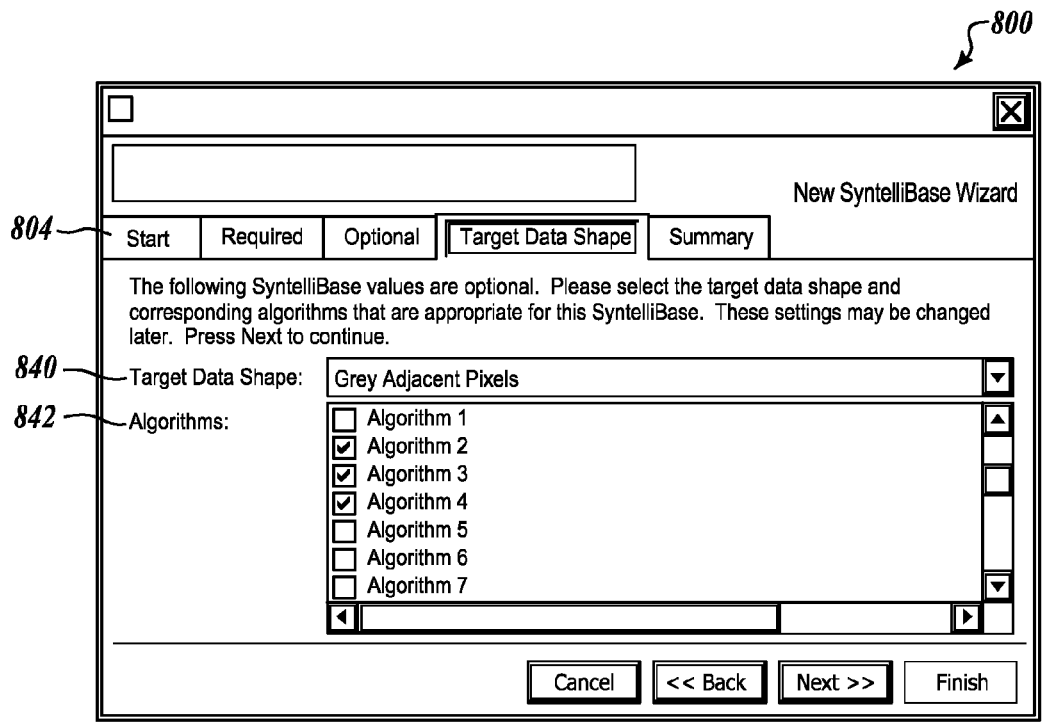
FIG. 39 shows a screenshot of the selection of a target data area shape and a set of algorithms for the shape.

FIG. 39 is a screenshot allowing for the selection of a TDA shape and a set of algorithms for the shape. The "Target Data Shape" tab 804 is selected. A combo box 840 allows a user to select a target data shape in order to determine how data is collected immediately surrounding the TDE. In one embodiment, a "Grey Adjacent Pixels" TDA is selected. In one embodiment the process of selecting algorithms begins by choosing a TDA shape. In the case of FIG. 39, the TDA shape chosen is a square of 9 pixels with the center pixel being the TDE (known here as "Grey Adjacent Pixels" because all of the remaining data elements touch the TDE). Next, a group of three algorithms are chosen. In this example, Algorithm 2, Algorithm 3 and Algorithm 4 (algorithms may be simple or complex) are used to extract the data to be used in training within the Synaptic Web. Note that in this example, it is a combination of the results of the three algorithms that are used by the Synaptic Web for training and processing, not just a single algorithm.

Figure 51:
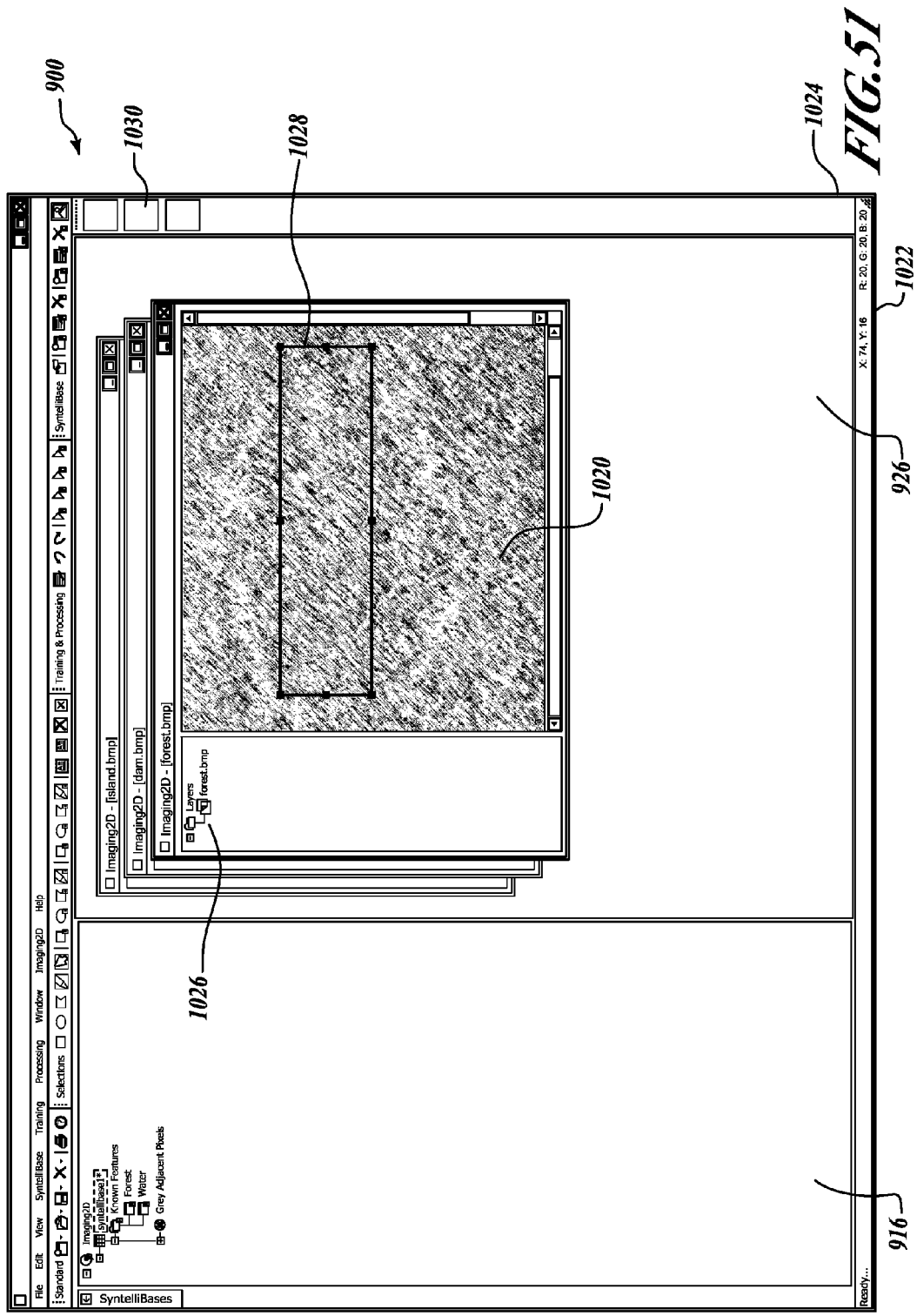
FIG. 51 shows a screenshot of an image of a forest with a selected region of interest.

At this point an area of the image is selected that contains the part of the image whose contents will be used in the training (shown in FIG. 51). This area is called the Selection Area. With the Selection Area chosen, the system steps the TDA onto the Selection Area with the TDE at the first pixel in the Selection Area. At this location, the group of three algorithms chosen for the training is run on the TDA. Algorithm 2 (Mean of the TDA values) sums the values of all of the pixels in the TDA and divides that sum by the number of the pixels, 9, resulting in the mean of the TDA. This mean value is put in the Synaptic Web for its use in the training session as described within the section on the Synaptic Web. Algorithm 3 (Median of the TDA values) determines the median value of all of the 9 pixels in the TDA. This median value is put in the Synaptic Web for its use in the training session as described within the section on the Synaptic Web. Algorithm 4 (Spread of the TDA values) determines the lowest pixel value and highest pixel value of all of the 9 pixels in the TDA. It then subtracts the lowest value from the highest value resulting in the spread of the values of the TDA. This spread is put in the Synaptic Web for its use in the training session as described within the section on the Synaptic Web. At this point, the system steps the TDA shape by one position where the TDE is now the next pixel with 8 adjacent pixels. The same group of 3 algorithms is run on this new TDA and the results put in the Synaptic Web for its use. The system will step the TDA and run the group of algorithms one position at a time until all of the pixels in the Selection Area have been a TDE. The above process for training is similar to the identification process. The same TDA Shape and Algorithms are used for identification as training. A Selection Area is chosen and the TDA is shifted across the Selection Area and at each new point runs the group of algorithms. At this point the results of the algorithms are not used by the Synaptic Web for training, but compared to known features for identification.

The algorithms available to the user are designed to analyze possible characteristics of the area surrounding the target pixel. Some examples are arithmetic algorithms, such as sums or spread of values, or statistical algorithms such as standard deviation. For certain TDA shapes, additional algorithms can be developed that consider the geometry of the shape. For example, an algorithm for 2D imaging can be implemented that sets bit values to 1 when particular pixels surrounding the target pixel are above a known value, thus creating a number from 0 to 255 reflecting the neighboring pixel surrounding the target pixel. The type of algorithm and the range of values returned for a given range of input values are factors for the user to consider when choosing which algorithms to select for a given process. For example, the spread and sum of values are useful in almost any application, while the neighboring pixels algorithm might only be useful in image processing where high contrast is expected and the specific orientation of the pixels is known or expected. In most embodiments, a single algorithm is generally insufficient to identify features; a combination of algorithm values is used to learn and/or identify features.

Figure 40:
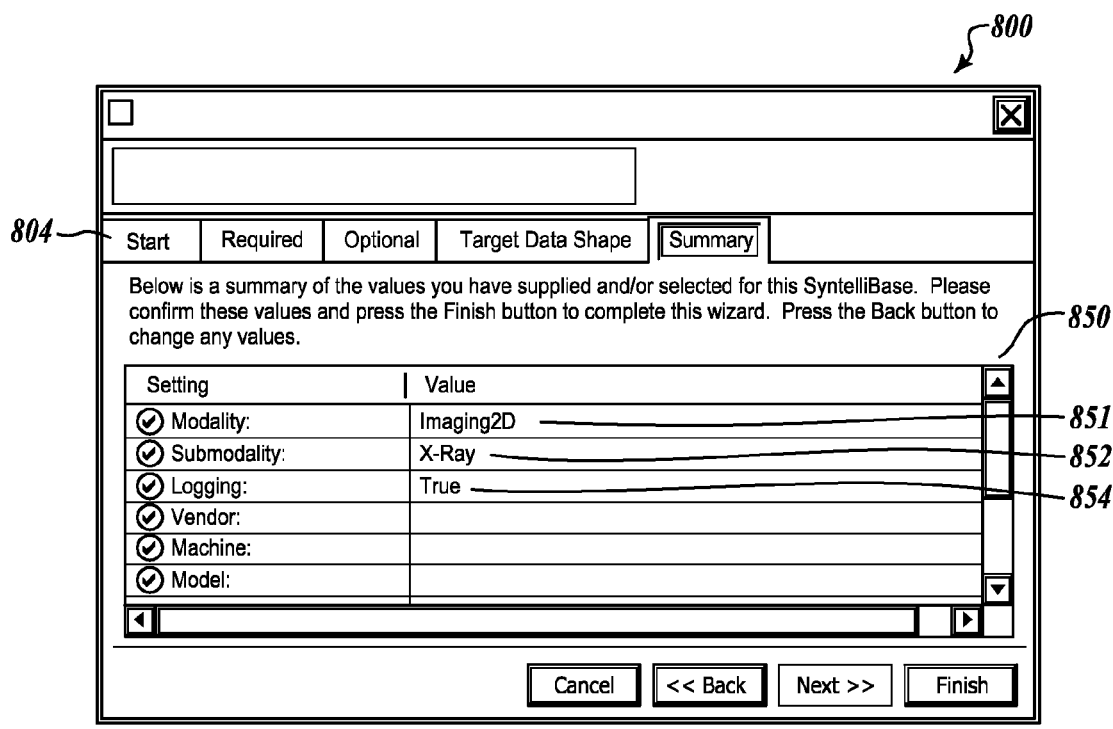
FIG. 40 shows a screenshot of a review of the datastore properties previously selected.
Figure 41:
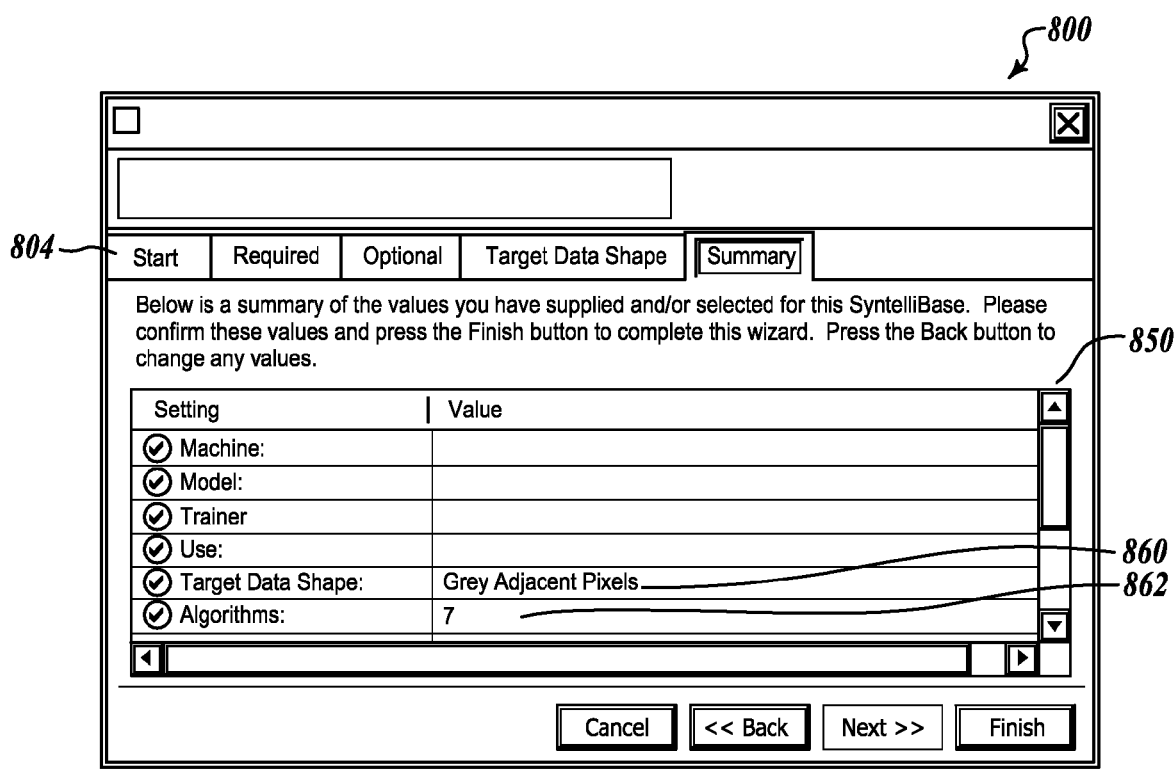
FIG. 41 shows a continuation of the summary displayed in FIG. 40.

FIG. 40 is a screenshot showing a review of the datastore properties previously selected. The summary tab 804 has been selected denoting that this screen shows a user the summary of all his/her settings. The screen allows for a user to confirm all his/her selections by pushing the "finish" button or by editing his/her features by selecting the "back" button. Shown in this table is that modality is set as Imaging2D 851. The submodality is set as X-Ray 852. The logging is selected as True 854. FIG. 41 shows the screenshot showing the table 850 in FIG. 40 scrolled down. Further shown in FIG. 41 is the target data shape selected with a "Grey Adjacent Pixels" TDA 860 and the number of algorithms selected with seven 862.

Figure 42:
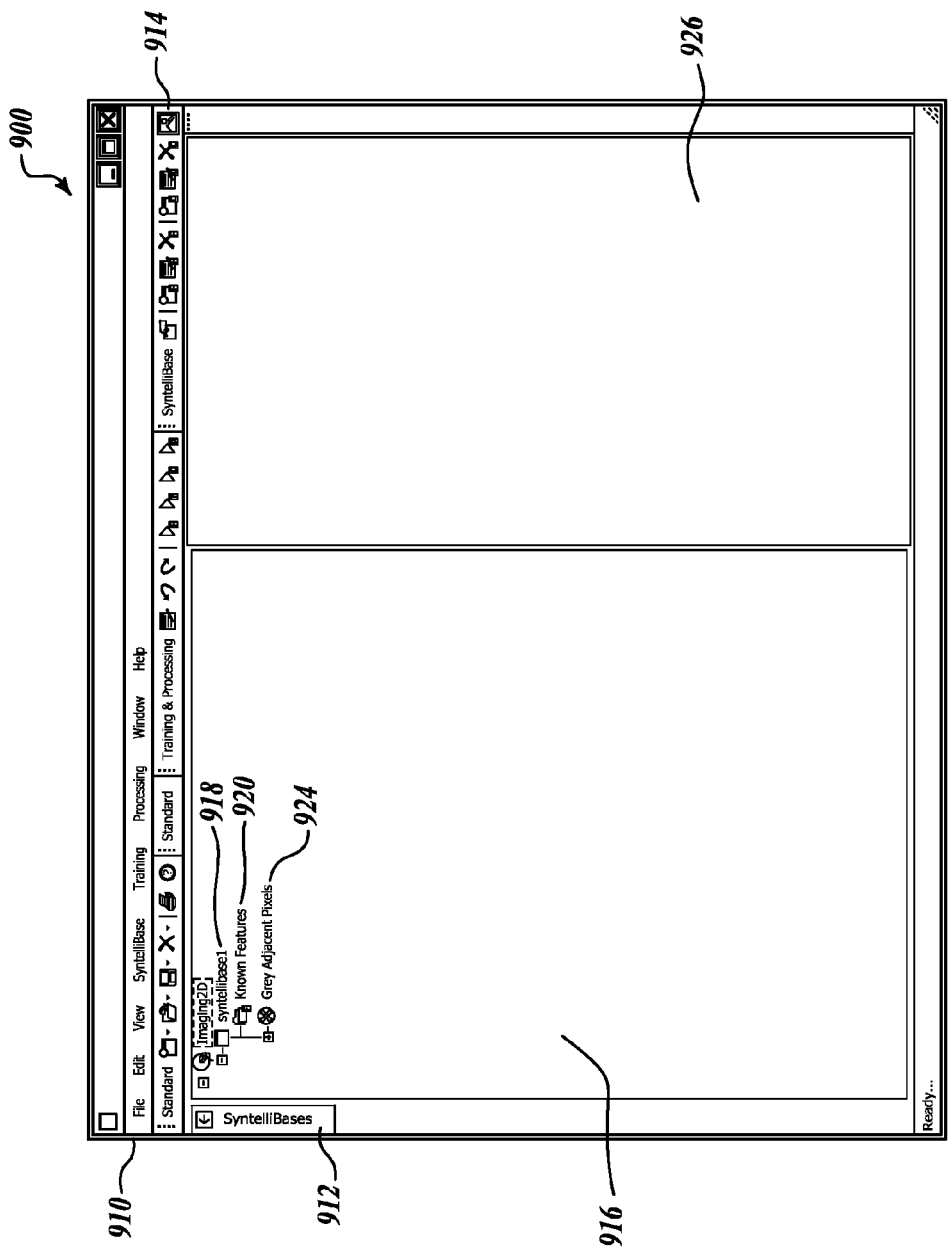
FIG. 42 shows a screenshot of an example application after finishing the creation of a datastore.

FIG. 42 shows a screenshot of an application after finishing the creation of the datastore. At the conclusion of the wizard (FIGS. 35-41), the screen 900 is shown to the user. Screen 900 contains a menu bar 910, which is known in the art, a set of icons 914 and an area to review multiple datastores 912. A shaded area 926 can display a set of pictures that a user can use to train the datastores and identify different features. In the area 916, a list is displayed of the selections made by the user at this point. In one embodiment, there is one datastore for 2D imaging 918. A set of known features, when defined, are stored in the known features folder 920. The "Grey Adjacent Pixels" TDA is displayed at 924.

Figure 43:
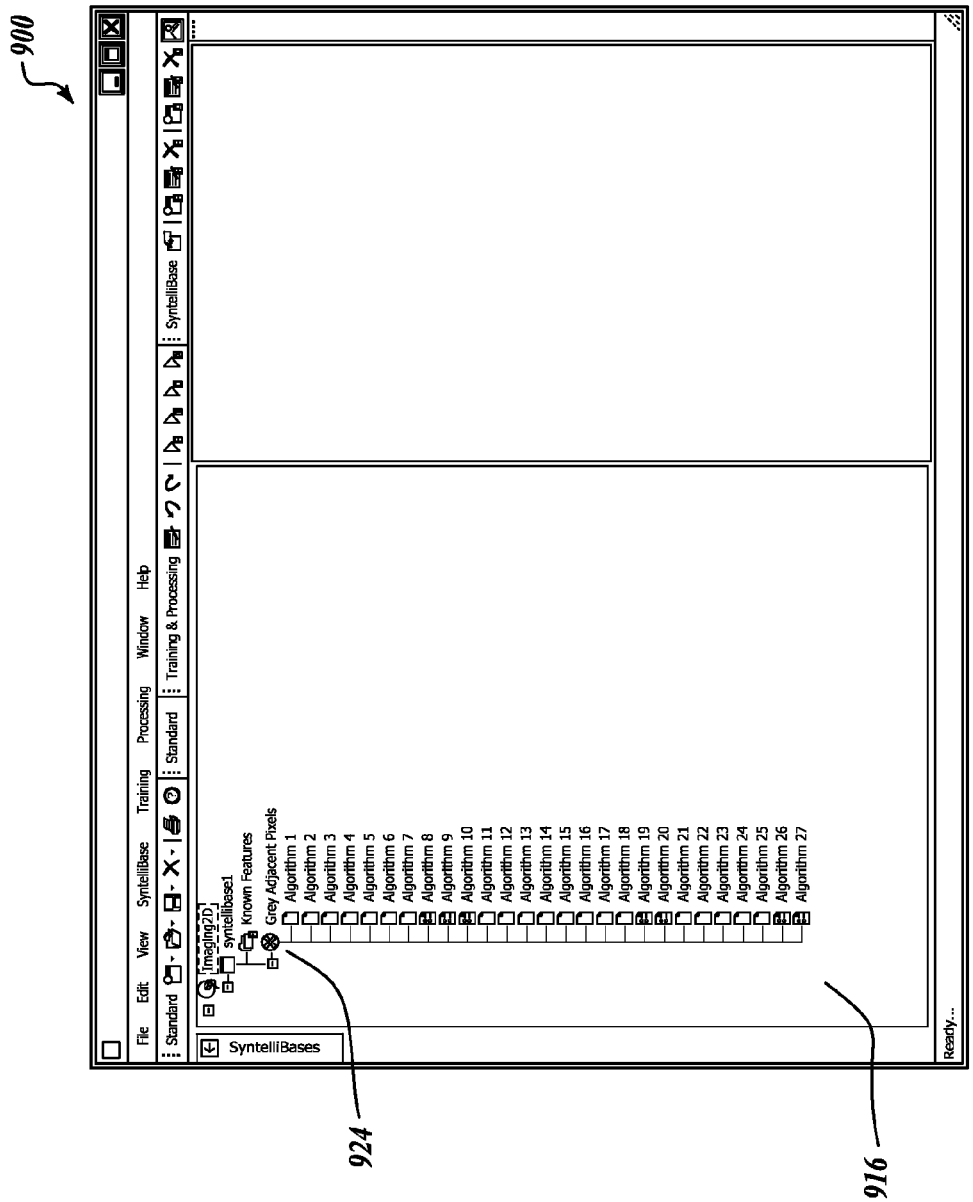
FIG. 43 shows a screenshot of the algorithms of the grey adjacent pixel target data area.

FIG. 43 is a screenshot showing an expansion of the TDA 924. The TDA 924, as shown in FIG. 43, is now expanded to show possible algorithms that could be used in conjunction with the TDA. In this application, the selected algorithms have a filled-in box denoting that they have been selected.

Figure 44:
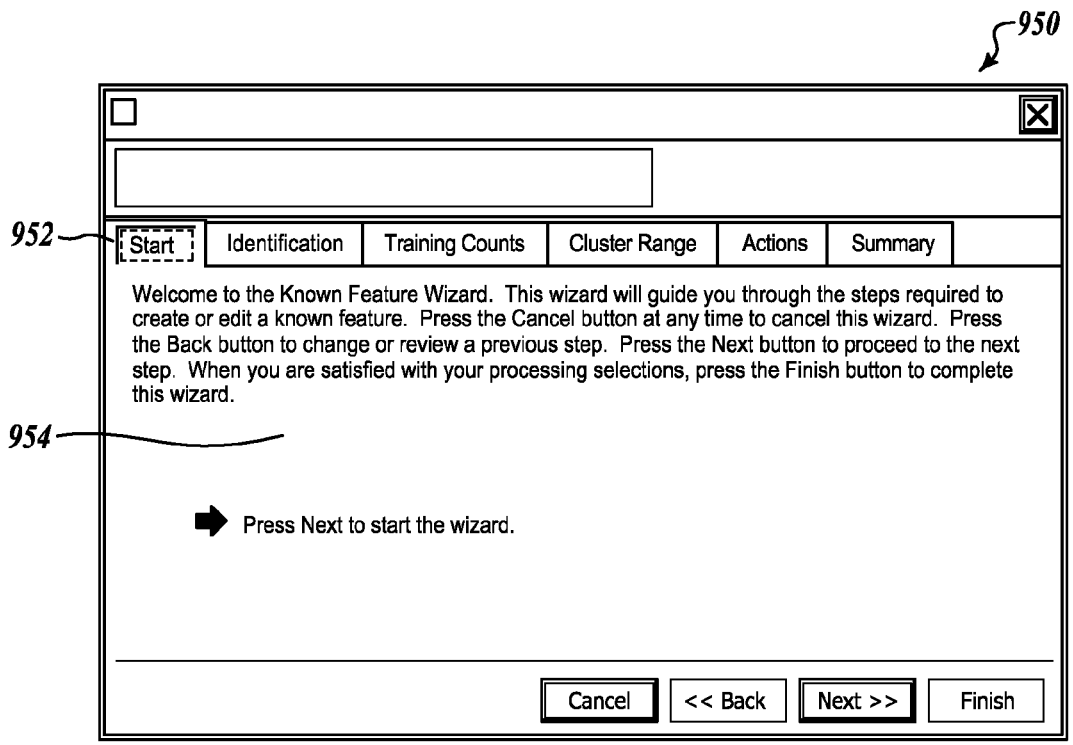
FIG. 44 shows a screenshot of a "create or edit a known feature" wizard.

FIG. 44 is a screenshot showing a "create or edit a known feature" wizard 950. In the wizard 950 is a set of tabs 952. The "Start" tab is selected denoting that this is the introduction to the wizard. This wizard will guide a user through the steps in this application to create and edit a known feature, see area 954.

Figure 45:
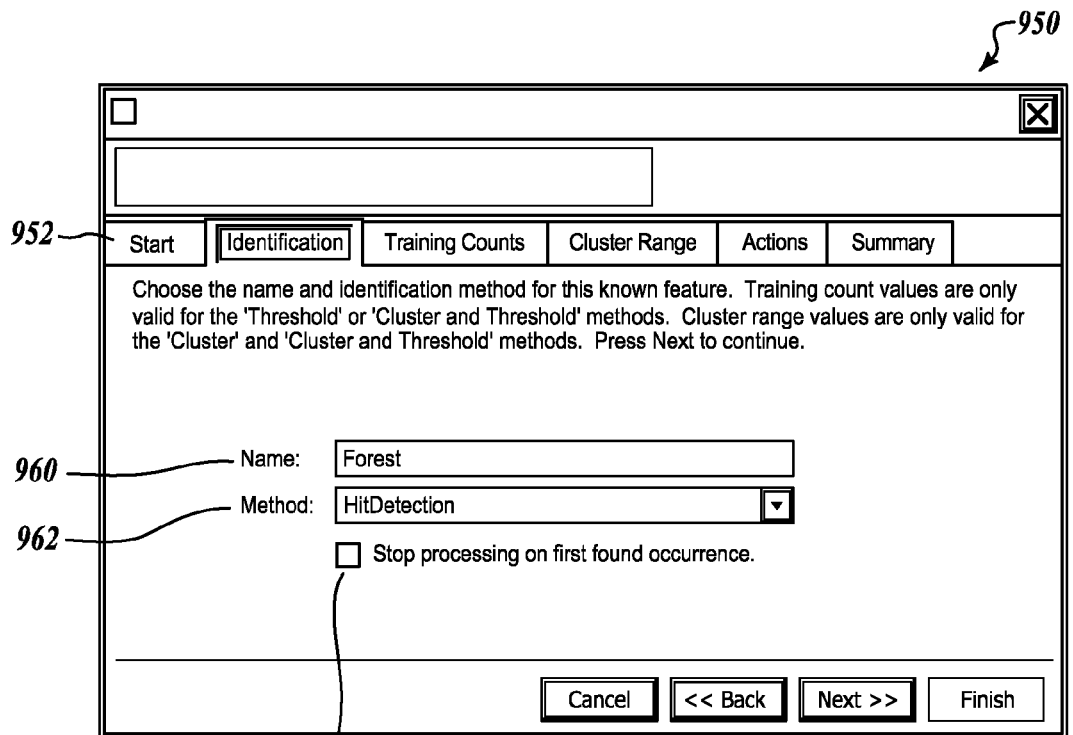
FIG. 45 shows a screenshot of the selection of a name and detection method for a known feature.

FIG. 45 is a screenshot showing the "Identification" tab 952 of the "create or edit a known feature" wizard. The textbox 960 contains the name of the known feature. In one embodiment, the user enters a name that describes the known feature; in this example "forest" was entered. The combo box 962 shows the method of hit detection selected by the user. The check box 964 allows the user to determine whether the process should stop after the first occurrence of that particular feature has been found. A user may select check box 964, if only looking for an instance of the known feature, such as foreign matter in a food sample in a food safety application.

Figure 46:
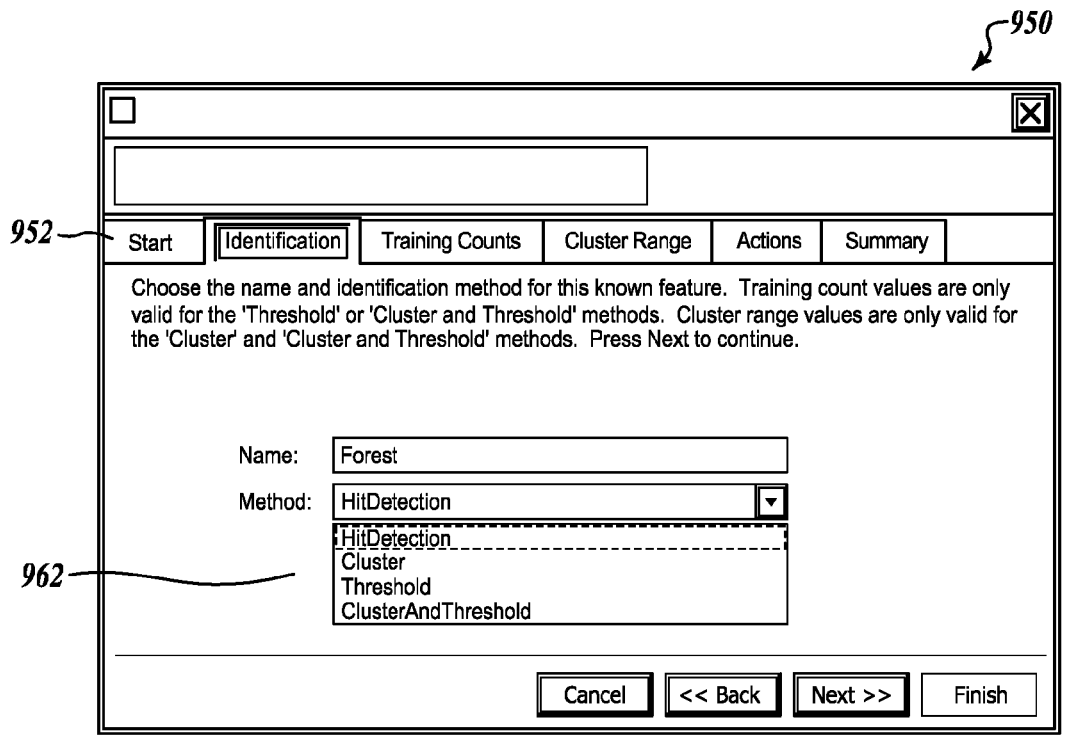
FIG. 46 shows a screenshot of the expanded combo box from FIG. 45.

FIG. 46 is a screenshot showing the expansion of the combo box 962 from FIG. 45. The identification method combo box 962 contains the method used to determine how a feature will be identified.

Figure 47:
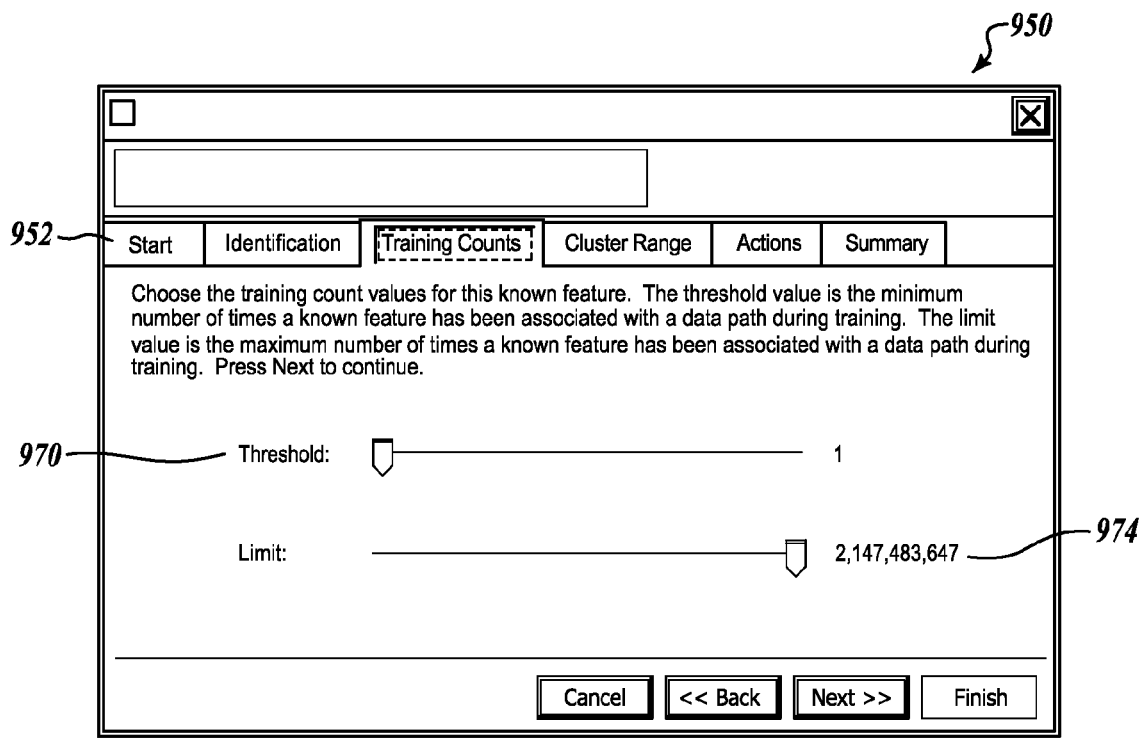
FIG. 47 shows a screenshot of the training count values for a known feature.

FIG. 47 is a screenshot showing the "Training Counts" tab 952 of the "create or edit a known feature" wizard. A user may select a threshold value representing the minimum number of times a known feature must be associated with a synaptic path during training to meet the user's needs. By increasing the threshold value, a user guarantees that only recurring paths that have higher number of instances than the threshold value are used in processing, thus giving a higher level of confidence to the eventual identification of the feature. A limit value may also be selected and contains a value that represents the maximum number of times a known feature may have been associated with the synaptic path during training. A sliding scale 970 is used to represent the threshold number, and a sliding scale 974 is used to represent the limit number.

FIG. 48 is a screenshot showing the "Cluster Range" tab 952 of the "create or edit a known feature" wizard. The tab allows the user to select how far in each dimension, from a TDE where a known feature is identified, the system looks to find other occurrences of the same known feature. In one embodiment, the dimension combo box 980 contains a two-dimensional X and Y selection. The sliding scale 982 represents the dimension value, and the sliding scale 984 represents a cluster count. Specifying different cluster ranges for each dimension allows the user to account for peculiarities of the data. For example, if the vertical scale of an image is not the same as the horizontal scale, then a user could enter adjusted values to the range to attempt to get the desired cluster area.

FIG. 49 is a screenshot showing the "Actions" tab 952 of the "create or edit a known feature" wizard. The user can select the action to be performed when a known feature is identified. A combo box 990 contains a list of actions; in this application, the possible actions are playing a system sound, painting a pixel and no action. In one embodiment a user may select sound in order to alert the user when an instance of the known feature is found in the digital data. A user may select paint in order to identify those areas, in a selection of digital data, that a known feature has been identified.

Figure 50:
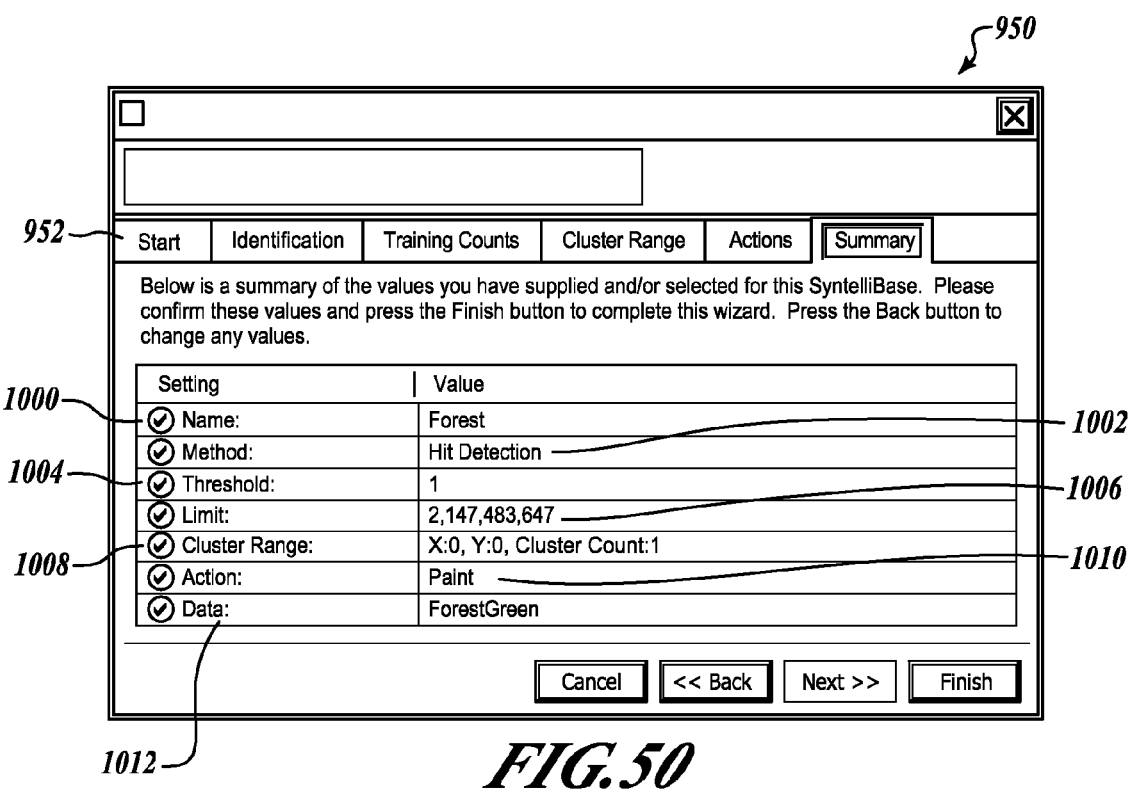
FIG. 50 shows a screenshot of a review of the known feature properties previously selected.

FIG. 50 is a screenshot showing the "Summary" tab 952 of the "create or edit a known feature" wizard. In the table, the name of the known feature forest is selected, shown in row 1000. The method of detection is hit detection, shown in row 1002. The threshold is set to 1 at row 1004. The limit is set to 2,147,483,647, shown in row 1006. The cluster range is set at X:0, Y:0, cluster count: 1, shown in row 1008. The action on detection is set as paint, shown in row 1010. The data is set as forest green, shown in row 1012.

FIG. 51 is a screenshot showing an image 1020 of a forest with a selected area 1028. The layout of this screen was described in FIG. 42. The screen 900 also contains smaller "thumbnails" of other pictures loaded into a system 1030. Mouse position and color values 1022 are shown based on the cursor location, as is common in the art. Layers 1026 of the picture 1020 are listed. The selected area 1028 is what a user has set as a region of interest, and what will be trained as the known feature forest in FIGS. 52-56.

Figure 52:
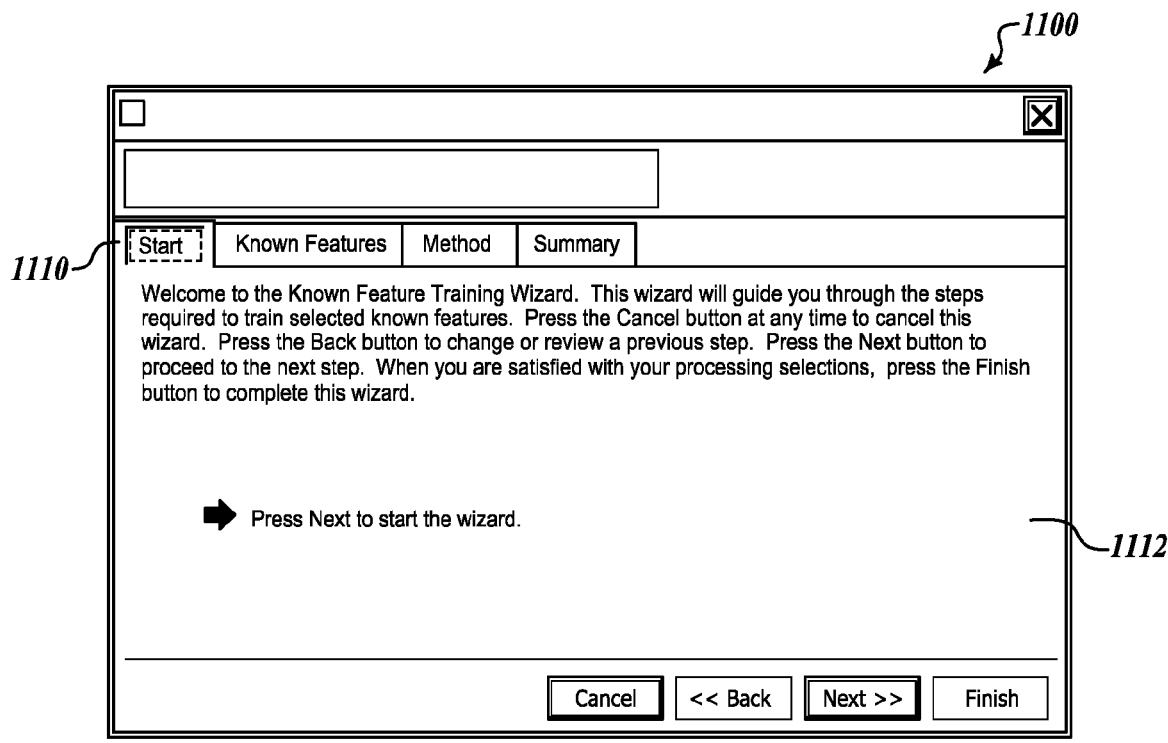
FIG. 52 shows a screenshot of an introduction screen for a training wizard.

FIG. 52 is a screenshot showing the "Start" tab 1110 of the "known feature training" wizard. The training wizard will guide a user through the steps to train selected known features. At this point a user will call on a previously setup known feature and identify that known feature on a section of digital data in order to train the system.

Figure 53:
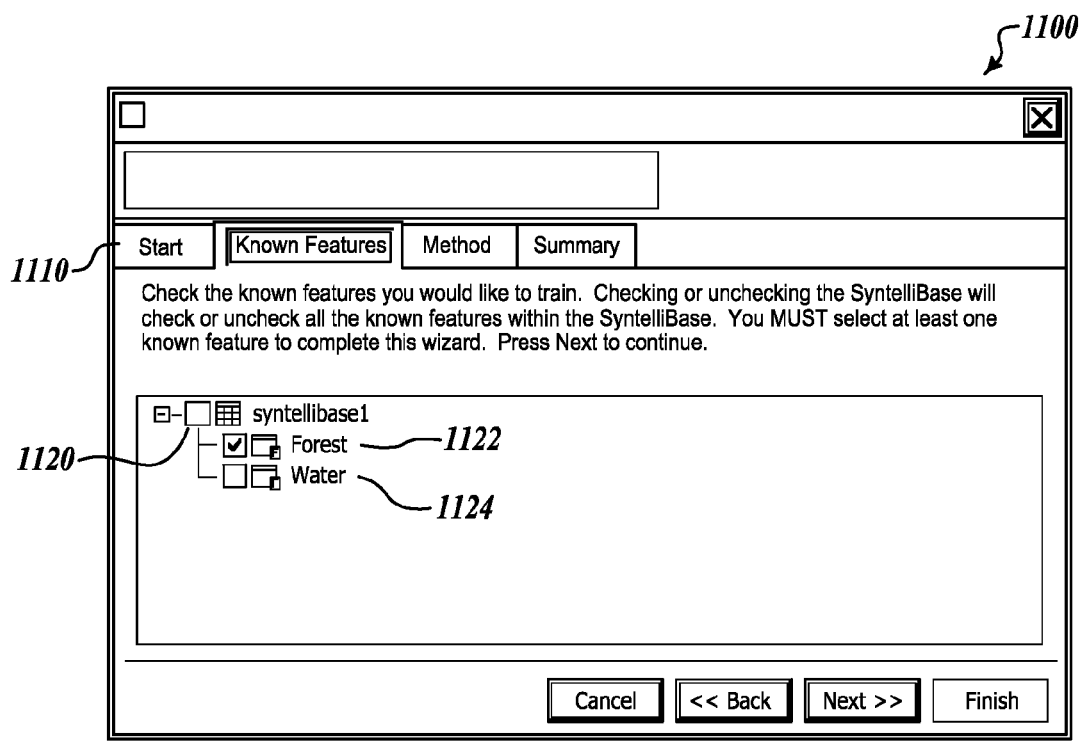
FIG. 53 shows a screenshot of the selection of forest as a known feature from the datastore.

FIG. 53 is a screenshot showing the "Known Features" tab 1110 of the "known feature training" wizard. There is a list 1120 showing the first datastore. The list contains a known feature water 1124 and a known feature forest 1122. Both water and forest were setup in the "create or edit a known feature" wizard In this example, forest 1122 is selected. If multiple datastores are open, the user can choose to train known features in multiple datastores.

Figure 54:
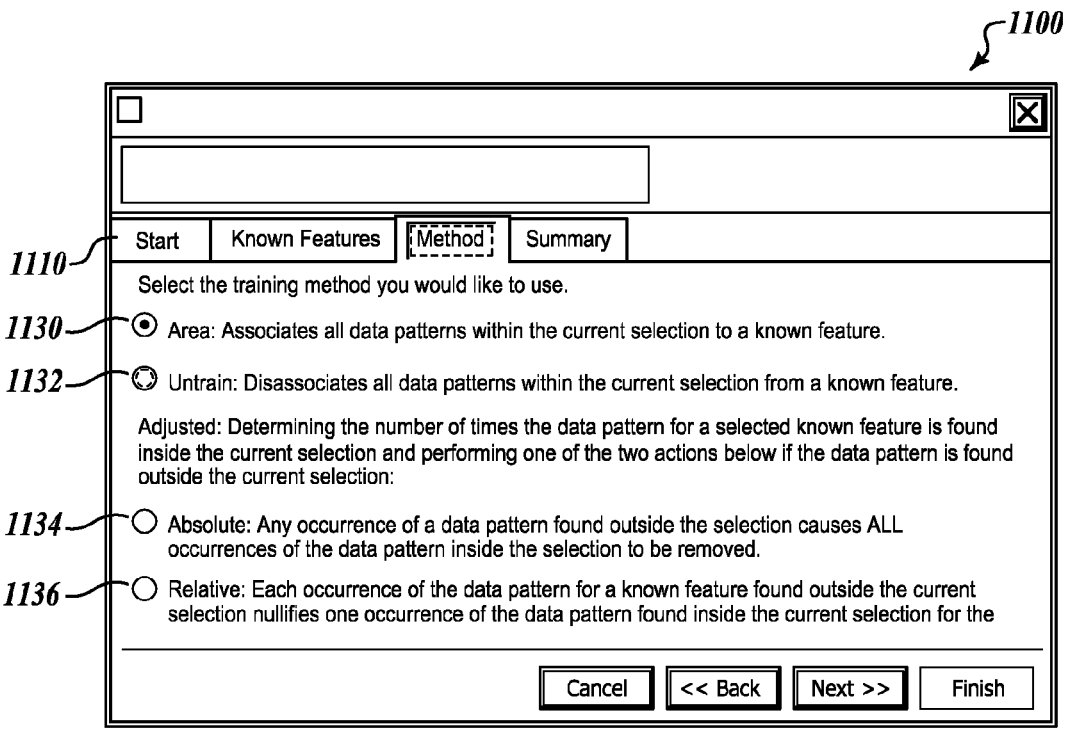
FIG. 54 shows a screenshot of the selection of an area training option.

FIG. 54 is a screenshot showing the "Method" tab 1110 of the "known feature training" wizard. There is a series of radio buttons next to four choices of training methods: area training 1130, untraining 1132, absolute adjusted training 1134 or relative adjusted training 1136. At this point a user selects the method of training that is optimal for the selected modality, submodality and sample quality.

Figure 55:
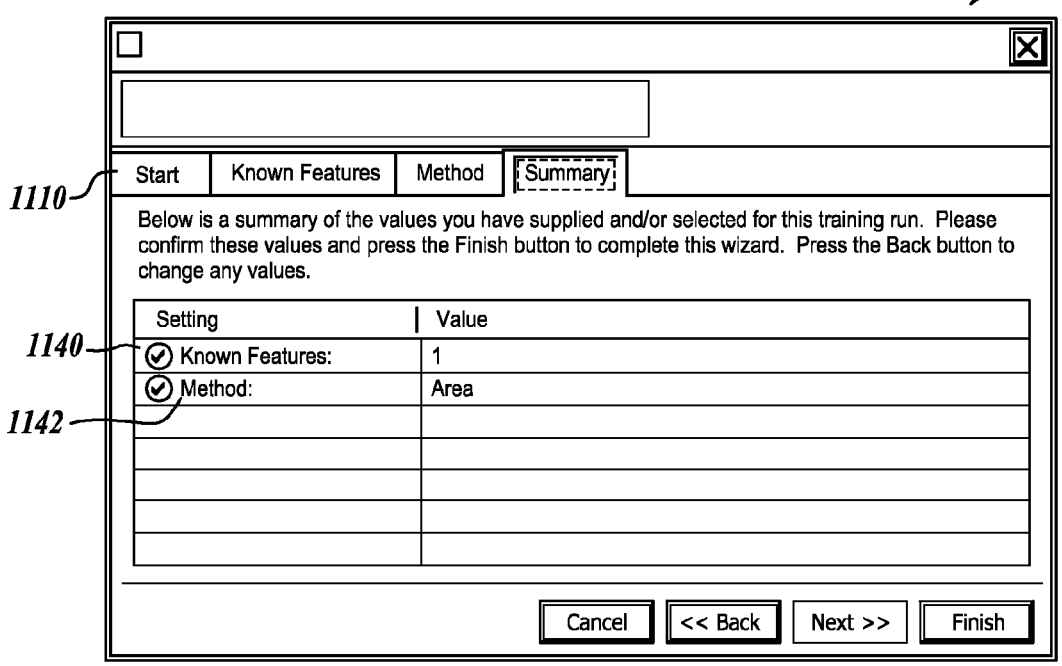
FIG. 55 shows a screenshot of a review of the training properties previously selected.

FIG. 55 is a screenshot showing the "Summary" tab 1110 of the "known feature training" wizard. The table contains the number of known features 1140, which is one in this example. In this example, the method of training is area training, see row 1142.

Figure 56:
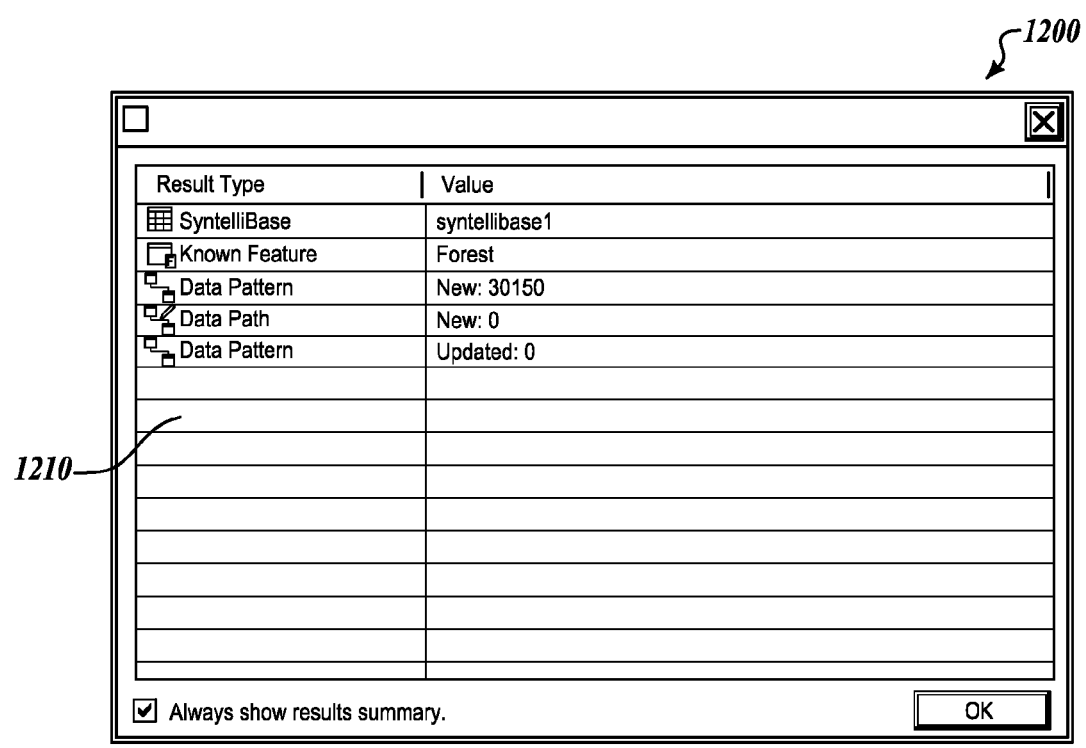
FIG. 56 shows a screenshot of the results of training.

FIG. 56 is a screenshot showing the results of training. After a user selects the finish button in FIG. 55, the datastore is trained according to the user's selections. The table 1210 shows the results. The datastore selected was "SyntelliBase1" (the default name assigned to the datastore by the application and can be changed by the user), the known feature trained was forest, and the number of new data patterns found was 30,150. The number of new data paths found was 0. The number of updated data patterns found was 0. A user may elect not to see the summary of the results.

The new and updated patterns were generated as a result of executing the algorithms selected above in FIG. 39 on the pixel values in the selected area of the image in FIG. 51 using the process illustrated above in FIGS. 23-33. The algorithm values for each pixel were calculated and taken as a set; those values generated a data pattern associated with the known feature in the web. In the selected area of the image, the actual area probably contained an assortment of trees, shrubs, and other vegetation. The 30,150 patterns that were found reflected the algorithm values from these different materials, and all of those patterns were associated with the known feature "forest".

Figure 57:
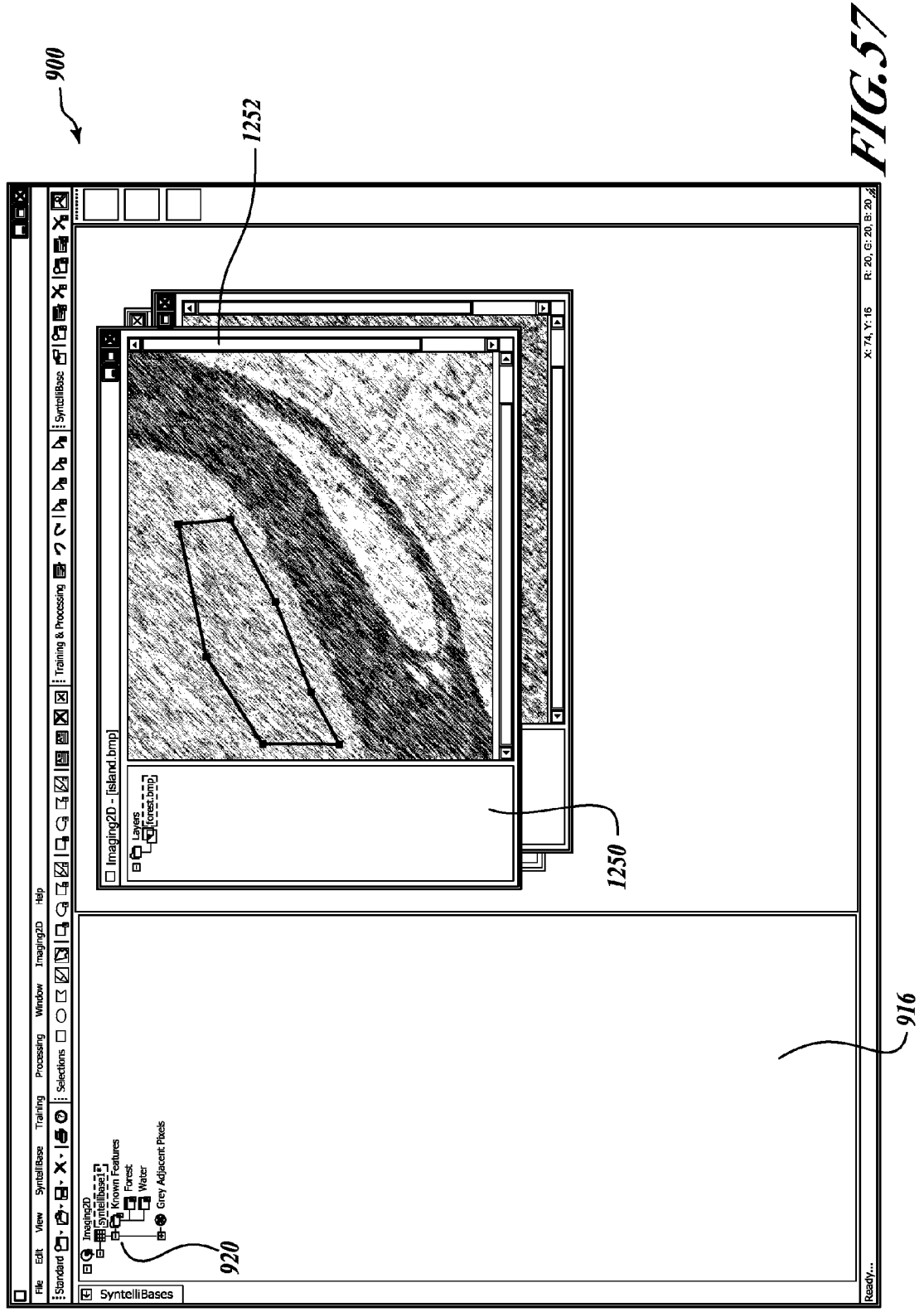
FIG. 57 shows a screenshot of an image with an area of forest.

FIG. 57 is a screenshot showing an image with an area of forest and an area of water. The forest is represented by the lighter shaded area, and the water by the darker shaded area. FIG. 57 relates to FIG. 51 in that the same pictures are loaded. However, a different picture 1252 is now selected. The picture 1252 shows an area of forest selected, the selected area is shown with black lines. This is the area a user has defined, in this example, as an area known to be the known feature "forest."

Figure 58:
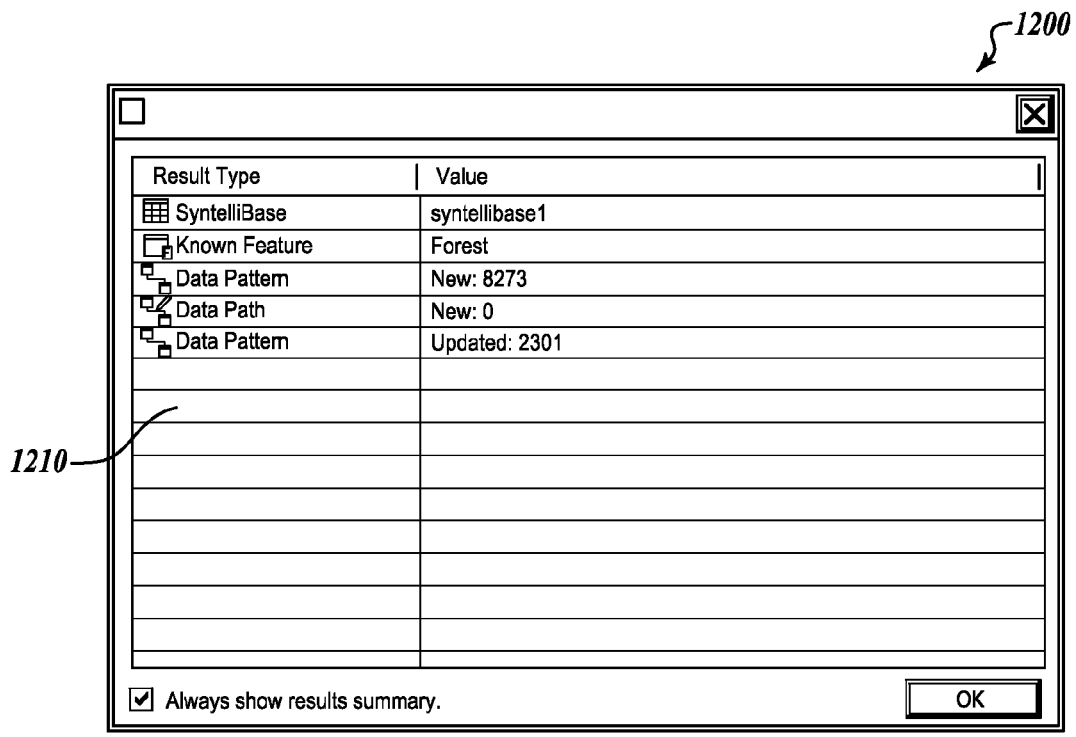
FIG. 58 shows a screenshot of the results of training the image in FIG. 57.

FIG. 58 is a screenshot showing the results of training the area selected in FIG. 57. The training event added 8,273 new data patterns and updated 2,301 data paths.

The training process on this image generated patterns using the process illustrated in FIGS. 23-33 on the selected area of the image in FIG. 57. 2,301 patterns were previously associated with the known feature, and those associations were updated. 8,273 data patterns were not previously associated with the known feature, and those associations were created.

Figure 59:
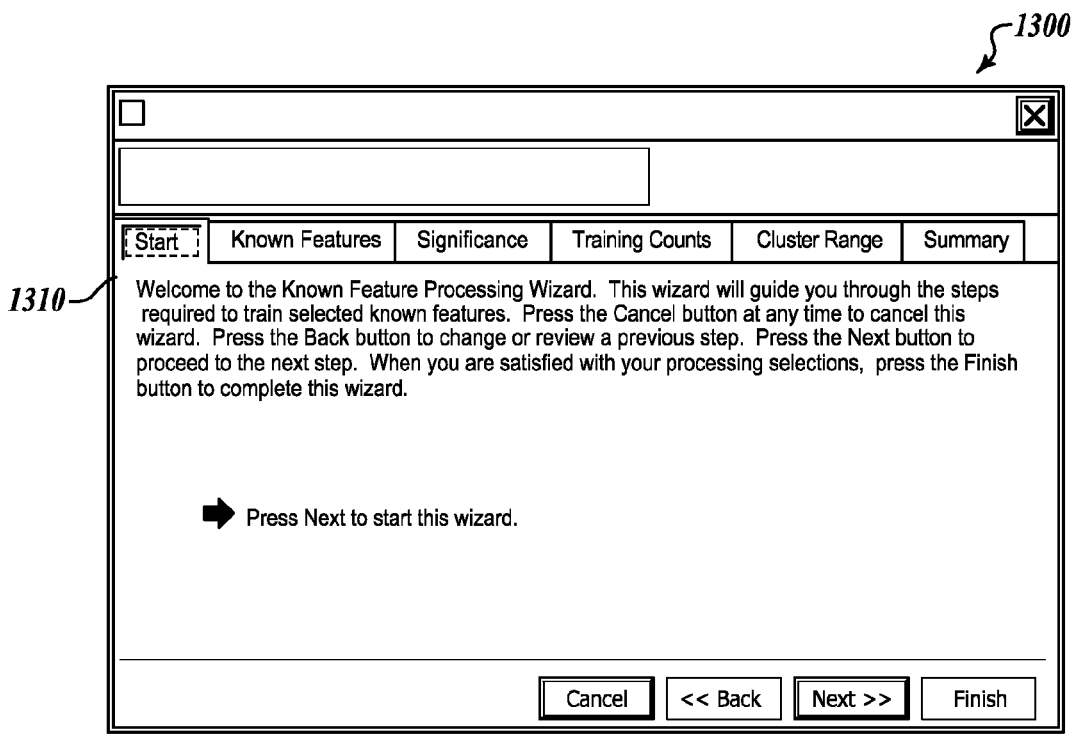
FIG. 59 shows a screenshot of a wizard for known feature processing.

FIG. 59 is a screenshot showing the "Start" tab 1310 of the "known feature processing" wizard, which guides a user through the steps in this application to process selected known features. This wizard allows a user to process a new section of digital data using the previously trained known features in order to determine if the known feature is present.

Figure 60:
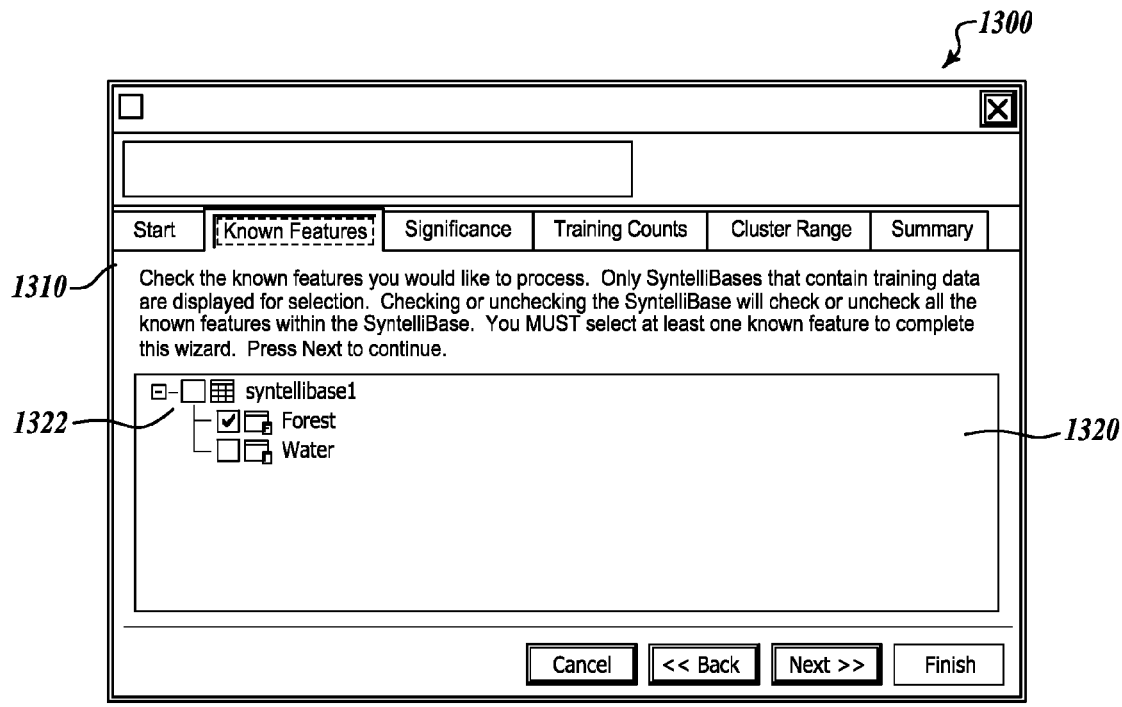
FIG. 60 shows a screenshot of a list of known features a user may want to process.

FIG. 60 is a screenshot showing the "Known Features" tab 1310 of the "known feature processing" wizard. Table 1320 shows all of the datastores that contain training data. In this example, SyntelliBase1, shown in row 1322, is available. A user can check or uncheck any or all listed known features within the particular datastore that the user wants to identify. In this example, forest is selected.

Figure 61:
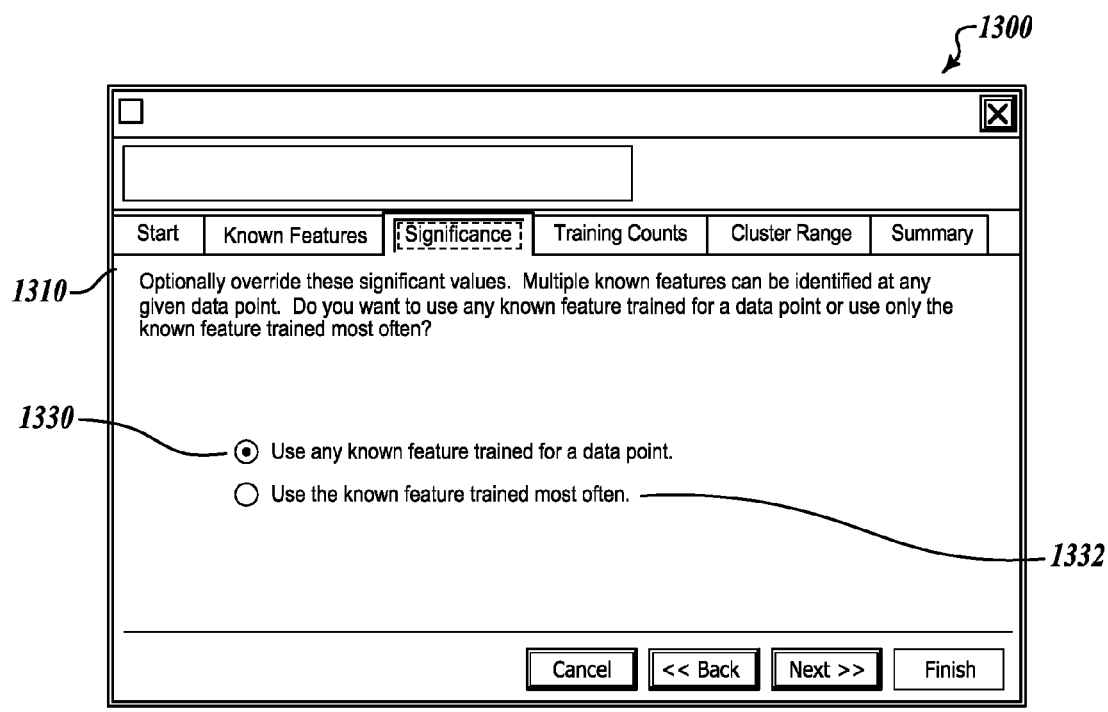
FIG. 61 shows a screenshot of a known feature's significance value.

FIG. 61 is a screenshot showing the "Significance" tab 1310 of the "known feature processing" wizard. The user can optionally override significance processing options. The option button 1330 allows for identification for any known feature trained for a specific data point, and option button 1332 identifies the known feature trained most often. In some cases, multiple known features can be identified at any given data point. The first option allows all of those known features to be identified. The second option allows only the feature that was most often associated with the given data pattern to be identified.

Figure 62:
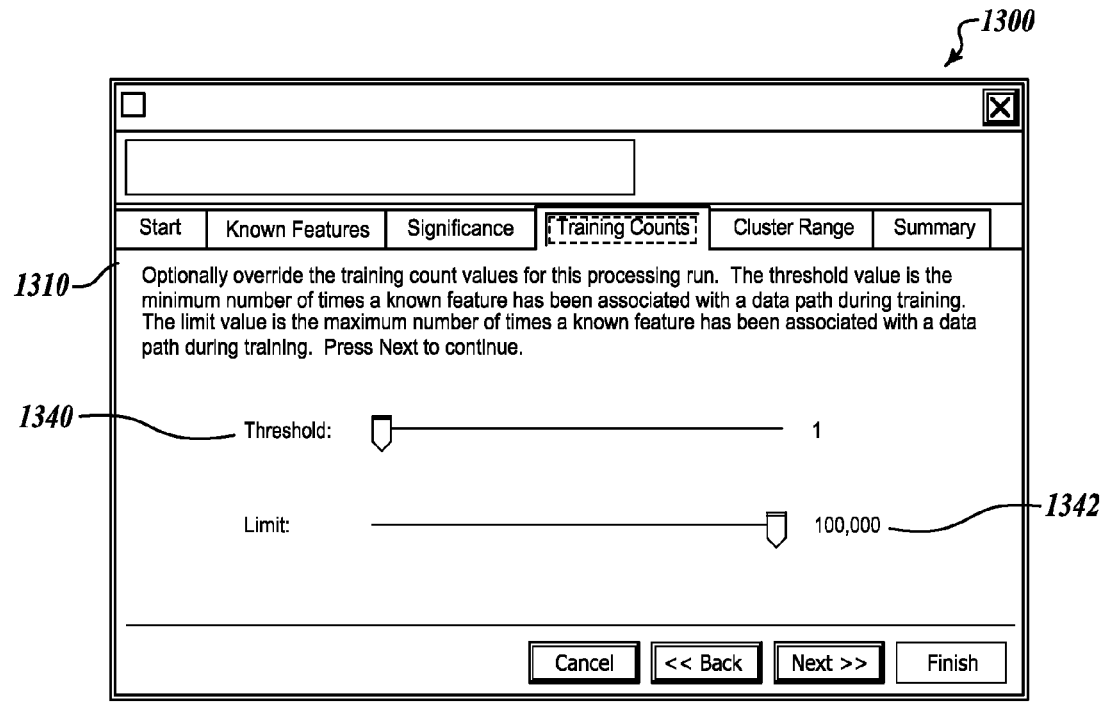
FIG. 62 shows a screenshot of optional overrides for the training count values for a single processing run.

FIG. 62 is a screenshot showing the "Training Counts" tab 1310 of the "known feature processing" wizard. The user can optionally override the training count values for processing. The threshold values, shown as a sliding scale 1340, are the minimum number of times a known feature must have been associated with the synaptic path during training to be identified. A limit value, shown as a sliding scale 1342, is the maximum number of times a known feature could have been associated with the synaptic path during training to be identified.

Figure 63:
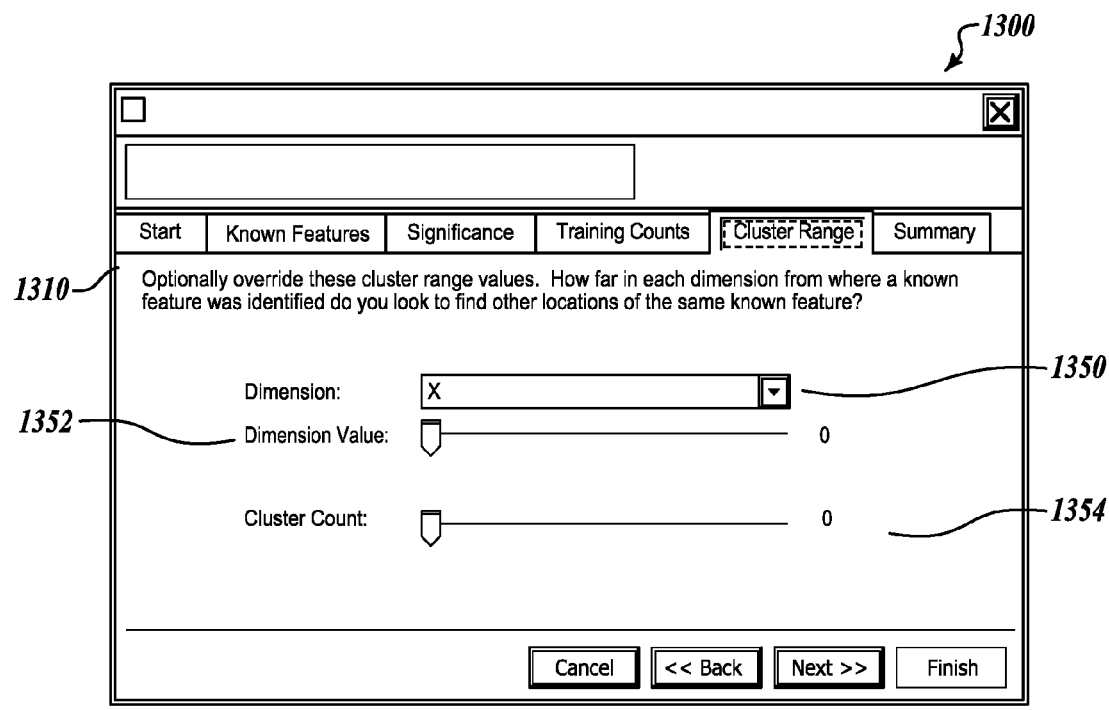
FIG. 63 shows a screenshot of optional overrides for the cluster values for a single processing run.

FIG. 63 is a screenshot showing the "Cluster Range" tab 1310 of the "known feature processing" wizard. A user can optionally override cluster range values. The combo box 1350 allows the user to select a particular dimension. In a two-dimensional image, the combo box 1350 can contain the X-dimension and the Y-dimension. The dimension value is selected on the sliding scale 1352. The cluster count is selected on a sliding scale 1354.

Figure 64:
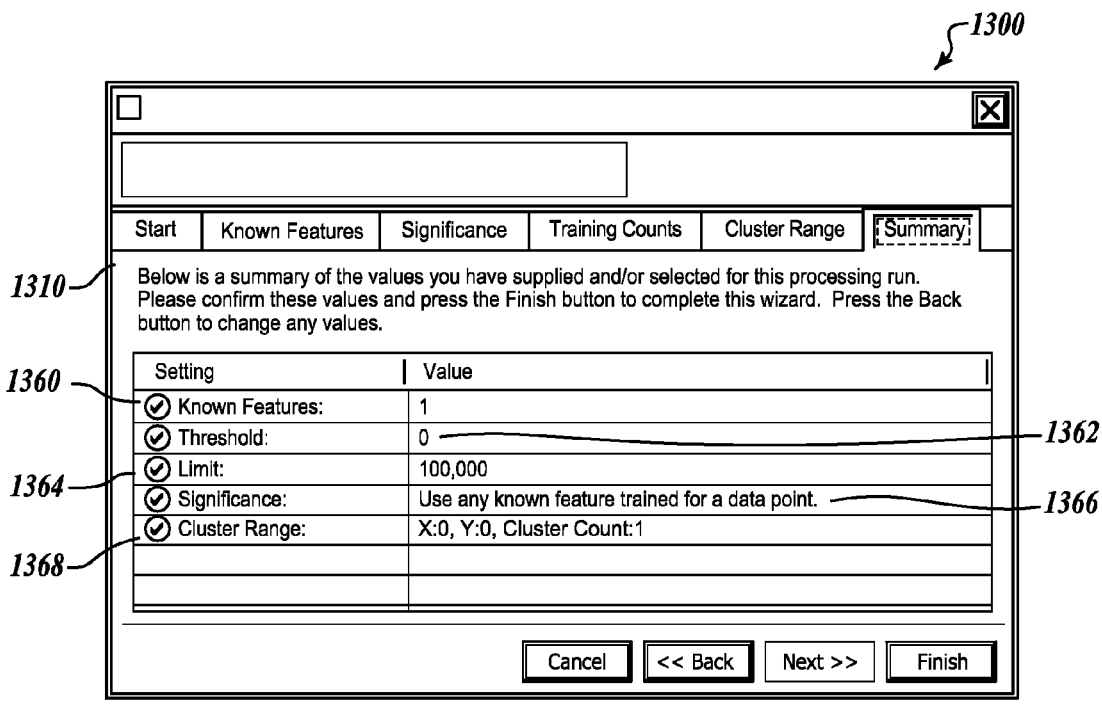
FIG. 64 shows a screenshot of a review of the processing properties previously selected.

FIG. 64 is a screenshot showing the "Summary" tab 1310 of the "known feature processing" wizard. The values include the number of known features 1360, the threshold override 1362, the limit override 1364, the significance override 1366 and cluster range override 1368.

Figure 65:
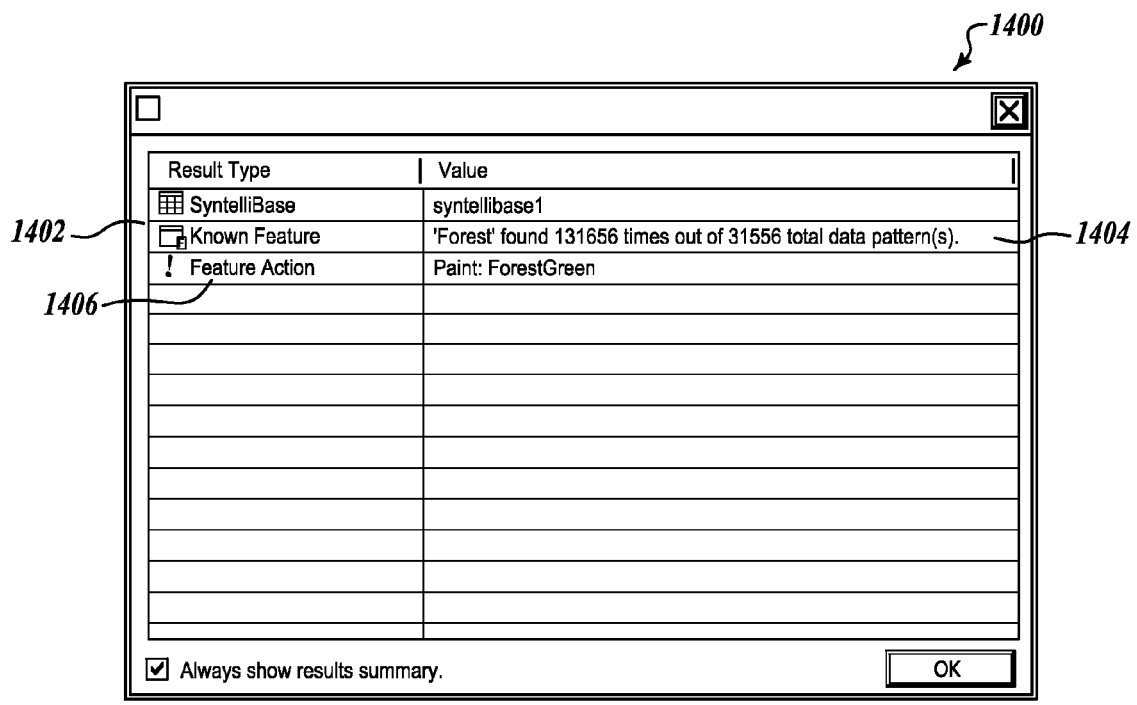
FIG. 65 shows a screenshot of the results of processing.
Figure 66:
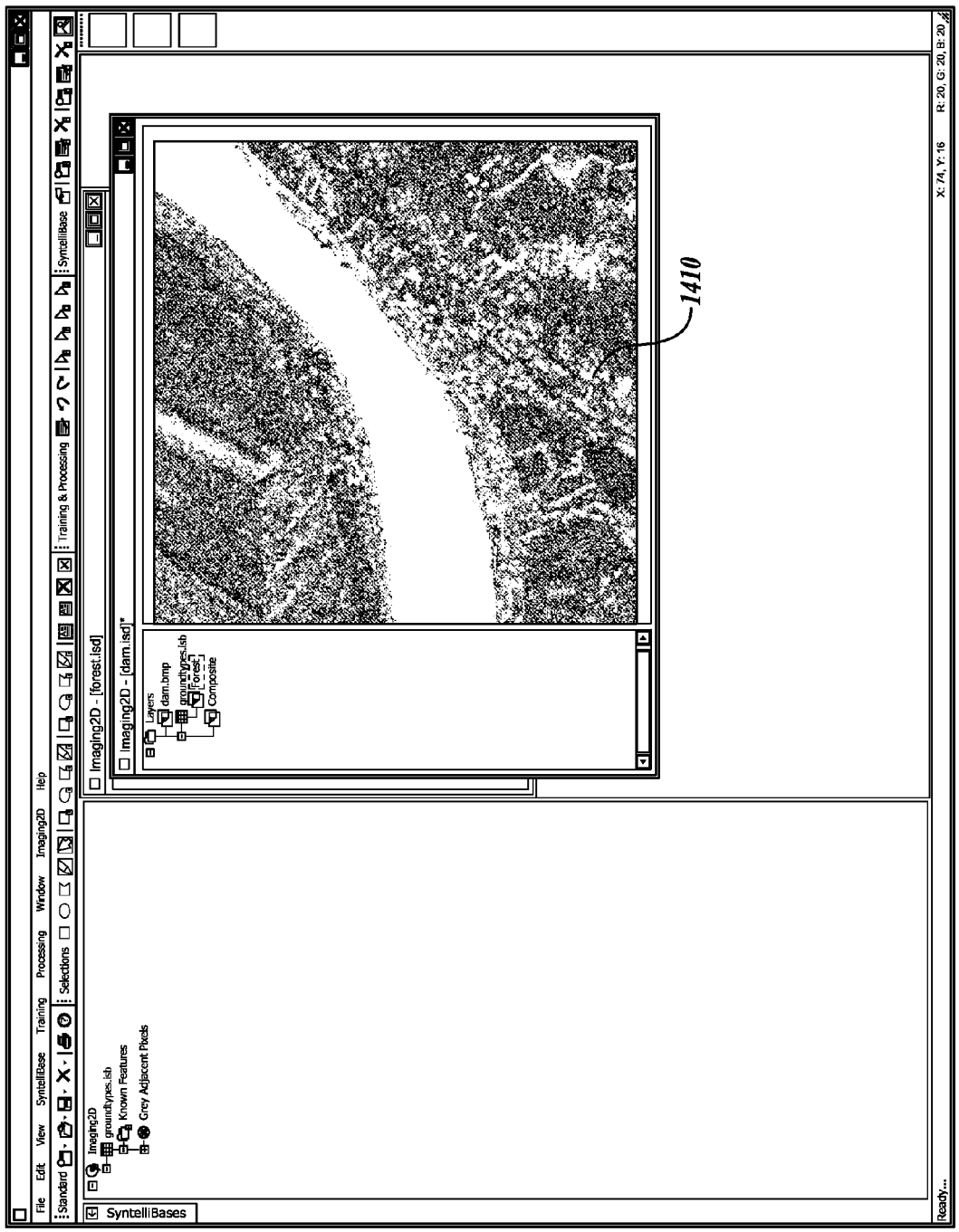
FIG. 66 shows a screenshot of an image with a green layer showing pixels the system identified as forest.

FIG. 65 is a screenshot showing a processing result summary. The processing result summary shows that out of the 31,556 patterns encountered for the known feature forest, one or more of those occurred 131,656 times, and that the known feature action to paint one or more pixels forest green was performed. The data patterns were generated using the process discussed above for FIG. 34 using the algorithms the user selected in FIG. 39. These algorithms are, and must be, the same algorithms that are used in training above in FIGS. 56 and 58. When the same algorithm set is executed and returns the same set of values, the same data pattern is developed as was developed in training, and the known feature associated with the data pattern is identified. In the processing in FIG. 65, there were 131,656 pixels identified as the known feature "forest" because 31,556 of the data patterns developed matched data patterns associated with that known feature. A layer for the identified known feature forest was added to the image. This is further shown in FIG. 66.

Figure 67:
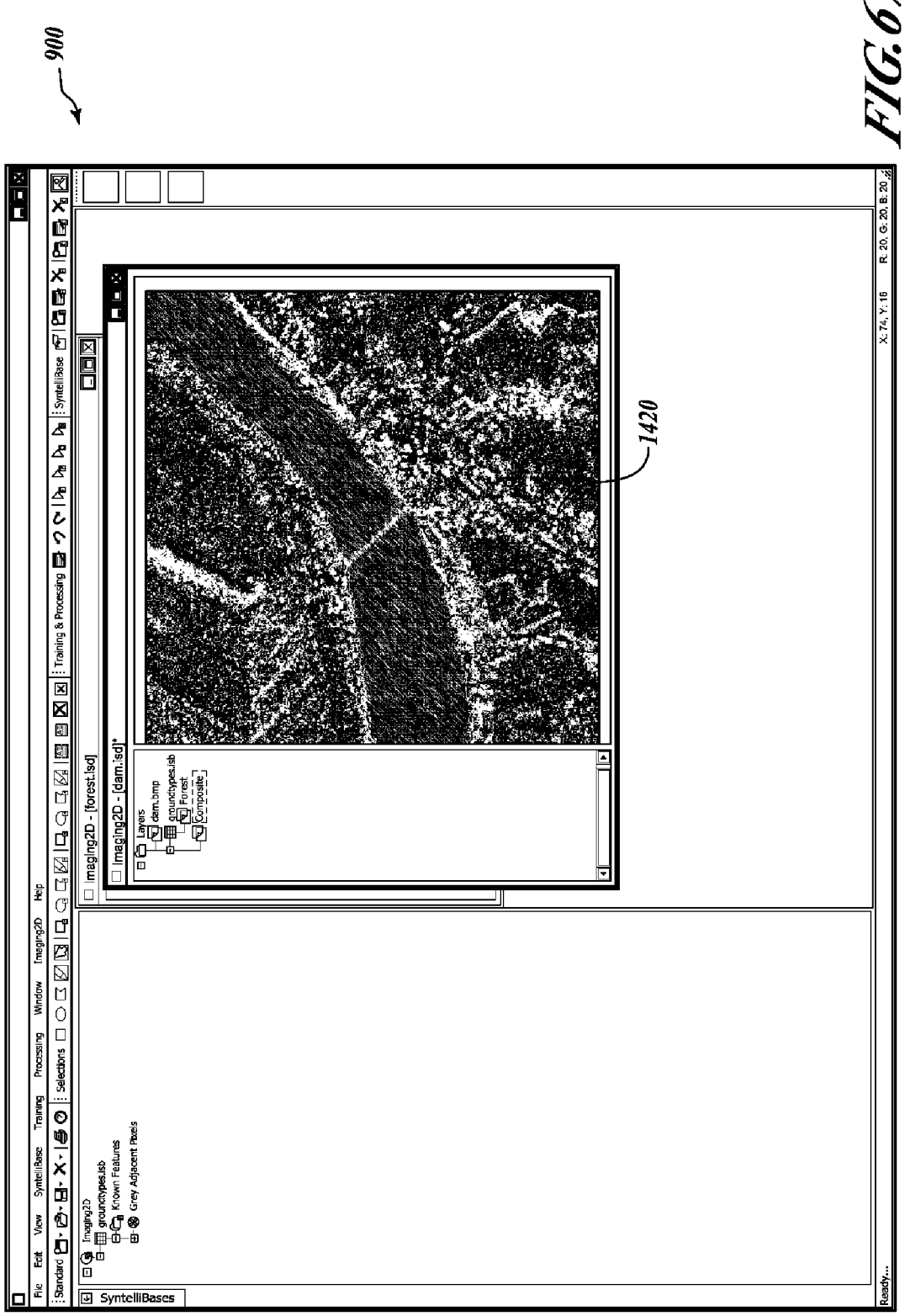
FIG. 67 shows a screenshot of a composite image with a forest layer.

FIG. 67 is a screenshot showing the result of processing. The image 1420 contains 131,656 pixels that should be painted forest green because they were identified as forest in processing.

Figure 68:
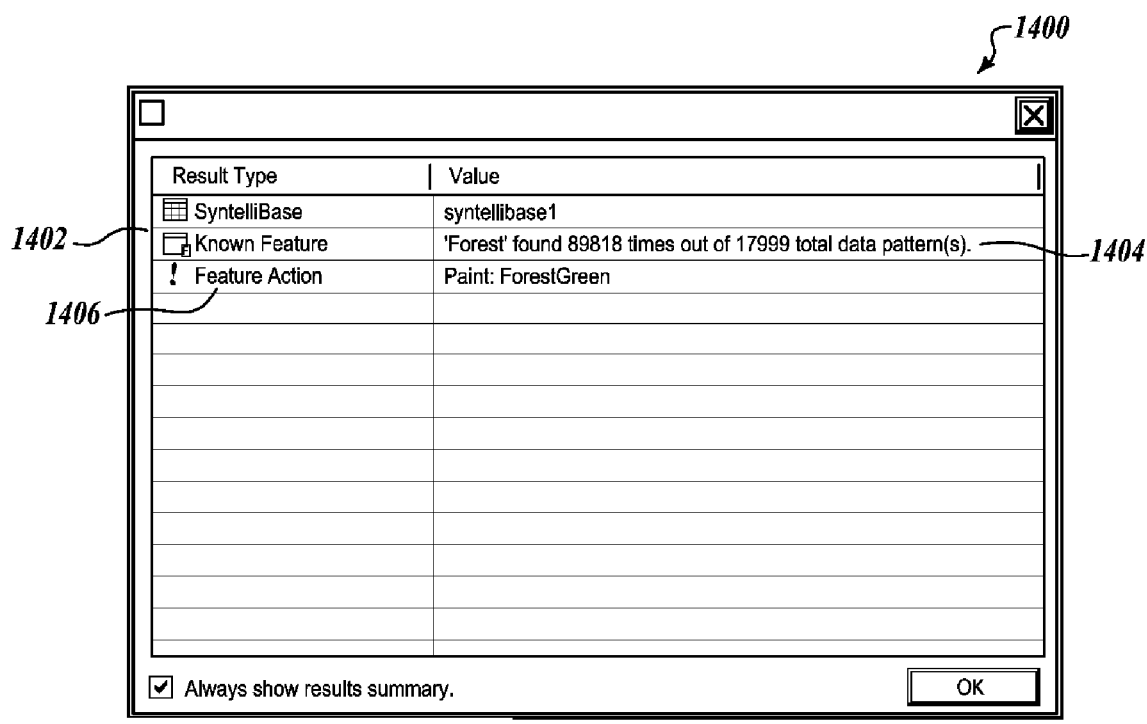
FIG. 68 shows a screenshot of a second image processed for the forest known feature.

FIG. 68 is a screenshot showing the processing of a second image, again looking for the known feature forest. The datastore 1402 used in the processing was SyntelliBase1. The known feature forest 1404 was found 89,818 times using 17,999 total data patterns. The known feature action 1406 was to paint the forest "forest green." Because these images are black and white, the pixels that would be painted forest green are printed black.

Figure 69:
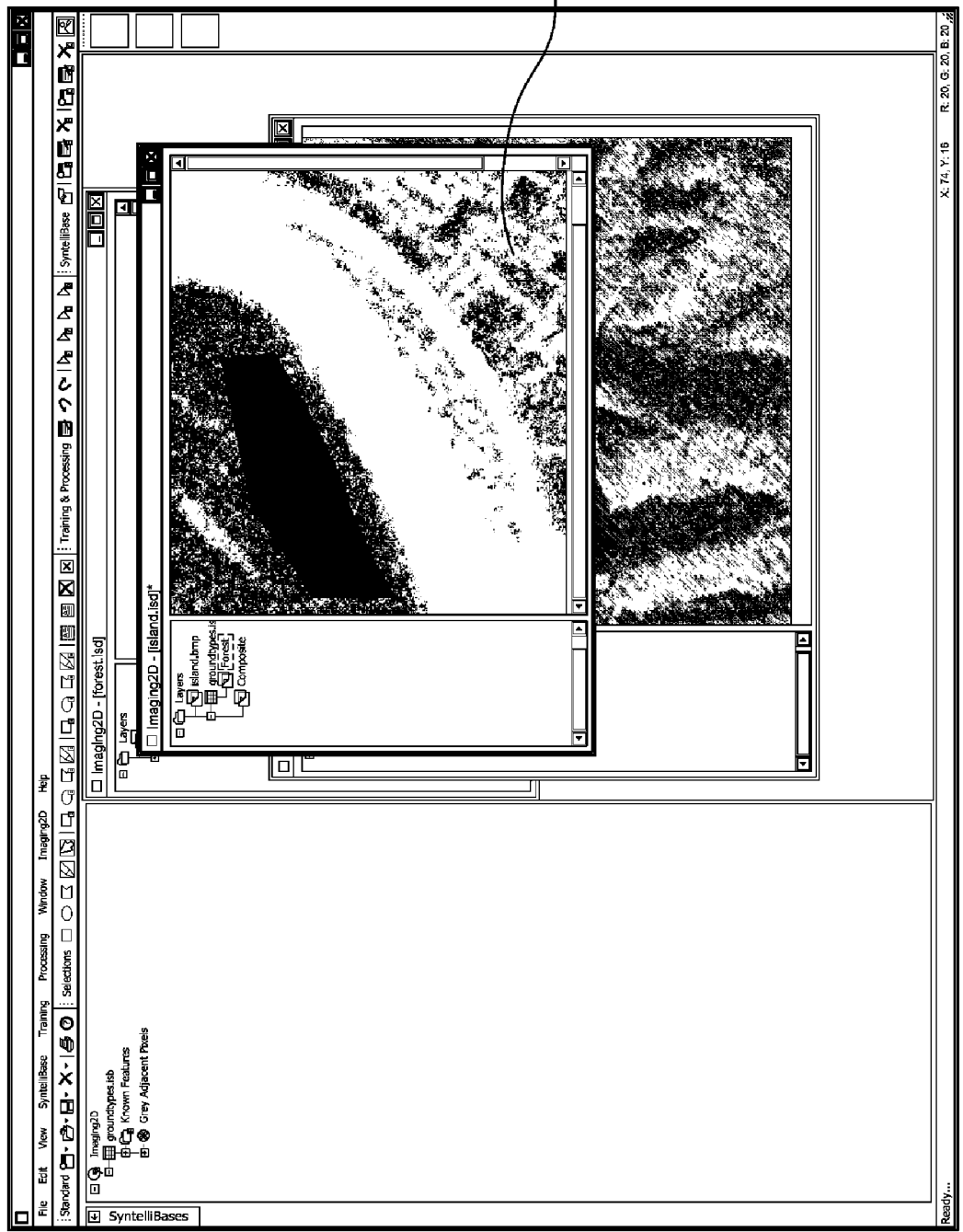
FIG. 69 shows a screenshot of an image with a green layer showing pixels the system identified as the known feature forest.

FIG. 69 is a screenshot showing an image 1430 with a layer for the known feature forest showing pixels that the application identified as forest. The solid block of forest green in the image shows the area where training occurred on the area selected in FIG. 57. This area is completely identified as forest because the user selected that area and instructed the application that the area is forest.

Figure 70:
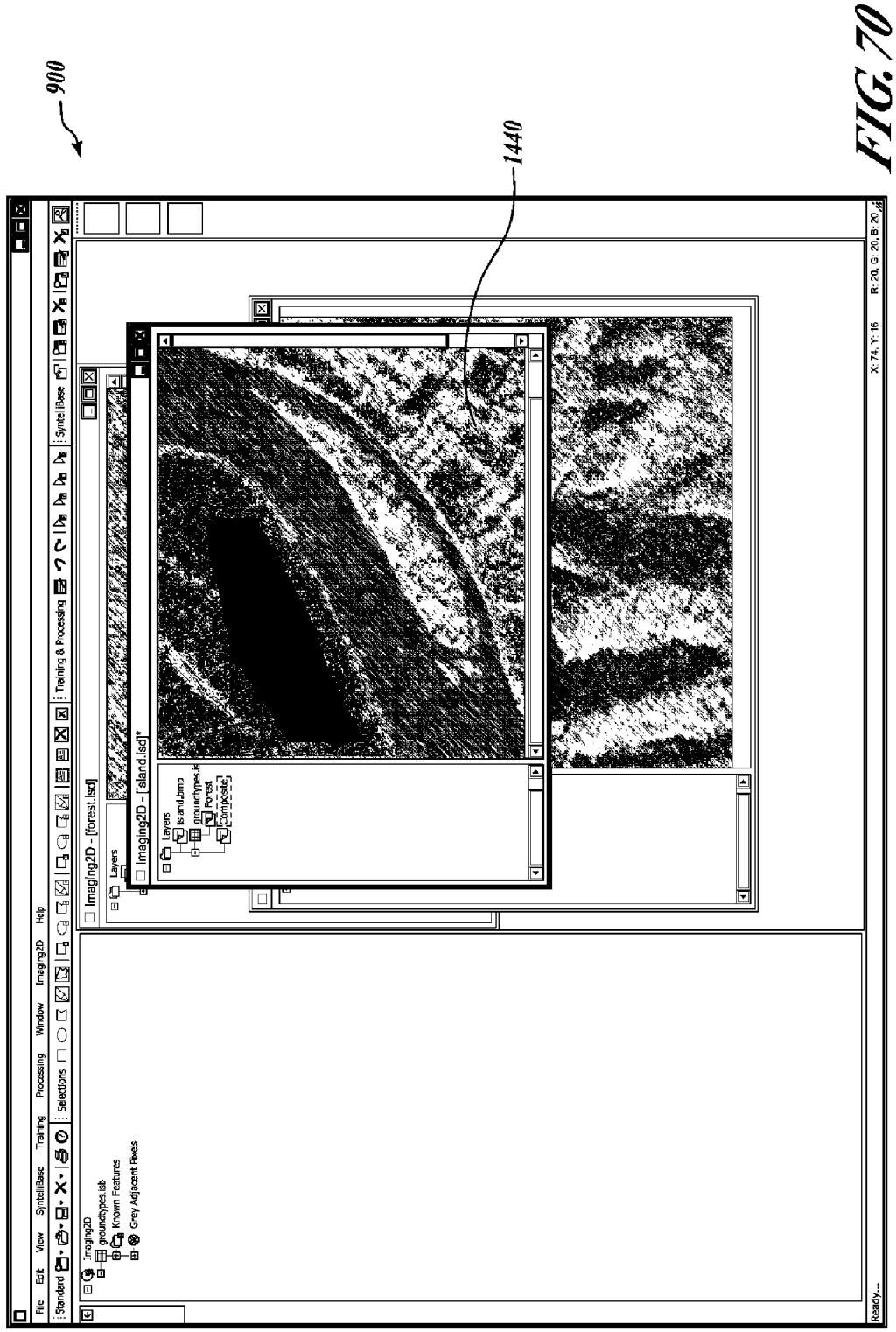
FIG. 70 shows a screenshot of a composite image with a forest layer.

FIG. 70 is a screenshot showing a composite image containing the original picture FIG. 57 and the layer where the application identified forest shown in FIG. 69.

Figure 71:
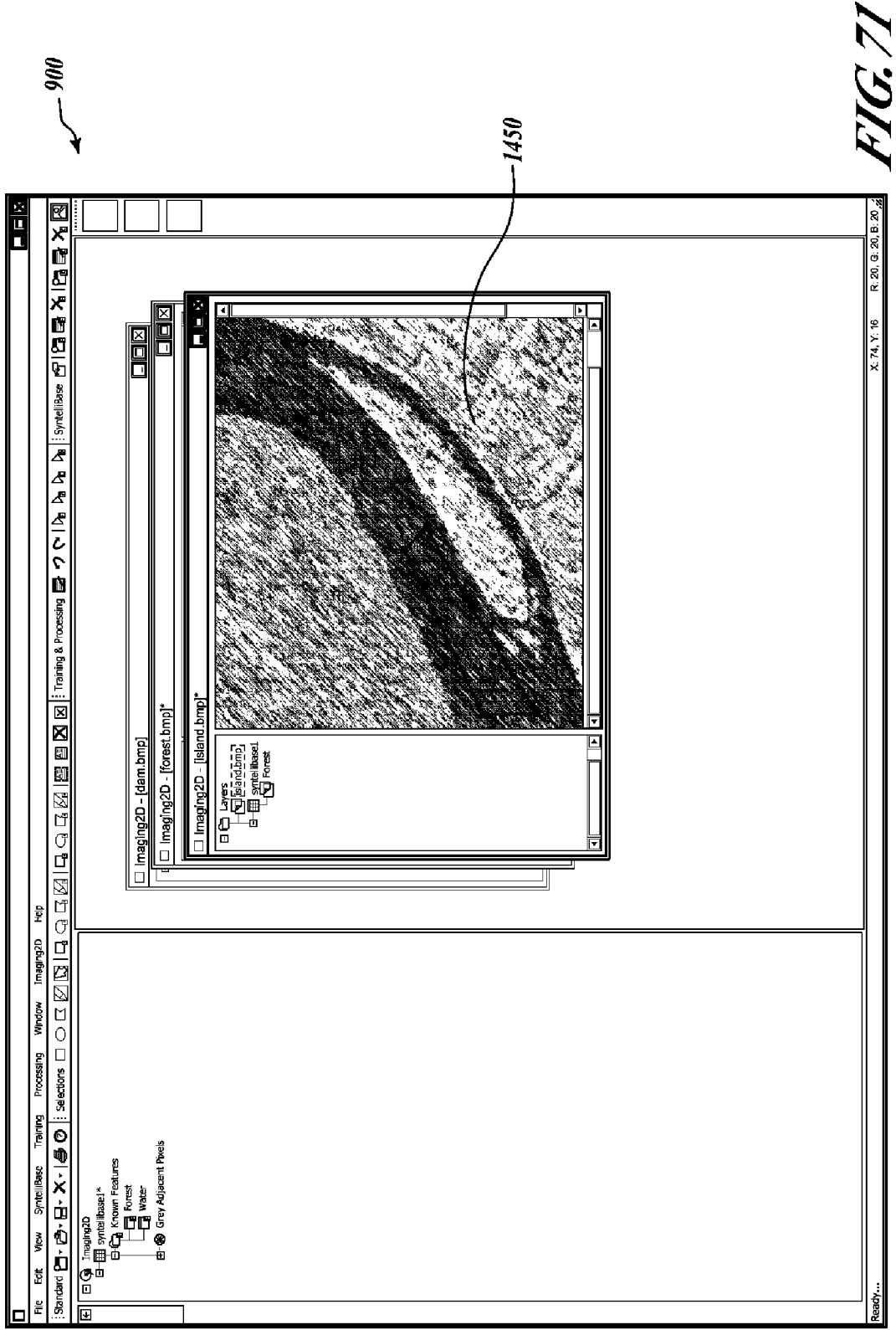
FIG. 71 shows a screenshot of an image with water selected.

FIG. 71 is a screenshot showing an image 1450 with an area of water selected.

Figure 72:
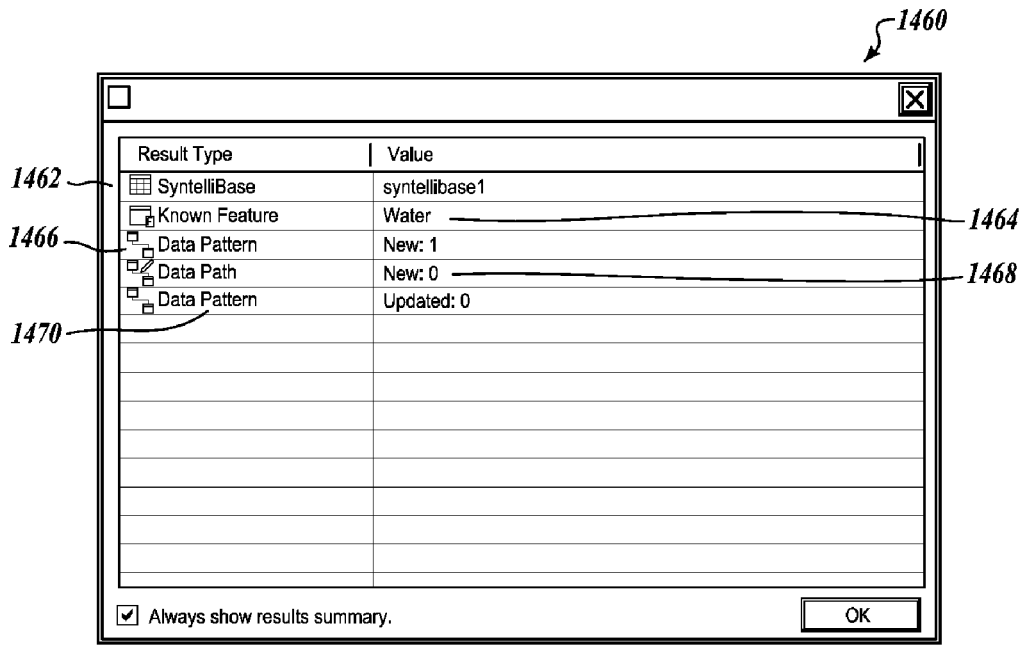
FIG. 72 shows a screenshot of the results of training using the previously selected water.

FIG. 72 is a screenshot showing the results of training the selection in FIG. 71 as the known feature water. The training of the selection added 1 data pattern. In FIG. 71, the pixels in the selected area are uniform. When the algorithms selected in FIG. 34 above are executed on the pixels in the selected area, a single data pattern is the result.

Figure 73:
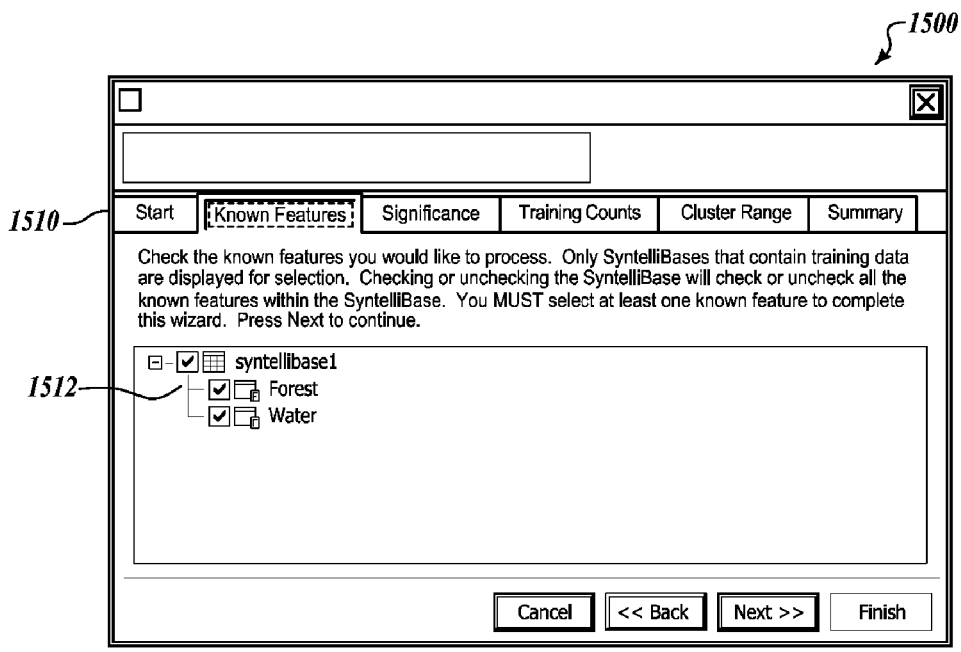
FIG. 73 shows a screenshot of an image with both forest and water.

FIG. 73 is a screenshot showing the processing of both the forest and the water known features for an image. By selecting both forest and water 1512, the user is asking the system to identify both of those features during processing.

Figure 74:
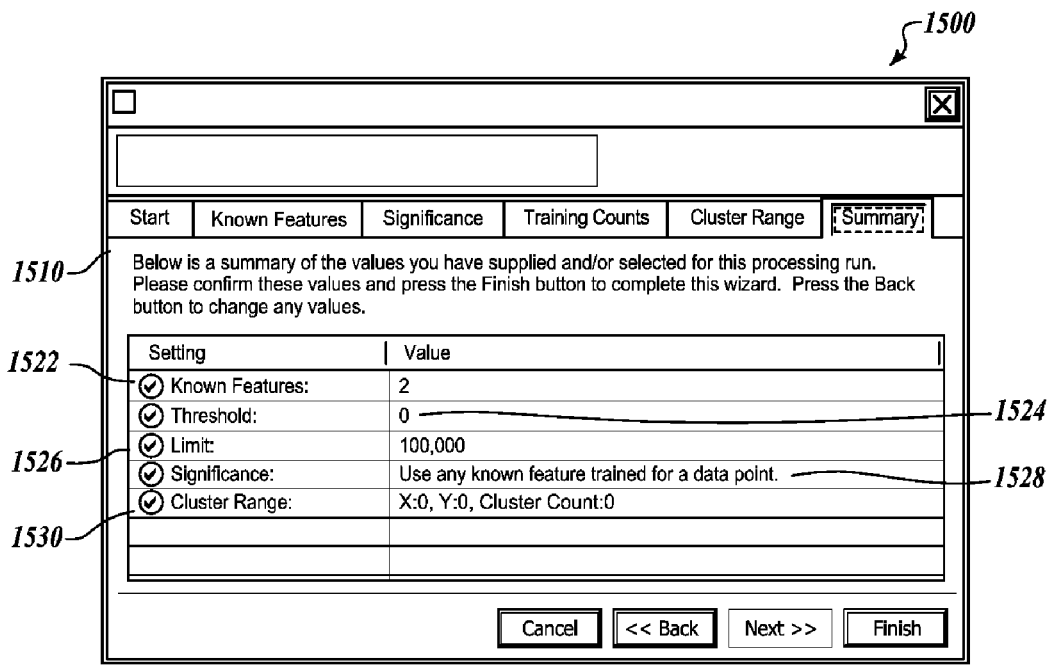
FIG. 74 shows a screenshot of a review of the processing properties previously selected.

FIG. 74 is a screenshot showing a summary of the values that a user has supplied or has selected for processing the image in FIG. 71. In this example, the number of known features selected, shown in row 1522, was 2. The threshold override, shown in row 1524, was 0. The limit override, shown in row 1526, was 100,000. The significance override, shown in row 1528, was to use any known feature trained for a TDE. The cluster range override, shown in row 1530, was set to X:0, Y:0, cluster count: 0.

Figure 75:
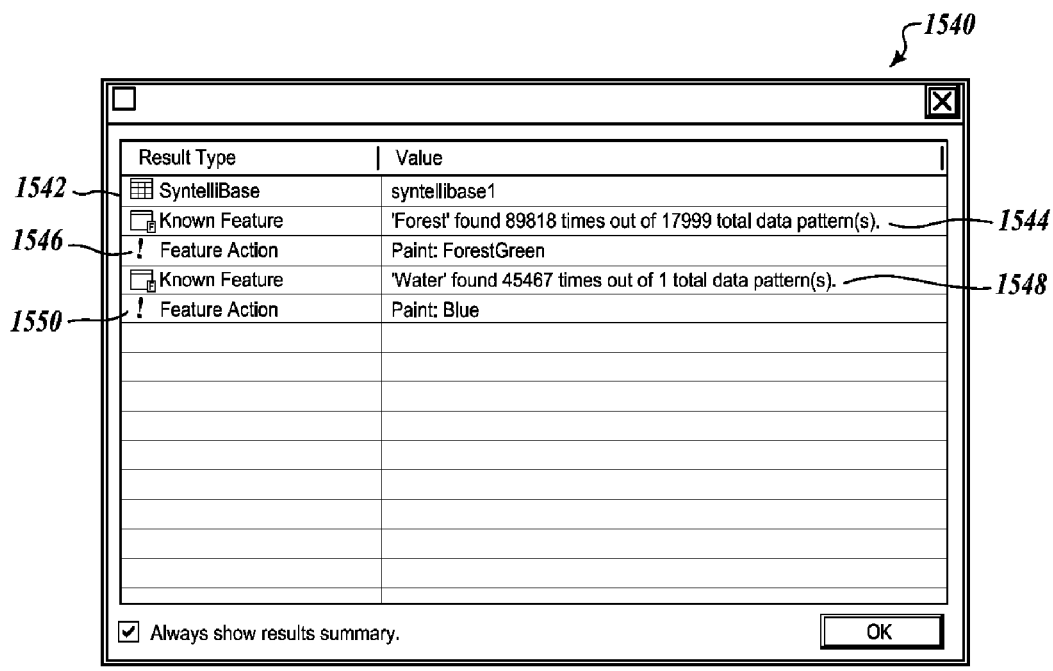
FIG. 75 shows a screenshot of the results of processing.

FIG. 75 is a screenshot showing the summary of the processing set up in FIG. 74. In this image, the datastore used, shown in row 1542, was SyntelliBase1. A known feature forest, shown in row 1544, was found 89,818 times using 17,999 data patterns trained as forest. The known feature action, shown in row 1546, was to paint the identified pixels forest green. The known feature water, shown in row 1548, was found 45,467 times using one data pattern trained as water. The known feature action, shown in row 1550, was to paint the identified pixels blue. In one embodiment, the system does not remove all previous designated data, but actually processes "all" the data each time it processes.

Figure 76:
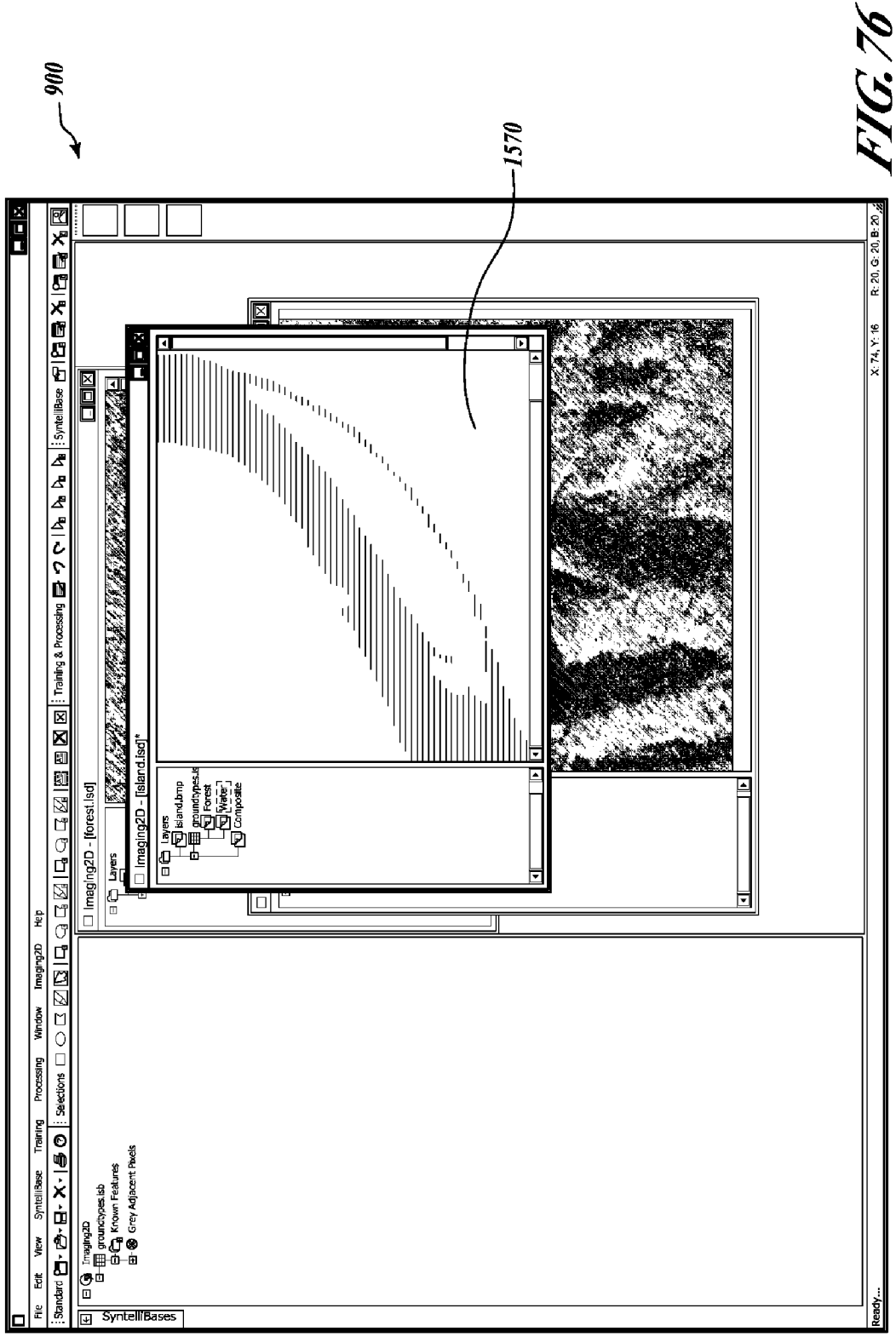
FIG. 76 shows a screenshot of a water layer.

FIG. 76 is a screenshot showing the layer of water found in the image. Image 1570 shows the pixels found to be water and painted blue; however in these images, water is represented as striped black lines.

Figure 77:
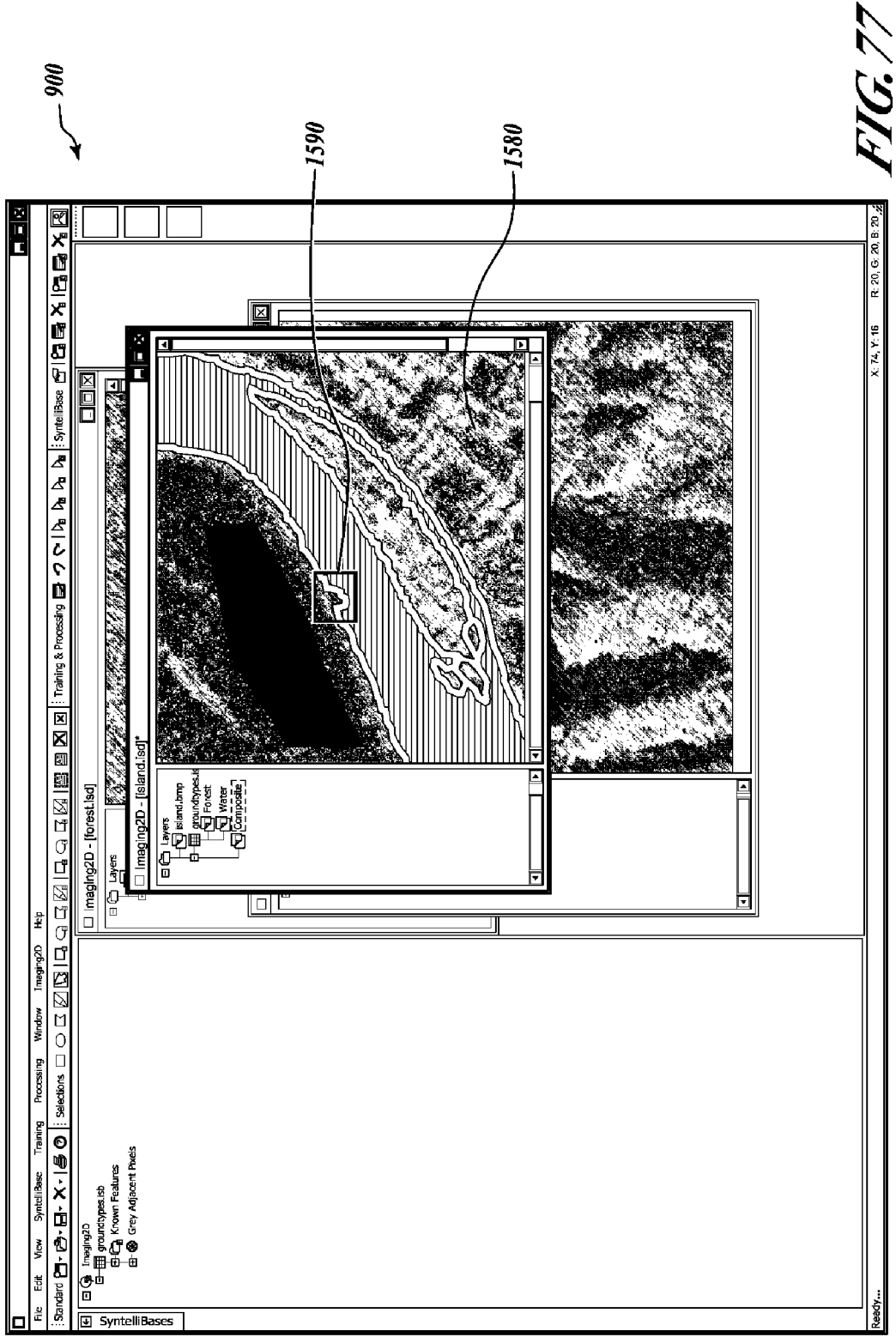
FIG. 77 shows a screenshot of a composite image with both the forest layer and the water layer.

FIG. 77 is a screenshot showing the composite image showing the original image, water and forest. Image 1580 shows the areas where water is identified in blue and the areas where forest is identified in forest green. In this image, the contrast is shown between water, the dark forest area and the white spots, which are unidentified. Note the area 1590 that is not marked as water. In the original image 76, that area appeared to be water, but the processing system has detected characteristics that indicate it is not water like the rest of the image. It is likely to be an area of shallow water or shoreline.

In an embodiment not shown, any displayed anomalies that are not identified (previously trained features) are painted to distinguish them from trained features.

In still another embodiment, a visual or audible alarm may be a function that is associated with a known feature. Thus, during an analysis of a data set, an alarm would be triggered if a previously known feature was found.

Figure 78:
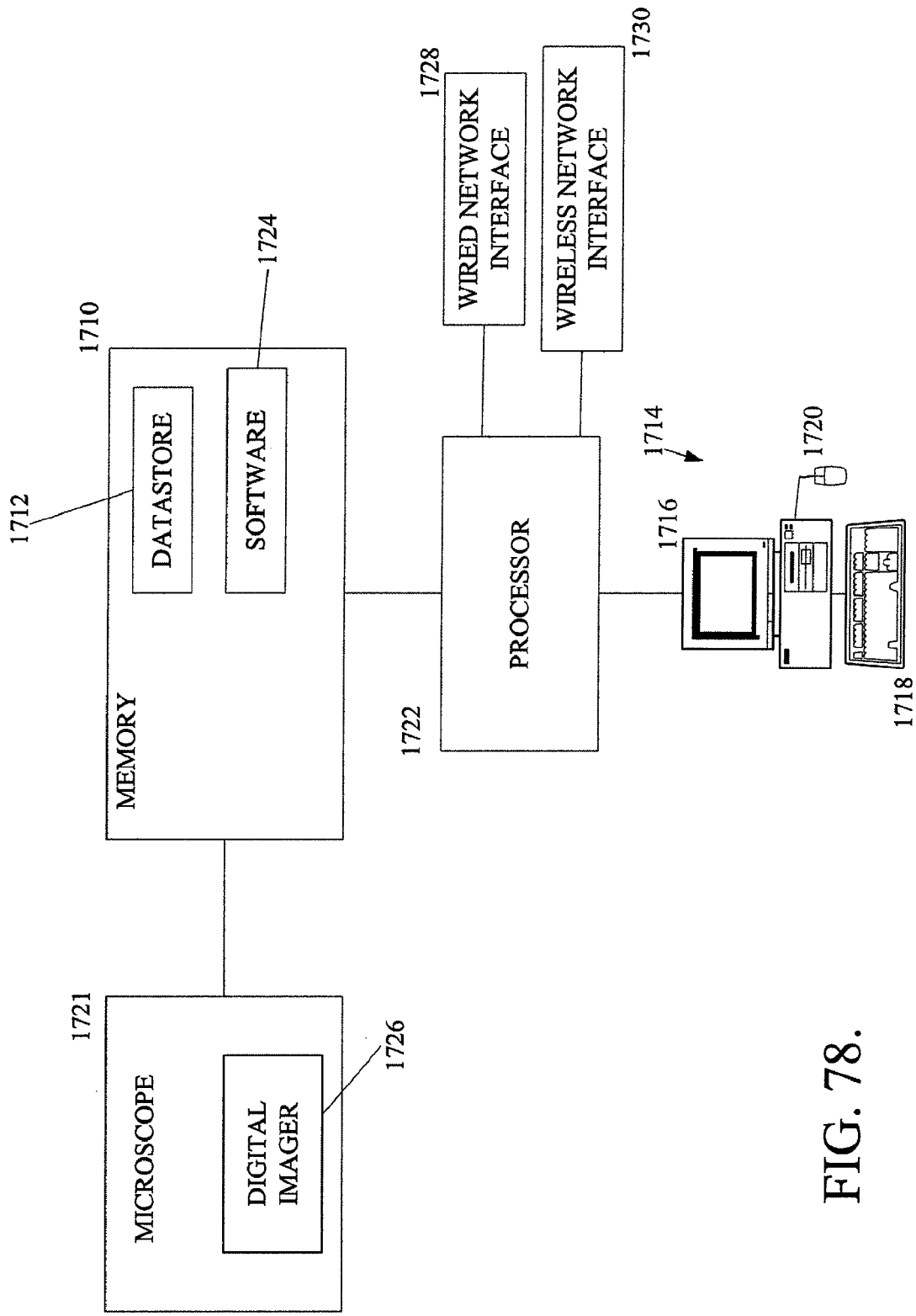
FIG. 78 is a block diagram of a system for data analysis and detection of avian influenza virus formed in accordance with an As used herein, the term "synaptic path" refers to a plurality of values from all of the algorithms. The synaptic path is used to reach a synaptic leaf based on calculations for target data elements.

FIG. 78 is a block diagram of a system 1700 for data analysis and detection of avian influenza virus formed in accordance with an embodiment of the invention. In an example embodiment, the system 1700 includes a memory 1710, a data store 1712 stored in the memory 1710 that contains processed results of a first series of algorithms processed on a first data set corresponding to an aspect of a first biological sample known to contain avian influenza virus that is an H5N1 strain in an example embodiment. The system 1700 also includes a user interface 1714, a processor 1722 in data communication with the user interface and the memory 1710, and a software module 1724 for storage in the memory 1710 and operable by the processor 1722. In an example embodiment, the user interface 1714 includes a display 1716, a keyboard 1718, and a pointing device 1720, such as a computer mouse. However, in other embodiments, the user interface may include fewer or additional components than those shown. In an example embodiment, the system 1700 is structured and functions in similar fashion to the system described with respect to FIGS. 1 and 2.

In an example embodiment, the software module 1724 includes a first component configured to run a second series of algorithms on a second data set corresponding to an aspect of a second biological sample to generate an algorithm value cache. The software module also includes a second component configured to compare the algorithm value cache to the processed results of the first series of algorithms to generate a match result as well as a third component configured to perform a processing action based on the generated match result. In an example embodiment, the first series of algorithms and the second series of algorithms include at least one of the algorithms mentioned with respect to the example described in relation to FIGS. 23-33 and/or feature identification for avian influenza virus is performed in similar fashion to the example described with respect to FIG. 34.

In an example embodiment, the first and second data sets correspond to digital photographs of the first and second biological samples respectively. The first and second biological samples may include at least one of a blood sample, a lachrymal fluid sample, a saliva sample, a fecal sample, a buccal fluid sample, an apocrine fluid sample, an eccrine fluid sample, or a mucus sample, for example. In an example embodiment, the digital photographs are taken at a magnification level and having a resolution that allows cellular abnormalities associated with an avian influenza viral infection to be seen. Additional photographs may also be taken at other magnification levels and resolutions such as at a magnification level and resolution level that allows avian influenza virus components to be seen, for example. In an example embodiment, the first and/or second biological samples are from a bird. In an additional embodiment, the first and/or second biological samples are from a human.

The system 1700 also optionally includes a microscope 1721 having a digital imaging component 1726 in data communication with the memory 1710. In other embodiments, the digital imaging component 1726 is in data communication with the processor 1722 rather than the memory 1710. The system 1700 also optionally includes a wired network interface 1728 and/or a wireless network interface 1730 for communicating over a wired or wireless network (not shown) with a remote user or server (not shown). The network interfaces 1728, 1730 are used for communicating results of testing to a field technician, a pathologist, and/or specialized governmental or intergovernmental agencies in some embodiments. In an example embodiment, the system 1700 is a portable system.

Although not shown for clarity, in some embodiments, the processor 1722 includes a component configured to identify avian influenza virus in a second data set corresponding to an aspect of a second biological sample, the component including first, second, and third subcomponents. In an example embodiment, the first sub-component is configured to generate an algorithm value cache for the second data set by running a second series of algorithms on the second data set. The second sub-component is configured to generate a match result by comparing the generated algorithm value cache with the results of the first series of algorithms processed on the first data set. The third sub-component is configured to perform a processing action based on the generated match result.

Although not shown for clarity, in an example embodiment, the first sub-component configured to generate an algorithm value cache includes first, second, third, and fourth sub-elements. The first sub-element is configured to retrieve a first target data element in the second data set. The second sub-element is configured to process the second series of algorithms on a target data area for the retrieved first target data element. The third sub-element is configured to direct the first sub-element and the second sub-element to retrieve additional target data elements in the second data set and process the second series of algorithms on a target data area for the retrieved additional target data elements. The fourth sub-element is configured to store the results of the processed second series of algorithms to generate the algorithm value cache.

In an example embodiment, a first data set is created by training the system 1700 in a similar fashion to the methods presented earlier with respect to FIGS. 3-15. The system is trained by using a first biological sample (not shown) that is sensed in some manner, such as by magnifying the biological sample and taking a digital image of the magnified sample. In an example embodiment, digital images are taken of the first biological sample and the system is trained by having a user identify virus infected cells and/or virus components as features to be trained using algorithms that are run on the digital image to generate a synaptic web. The generated synaptic web is then stored in the datastore 1712.

After the synaptic web has been stored in the datastore 1712 as a first data set, a second data set corresponding to an aspect of the second biological sample may be analyzed by the system 1700 to determine whether avian influenza virus is present in the second biological sample to which the second data set corresponds. The second data set may be generated in many different ways. In an example embodiment, the second data set is generated using digital image data of the second biological sample. The second data set is analyzed using the results of the first series of algorithms that were processed on the first data set. In analyzing the second data set, the system 1700 generates an algorithm value cache for the second data set by running a second series of algorithms on the second set and then generates a match result by comparing the generated algorithm value cache with results of the first series of algorithms that were run on the first data set. In an example embodiment, the second series of algorithms is the same as the first series of algorithms. The system then performs a processing action based on the generated match result. In an example embodiment, identification of the avian influenza virus feature in the second biological sample is performed in a similar fashion to that described with respect to FIGS. 16-20.

In some embodiments, the processing action includes notifying a user of a match by the use of a visual and/or audible indicator. In other embodiments, the processing action includes notifying a remote user and/or server over a wired or wireless network of the match result. The processing action also includes storing the match result in the memory 1710 in some embodiments. If a wired or wireless network is not available for transmission of the match result to a remote user, the stored match result is transmitted to the remote user at a later time when a wired or wireless network becomes available. Additional embodiments include one or more sensors (not shown) for sensing information related to the second biological sample such as a bar code or radio frequency identification (RFID) tag associated with the second biological sample. In an example embodiment, the processing action is performed in a similar fashion to that described with respect to FIGS. 21 and 22.

In an example embodiment, the system 1700 is an automated detection system, with the second series of algorithms being pre-programmed into the system 1700 so that a user does not need to select them through the user interface 1714. The user simply inserts a slide containing the second biological sample into a scanning component (not shown) of the microscope 1721, and the system 1700 performs image capture using the digital imaging component 1726 followed by data analysis using the second series of algorithms and feature detection for the presence of avian flu virus by comparing the results of the second series of algorithms to the results of the first series of algorithms in the datastore 1712 to obtain a match result. In an example embodiment, the system 1700 is a hand-held system that allows the analysis and detection to occur in remote locations if necessary or to more easily allow detection in multiple locations such as point of entry to a country, point of exit from a country, and additional locations, such as at a hospital or on a farm. Using detection technology in three or more locations is used in an embodiment to minimize the spread of avian flu by using detectors at all ports of entry or exit to a country and in at least one additional location such as at a hospital or on a farm.

In some embodiments, the second biological sample is prepared using one or more methods before being processed by the system 1700. For example, the second biological sample is stained in some embodiments, and is treated with one or more chemical or biological reagents in other embodiments. In an embodiment, the second biological sample is obtained using a test strip, a slide, and/or another disposable sampling method. Example embodiments also include at least one of the following biological sampling and detection methods: iontophoresis, infrared measurement, imaging using high intensity light, x-ray imaging, magnetic resonance imaging, ultrasonic or other acoustic imaging, and laser imaging. Additional embodiments include at least one of the following technologies in generating the second data set: post catalyst reaction measurements, spectroscopic measurement, enzymatic reagents, chromatography, fluorescence imaging, cellular vibrations information, harmonic vibration data, and scent sensors.

Figure 79:
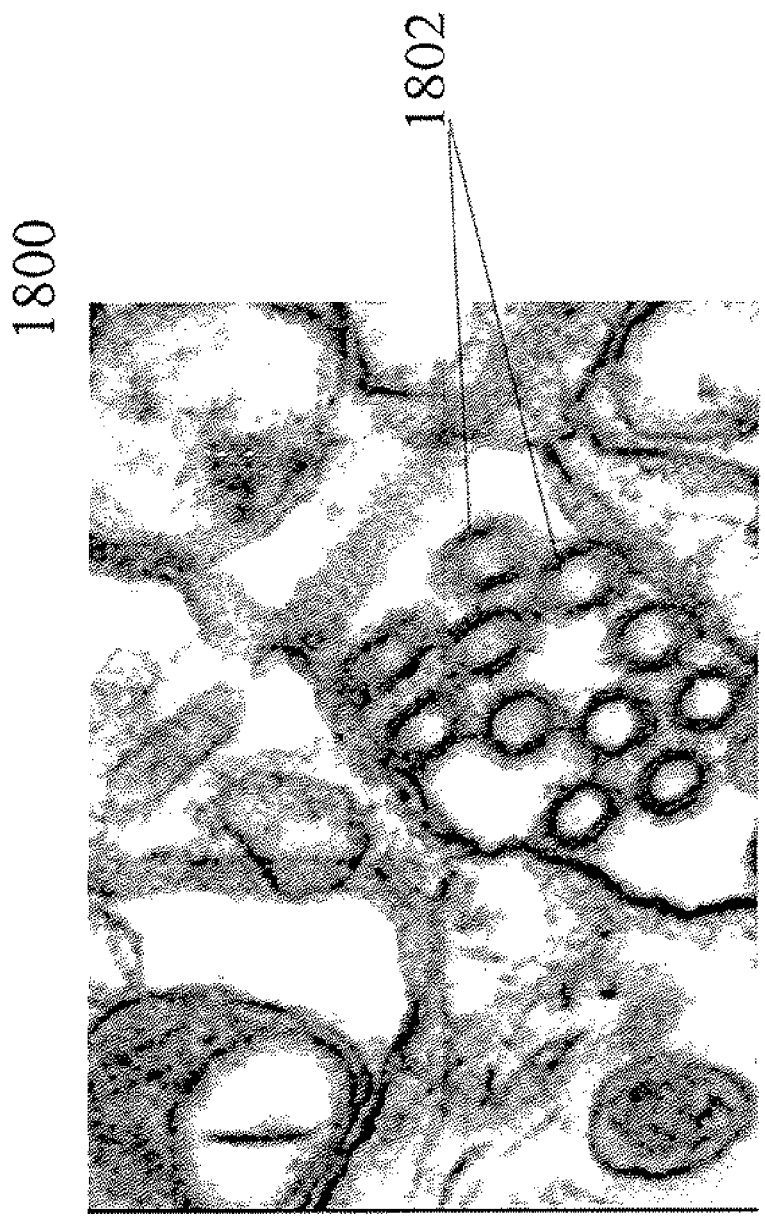
Figure 80:
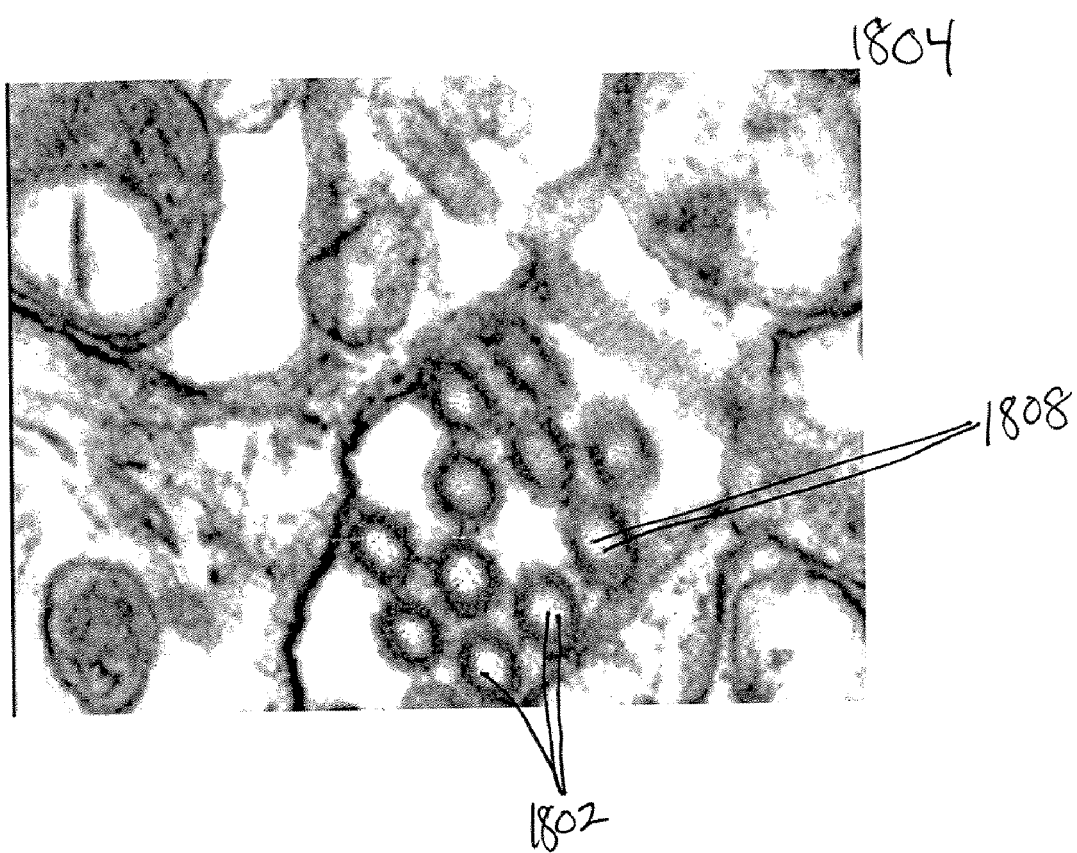

FIG. 79 is a photographed image 1800 that includes H5N1 strain cells 1802. FIG. 80 is an image 1804 generated after the image 1800 has been processed according to the synaptic web generation method described above. The image 1804 has also been compared to other virus cells (non H5N1 strain cells). The result of the comparison includes information of features 1808 of the H5N1 strain cells that are unique to it (i.e., not included in the other virus cells). In a color display the features 1808 are displayed in a unique color in order to distinguish them form the other components. The synaptic web parts that correspond to the features 1808 may be separately stored and used for later comparison to other images of raw samples.

While the preferred embodiment of the invention has been illustrated and described, as noted above, many changes can be made without departing from the spirit and scope of the invention. For example, rather than including a microscope having a digital imaging component, other sensing means could be used to gather data corresponding to an aspect of the second biological sample. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A method for data analysis and detection of avian influenza virus in a first biological sample comprising:
    receiving a first data set corresponding to an aspect of a first biological sample;
    analyzing the first data set using results of a first series of algorithms processed on a second data set corresponding to an aspect of a second biological sample known to contain avian influenza virus, wherein analyzing the first data set comprises:
        generating an algorithm value cache for the first data set by running a second series of algorithms on the first data set; and
        generating a match result by comparing the generated algorithm value cache with the results of the first series of algorithms; and
    performing a processing action based on the generated match result.

2. The method of claim 1, wherein receiving a first data set includes receiving a first data set corresponding to a digital photograph of a first biological sample taken at a magnification level and having a resolution that allows cellular abnormalities associated with an avian influenza viral infection to be seen, and wherein analyzing the first data set includes using results of a first series of algorithms processed on a second data set corresponding to a digital photograph of a second biological sample known to contain avian influenza virus, wherein the digital photograph of the second biological sample has a resolution that allows cellular abnormalities associated with an avian influenza viral infection to be seen.

3. The method of claim 1, wherein receiving a first data set includes receiving a first data set corresponding to a digital photograph of a first biological sample taken at a magnification level and having a resolution that allows avian influenza virus components to be seen, and wherein analyzing the first data set includes using results of a first series of algorithms processed on a second data set corresponding to a digital photograph of a second biological sample known to contain avian influenza virus, wherein the digital photograph of the second biological sample was taken at a magnification level and has a resolution that allows avian influenza virus components to be seen.

4. The method of claim 1, wherein receiving a first data set corresponding to an aspect of a first biological sample includes receiving a first data set corresponding to at least one of a digital photograph of the biological sample, a digital photograph of the biological sample after the biological sample had been processed with a staining agent, a digital photograph of the biological sample after the biological sample had been exposed to a reagent such as a chemical or an enzymatic reagent, an x-ray of the biological sample, an image of the biological sample using MRI technology, an ultrasound image of the biological sample, or harmonic vibration information related to the biological sample.

5. The method of claim 1, wherein the second series of algorithms includes the first series of algorithms and wherein generating an algorithm value cache comprises:
   a) retrieving a first target data element in the first data set;
   b) processing the second series of algorithms on a target data area for the retrieved first target data element;
   c) repeating a) and b) for a plurality of target data elements in the first data set; and
   d) storing the results of the processed second series of algorithms to generate the algorithm value cache.

6. The method of claim 1, wherein the second biological sample is known to contain an H5N1 strain of avian influenza virus.

7. The method of claim 1, wherein the first biological sample is a biological sample from a bird.

8. The method of claim 1, wherein the first biological sample is a biological sample from a human.

9. The method of claim 1, wherein the first and second biological samples include at least one of a blood sample, a lachrymal fluid sample, a saliva sample, a fecal sample, a buccal fluid sample, an apocrine fluid sample, an eccrine fluid sample, or a mucus sample.

10. A system for data analysis and detection of avian influenza virus in a biological sample comprising:
    a memory;
    a datastore stored in the memory that contains processed results of a first series of algorithms processed on a first data set corresponding to an aspect of a first biological sample known to contain avian influenza virus;
    a user interface;
    a processor in data communication with the user interface and the memory; and
    a software module for storage in the memory and operable by the processor, the software module comprising:
      a first component configured to run a second series of algorithms on a second data set corresponding to an aspect of a second biological sample to generate an algorithm value cache;
      a second component configured to compare the algorithm value cache to the processed results of the first series of algorithms to generate a match result; and
      a third component configured to perform a processing action based on the generated match result.

11. The system of claim 10, wherein the first and second data sets correspond to digital photographs of the first and second biological samples respectively, taken at a magnification level and having a resolution that allows cellular abnormalities associated with an avian influenza viral infection to be seen.

12. The system of claim 10, wherein the first and second data sets correspond to digital photographs of the first and second biological samples respectively, taken at a magnification level and having a resolution that allows avian influenza virus components to be seen.

13. The system of claim 10, wherein the system is a portable system further comprising a microscope for magnifying the second biological sample, the microscope having a digital imaging component in data communication with the memory for generating a digital image of the magnified second biological sample and storing the generated digital image in the memory as the second data set.

14. The system of claim 10, wherein the first biological sample is known to contain an H5N1 strain of avian influenza virus.

15. The system of claim 10, wherein the system includes at least one of a wired or a wireless networking component, and wherein the third component of the software module is configured to send a signal based on the generated match result to at least one of a remote user or a remote server over at least one of a wired or wireless network.

16. The system of claim 10, wherein the first and second biological samples include at least one of a blood sample, a lachrymal fluid sample, a saliva sample, a fecal sample, a buccal fluid sample, an apocrine fluid sample, an eccrine fluid sample or a mucus sample.

17. A system for data analysis and detection of avian influenza virus in a biological sample comprising:
    a datastore configured to contain processed results of a first series of algorithms processed on a first data set corresponding to an aspect of a first biological sample known to contain avian influenza virus;
    a user interface; and
    a processor in data communication with the datastore and the user interface, the processor comprising:
      a component configured to identify avian influenza virus in a second data set corresponding to an aspect of a second biological sample, the component comprising:
        a first sub-component configured to generate an algorithm value cache for the second data set by running a second series of algorithms on the second data set;
        a second sub-component configured to generate a match result by comparing the generated algorithm value cache with the results of the first series of algorithms processed on the first data set; and
        a third sub-component configured to perform a processing action based on the generated match result.

18. The system of claim 17, wherein the first sub-component configured to generate an algorithm value cache comprises:
    a first sub-element configured to retrieve a first target data element in the second data set;
    a second sub-element configured to process the second series of algorithms on a target data area for the retrieved first target data element;
    a third sub-element configured to direct the first sub-element and the second sub-element to retrieve additional target data elements in the second data set and process the second series of algorithms on a target data area for the retrieved additional target data elements; and
    a fourth sub-element configured to store the results of the processed second series of algorithms to generate the algorithm value cache.

* * * * *